US009782227B2

(12) United States Patent
Park et al.

(10) Patent No.: US 9,782,227 B2
(45) Date of Patent: Oct. 10, 2017

(54) PREOPERATIVELY PLANNING AN ARTHROPLASTY PROCEDURE AND GENERATING A CORRESPONDING PATIENT SPECIFIC ARTHROPLASTY RESECTION GUIDE

(71) Applicant: Howmedica Osteonics Corporation, Mahwah, NJ (US)

(72) Inventors: Ilwhan Park, Walnut Creek, CA (US); Venkata Surya Sarva, Fremont, CA (US); Irene Min Choi, Emeryville, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 0 days.

(21) Appl. No.: 15/168,405

(22) Filed: May 31, 2016

(65) Prior Publication Data
US 2016/0270859 A1    Sep. 22, 2016

Related U.S. Application Data

(63) Continuation-in-part of application No. 14/084,255, filed on Nov. 19, 2013, which is a continuation of (Continued)

(51) Int. Cl.
*A61B 34/10* (2016.01)
*A61B 17/17* (2006.01)
(Continued)

(52) U.S. Cl.
CPC .......... *A61B 34/10* (2016.02); *A61B 17/1764* (2013.01); *A61F 2/389* (2013.01);
(Continued)

(58) Field of Classification Search
CPC .................... A61B 2034/101; A61B 2034/102
See application file for complete search history.

(56) References Cited

U.S. PATENT DOCUMENTS

| 5,150,304 A | 9/1992 | Berchem |
| 5,454,717 A | 10/1995 | Andreiko |

(Continued)

FOREIGN PATENT DOCUMENTS

WO    WO 2009/134620 A2    11/2009

OTHER PUBLICATIONS

Appeal Brief, U.S. Appl. No. 11/946,002, dated Oct. 13, 2016.
(Continued)

*Primary Examiner* — David Bates
(74) *Attorney, Agent, or Firm* — Polsinelli PC

(57) ABSTRACT

A method of manufacturing an arthroplasty jig is disclosed herein. The method may include the following: generate two dimensional image data of a patient joint to undergo arthroplasty, identify in the two dimensional image data a first point corresponding to an articular surface of a bone forming the joint, identify a second point corresponding to an articular surface of an implant, identify a location of a resection plane when the first point is correlated with the second point, and create the arthroplasty jig with a resection guide located according to the identified location of the resection plane.

27 Claims, 77 Drawing Sheets

Related U.S. Application Data application No. 13/086,275, filed on Apr. 13, 2011, now Pat. No. 8,617,171, which is a continuation-in-part of application No. 12/760,388, filed on Apr. 14, 2010, now Pat. No. 8,737,700, which is a continuation-in-part of application No. 12/563,809, filed on Sep. 21, 2009, now Pat. No. 8,545,509, said application No. 12/760,388 is a continuation-in-part of application No. 12/546,545, filed on Aug. 24, 2009, now Pat. No. 8,715,291, and a continuation-in-part of application No. 12/111,924, filed on Apr. 29, 2008, now Pat. No. 8,480,679, and a continuation-in-part of application No. 11/959,344, said application No. 12/563,809 is a continuation-in-part of application No. 12/505,056, filed on Jul. 17, 2009, now Pat. No. 8,777,875, said application No. 12/563,809 is a continuation-in-part of application No. 12/111,924, filed on Apr. 29, 2008, now Pat. No. 8,480,679, and a continuation-in-part of application No. 11/959,344, filed on Dec. 18, 2007, now Pat. No. 8,221,430.

(60) Provisional application No. 61/102,692, filed on Oct. 3, 2008, provisional application No. 61/083,053, filed on Jul. 23, 2008.

(51) Int. Cl.
  A61F 2/38  (2006.01)
  A61F 2/46  (2006.01)
  G06K 9/20  (2006.01)
  G06T 19/00 (2011.01)
  G06K 9/62  (2006.01)
  A61B 6/00  (2006.01)

(52) U.S. Cl.
  CPC .......... *A61F 2/3859* (2013.01); *A61F 2/4657* (2013.01); *G06K 9/2063* (2013.01); *G06K 9/6202* (2013.01); *G06T 19/00* (2013.01); *A61B 6/505* (2013.01); *A61B 2034/102* (2016.02); *A61B 2034/105* (2016.02); *A61B 2034/108* (2016.02); *A61F 2002/4658* (2013.01); *A61F 2002/4668* (2013.01); *G06K 2209/055* (2013.01); *G06T 2210/41* (2013.01); *Y10T 29/49* (2015.01)

(56) References Cited

U.S. PATENT DOCUMENTS

| | | | |
|---|---|---|---|
| 5,735,856 | A | 4/1998 | McCue |
| 2002/0055679 | A1 | 5/2002 | Sati |
| 2002/0183760 | A1 | 12/2002 | McGovern |
| 2006/0093240 | A1 | 5/2006 | Sabuncu et al. |
| 2007/0270680 | A1* | 11/2007 | Sheffer ............... A61B 90/36 600/407 |
| 2009/0089026 | A1 | 4/2009 | Rodriguez Y Baena |
| 2010/0036252 | A1 | 2/2010 | Chalana et al. |
| 2016/0213491 | A1 | 7/2016 | Schoenefeld |
| 2016/0228194 | A1 | 8/2016 | Park et al. |
| 2016/0228195 | A1 | 8/2016 | Park et al. |
| 2016/0228196 | A1 | 8/2016 | Park et al. |
| 2016/0228197 | A1 | 8/2016 | Park et al. |
| 2016/0270856 | A1 | 9/2016 | Park et al. |
| 2016/0270857 | A1 | 9/2016 | Park et al. |
| 2016/0270858 | A1 | 9/2016 | Park et al. |
| 2016/0310217 | A1 | 10/2016 | Park et al. |
| 2016/0354092 | A1 | 12/2016 | Park |
| 2017/0007275 | A1 | 1/2017 | Park et al. |

OTHER PUBLICATIONS

Canadian Office Action, 2721735, dated Aug. 24, 2016.
Canadian Office Action, CA2721762, dated Jul. 20, 2016.
Extended European Search Report, European Appl. No. 14765072.5, dated Sep. 22, 2016.
Final Office Action, U.S. Appl. No. 13/923,093, dated Jul. 14, 2016.
Final Office Action, U.S. Appl. No. 14/011,998, dated Jul. 14, 2016.
Final Office Action, U.S. Appl. No. 14/869,762, dated Oct. 6, 2016.
Non-Final Office Action, U.S. Appl. No. 14/335,460, dated Aug. 30, 2016.
Non-Final Office Action, U.S. Appl. No. 14/272,147, dated Jun. 17, 2016.
Non-Final Office Action, U.S. Appl. No. 14/335,431, dated Sep. 14, 2016.
Non-Final Office Action, U.S. Appl. No. 14/946,106, dated Jun. 23, 2016.
Non-Final Office Action, U.S. Appl. No. 15/168,359, dated Aug. 17, 2016.
Notice of Allowance, U.S. Appl. No. 15/167,614, dated Aug. 26, 2016.
Preliminary Amendment, U.S. Appl. No. 15/202,417, dated Sep. 15, 2016.
Response to Non-Final Office Action, U.S. Appl. No. 14/272,147, dated Sep. 13, 2016.
Response to Non-Final Office Action, U.S. Appl. No. 14/869,762, dated Jun. 29, 2016.
Response to Non-Final Office Action, U.S. Appl. No. 15/168,359, dated Oct. 24, 2016.
Response to Restriction, U.S. Appl. No. 14/335,431, dated Aug. 31, 2016.
Restriction Requirement, U.S. Appl. No. 14/335,431, dated Aug. 12, 2016.
Canadian Office Action, CA2642616, dated Jan. 12, 2017.
Decision on Appeal, U.S. Appl. No. 11/642,385, dated Mar. 2, 2017.
EP Examination Report, EP09739422.5, dated Mar. 7, 2017.
EP Examination Report, EP13188389.4, dated Jan. 30, 2017.
Examiner's Answer in appeal, U.S. Appl. No. 11/946,002, dated Jan. 23, 2017.
Extended European Search Report, EP11769533.8, dated Jan. 9, 2017.
International Search Report and Written Opinion, PCT/US2016/034847, dated Dec. 8, 2016.
Non-Final Office Action, U.S. Appl. No. 14/084,255, dated Jan. 19, 2017.
Non-Final Office Action, U.S. Appl. No. 14/086,849, dated Nov. 2, 2016.
Non-Final Office Action, U.S. Appl. No. 14/086,878, dated Nov. 10, 2016.
Non-Final Office Action, U.S. Appl. No. 14/928,767, dated Jan. 12, 2017.
Non-Final Office Action, U.S. Appl. No. 15/168,359, dated Dec. 30, 2016.
Notice of Allowance, U.S. Appl. No. 13/923,093, dated Jan. 4, 2017.
Notice of Allowance, U.S. Appl. No. 14/011,998, dated Jan. 11, 2017.
Notice of Allowance, U.S. Appl. No. 14/272,147, dated Nov. 21, 2016.
Notice of Allowance, U.S. Appl. No. 14/335,460, dated Mar. 27, 2017.
Notice of Allowance, U.S. Appl. No. 14/946,106, dated Feb. 3, 2017.
Notice of Allowance, U.S. Appl. No. 15/242,312, dated Jan. 3, 2017.
Response to Final Office Action, U.S. Appl. No. 14/084,255, dated Dec. 22, 2016.
Response to Final Office Action, U.S. Appl. No. 14/869,762, dated Jan. 4, 2017.
Response to Non-Final Office Action, U.S. Appl. No. 14/086,849, dated Apr. 3, 2017.
Response to Non-Final Office Action, U.S. Appl. No. 14/086,878, dated Apr. 4, 2017.
Response to Non-Final Office Action, U.S. Appl. No. 14/335,460, dated Jan. 27, 2017.
Response to Non-Final Office Action, U.S. Appl. No. 15/168,359, dated Mar. 30, 2017.

(56) References Cited

OTHER PUBLICATIONS

Response to Restriction, U.S. Appl. No. 15/274,717, dated Jan. 9, 2017.
Restriction Requirement, U.S. Appl. No. 15/274,717, dated Nov. 16, 2016.
Supplemental Amendment, U.S. Appl. No. 14/869,762, dated Jan. 13, 2017.

* cited by examiner

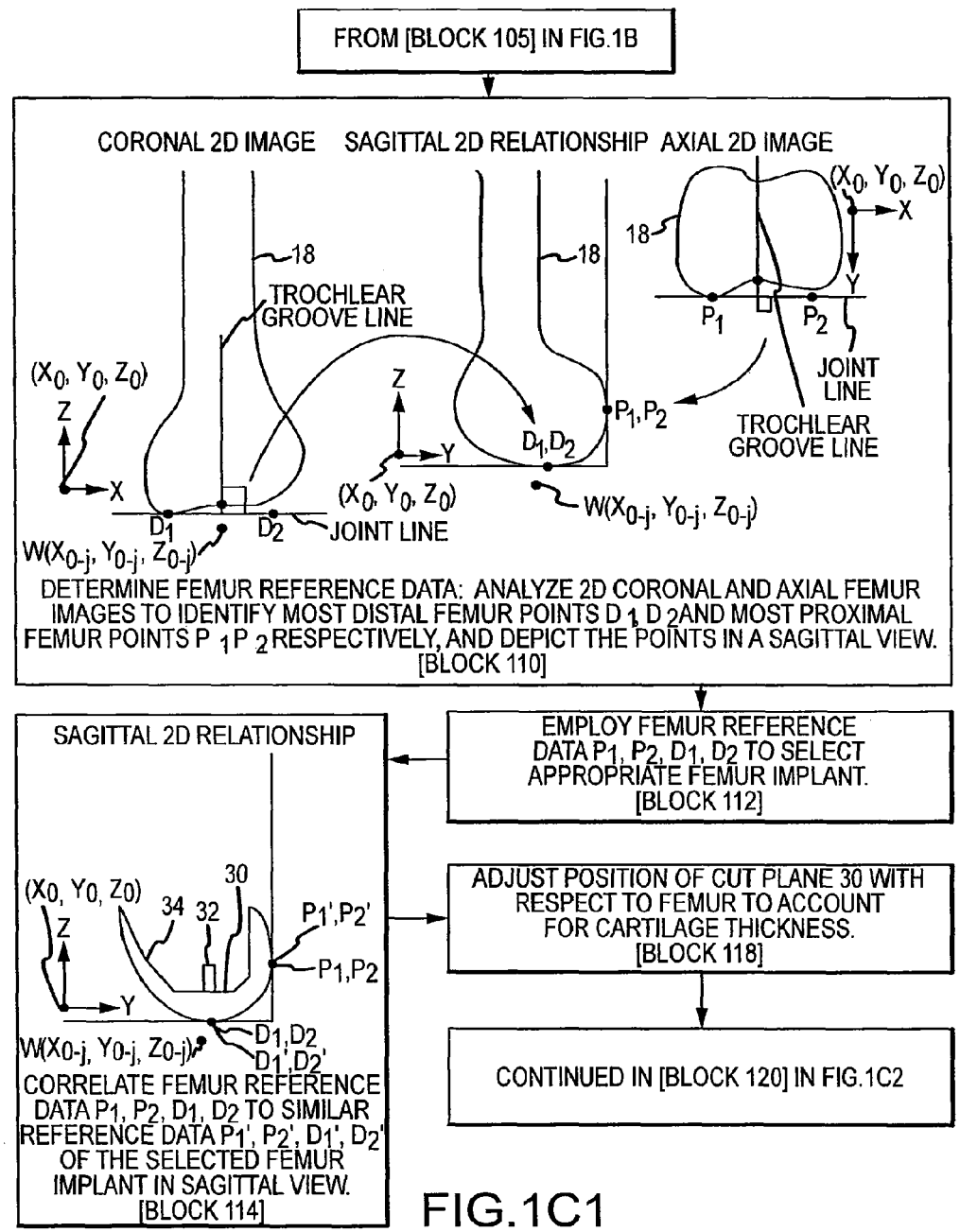
FIG.1C1

FROM [BLOCK 118] IN FIG. 1C1

REPEAT PROCESS OF BLOCK 110 FOR TIBIA IN SIMILAR MANNER, EXCEPT SAGITTAL AND CORONAL IMAGE SLICES OF TIBIA ARE ANALYZED TO IDENTIFY THE LOWEST AND MOST ANTERIOR AND POSTERIOR POINTS OF THE TIBIA RECESSED CONDYLAR SURFACES, THIS TIBIA REFERENCE DATA THEN BEING PROJECTED ON TO AN AXIAL VIEW.
[BLOCK 120]

EMPLOY TIBIA REFERENCE DATA TO SELECT APPROPRIATE TIBIA IMPLANT.
[BLOCK 121]

REPEAT PROCESS OF BLOCK 114 FOR TIBIA IN SIMILAR MANNER, EXCEPT IN AN AXIAL VIEW CORRELATE TIBIA REFERENCE DATA TO SIMILAR REFERENCE DATA OF THE SELECTED TIBIA IMPLANT.
[BLOCK 122]

ADJUST POSITION OF CUT PLANE 30 WITH RESPECT TO TIBIA TO ACCOUNT FOR CARTILAGE THICKNESS.
[BLOCK 123]

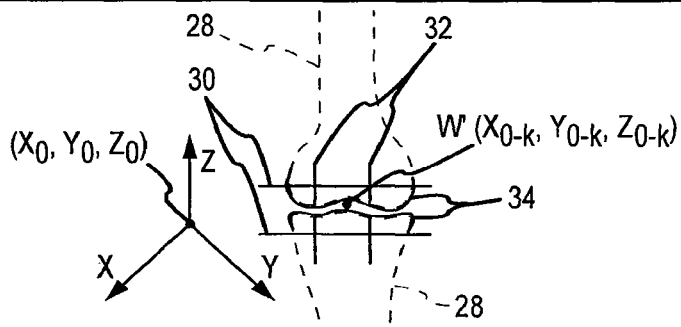

PACKAGE SAW CUT LOCATION 30 AND DRILL HOLE LOCATIONS 32 ASSOCIATED WITH PRE-OPERATIVE PLANNING ("POP") OF FEMUR AND TIBIA IMPLANTS 34 RELATIVE TO THE FEMUR AND TIBIA DATA 28 AND THE UPDATED POINT $W'(X_{0-k}, Y_{0-k}, Z_{0-k})$, WHICH MAY BE DIFFERENT FROM ORIGINAL POINT $W(X_{0-j}, Y_{0-j}, Z_{0-j})$ DUE TO ADJUSTMENTS TO DATA POSITIONS DURING ANY ONE OR MORE OF THE PROCESSES OF BLOCKS 110-124.
[BLOCK 124]

CONTINUED IN [BLOCK 125] IN FIG.1E

FIG.1C2

```
┌─────────────────────────────────────────────────────┐
│      MEASURE THE MINIMUM CARTILAGE THICKNESS FOR    │
│      THE UNDAMAGED AND DAMAGED FEMORAL CONDYLES.    │
│                     [BLOCK 1170]                    │
└─────────────────────────────────────────────────────┘
                           │
                           ▼
┌─────────────────────────────────────────────────────┐
│   USE THE CARTILAGE THICKNESS MEASURED FOR THE LEAST│
│   DAMAGED CONDYLE CARTILAGE AS THE CARTILAGE        │
│   THICKNESS REFERENCE FOR POP.                      │
│                     [BLOCK 1175]                    │
└─────────────────────────────────────────────────────┘
```

FIG.14E

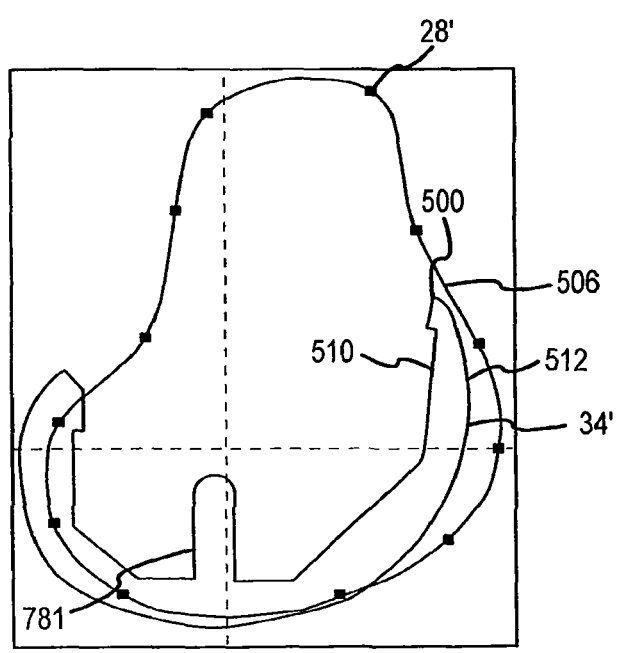
FIG.31A1

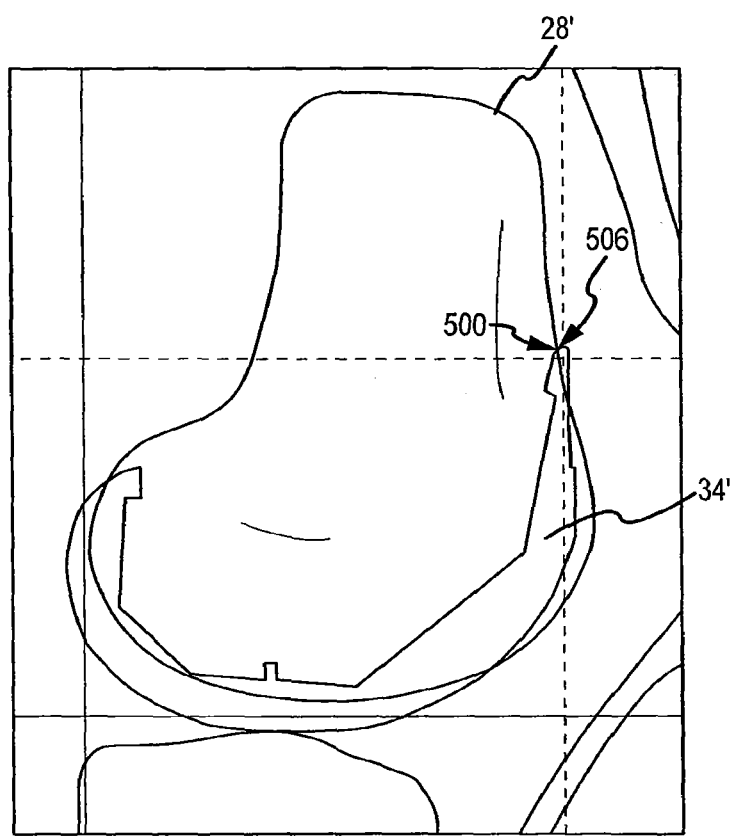
FIG.31A2

PREOPERATIVELY PLANNING AN ARTHROPLASTY PROCEDURE AND GENERATING A CORRESPONDING PATIENT SPECIFIC ARTHROPLASTY RESECTION GUIDE

CROSS REFERENCE TO RELATED APPLICATIONS

The present application is a continuation-in-part of U.S. application Ser. No. 14/084,255 filed Nov. 19, 2013, which application is a continuation of U.S. patent application Ser. No. 13/086,275 ("the '275 application"), filed Apr. 13, 2011, and titled "Preoperatively Planning an Arthroplasty Procedure and Generating a Corresponding Patient Specific Arthroplasty Resection Guide," now U.S. Pat. No. 8,617, 171. The '275 application is a continuation-in-part ("CIP") of U.S. patent application Ser. No. 12/760,388 ("the '388 application"), filed Apr. 14, 2010, now U.S. Pat. No. 8,737, 700.

The '388 application is a CIP application of U.S. patent application Ser. No. 12/563,809 ("the '809 application), filed Sep. 21, 2009, and titled "Arthroplasty System and Related Methods," now U.S. Pat. No. 8,545,509, which claims priority to U.S. patent application 61/102,692 ("the '692 application"), filed Oct. 3, 2008, and titled "Arthroplasty System and Related Methods," The '388 application is also a CIP application of U.S. patent application Ser. No. 12/546, 545 ("the 545 application"), filed Aug. 24, 2009, and titled "Arthroplasty System and Related Methods," now U.S. Pat. No. 8,715,291, which claims priority to the '692 application.

The '545 application is also a CIP application of U.S. patent application Ser. No. 12/111,924 ("the '924 application"), filed Apr. 29, 2008, and titled "Generation of a Computerized Bone Model Representative of a Pre-Degenerated State and Useable in the Design and Manufacture of Arthroplasty Devices," now U.S. Pat. No. 8,480,679. The '545 application is also a CIP application of U.S. patent application Ser. No. 11/959,344 ("the '344 application), filed Dec. 18, 2007, and titled "System and Method for Manufacturing Arthroplasty Jigs," now U.S. Pat. No. 8,221,430.

The '809 application is a CIP application of U.S. patent application Ser. No. 12/505,056 ("the '056 application"), filed Jul. 17, 2009, and titled "System and Method for Manufacturing Arthroplasty Jigs Having Improved Mating Accuracy," now U.S. Pat. No. 8,777,875. The '056 application claims priority to U.S. patent application 61/083,053, filed Jul. 23, 2008, and titled "System and Method for Manufacturing Arthroplasty Jigs Having Improved Mating Accuracy," The '809 application is also a CIP application of the '924 application. The '809 application is also a CIP application of the '344 application.

The present application claims priority to all of the above mentioned applications and hereby incorporates by reference all of the above-mentioned applications in their entireties into the present application.

FIELD OF THE INVENTION

The present invention relates to customized arthroplasty cutting jigs. More specifically, the present invention relates to systems and methods of manufacturing such jigs.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs may rely on a plurality of images from a MRI scan or CT scan to construct a 3D bone model. The image slice orientation of the MRI scan or CT scan is at least partially dependent upon the imaging system operator to place the localizer in various positions during the scan. This imaging process is subject to operator error, such as inaccurate placement of the localizer, thereby increasing the time, manpower and costs associated with producing the customized arthroplasty jig.

There is a need in the art for a system and method for reducing the labor associated with generating customized arthroplasty jigs. There is also a need in the art for a system and method for reducing the effects of operator error and thereby increasing the accuracy of customized arthroplasty jigs.

SUMMARY

Various embodiments of a method of manufacturing an arthroplasty jig are disclosed herein. In a first embodiment, the method may include the following: generate two dimensional image data of a patient joint to undergo arthroplasty, identify in the two dimensional image data a first point corresponding to an articular surface of a bone forming the joint, identify a second point corresponding to an articular surface of an implant, identify a location of a resection plane when the first point is correlated with the second point, and create the arthroplasty jig with a resection guide located according to the identified location of the resection plane.

In a second embodiment, the method may include the following: (a) identify a first attribute in a coronal image and a second attribute in an axial image, wherein the attributes are associated with a bone forming a portion of a patient joint, (b) place the first and second attributes in a sagittal relationship, (c) compare in the sagittal relationship the first and second attributes to respective corresponding attributes of a plurality of candidate prosthetic implants, (d) select a prosthetic implant from the comparison of step c, (e) correlate in the sagittal relationship the first and second attributes to respective corresponding attributes of the prosthetic implant, (f) identify the location of a resection plane associated with the prosthetic implant during the correlation of step e, and (g) create the arthroplasty jig with a resection guide located according to the identified location of the resection plane.

In a third embodiment, the method may include the following: (a) identify first and second attributes in a sagittal image, wherein the attributes are associated with a bone forming a portion of a patient joint, (b) place the first and second attributes in an axial relationship, (c) compare in the axial relationship the first and second attributes to respective corresponding attributes of a plurality of candidate prosthetic implants, (d) select a prosthetic implant from the comparison of step c, (e) correlate in the axial relationship the first and second attributes to respective corresponding attributes of the prosthetic implant, (f) identify the location of a resection plane associated with the prosthetic implant during the correlation of step e, and (g) create the arthroplasty jig with a resection guide located according to the identified location of the resection plane.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 1B-1E are flow chart diagrams outlining the jig production method disclosed herein.

FIG. 14E is a flow chart illustrating the method for determining cartilage thickness used to determine proper joint line.

FIGS. 31A1-31A2 are sagittal views of a 2D imaging slice of the femur wherein the 2D computer generated implant models are also shown.

DETAILED DESCRIPTION

Disclosed herein are customized arthroplasty jigs 2 and systems 4 for, and methods of, producing such jigs 2. The jigs 2 are customized to fit specific bone surfaces of specific patients. Depending on the embodiment, the jigs 2 are automatically planned and generated and may be similar to those disclosed in these three U.S. patent applications: U.S. patent application Ser. No. 11/656,323 to Park et al., titled "Arthroplasty Devices and Related Methods" and filed Jan. 19, 2007, now U.S. Pat. No. 9,017,336; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into this Detailed Description.

Figure 1A:
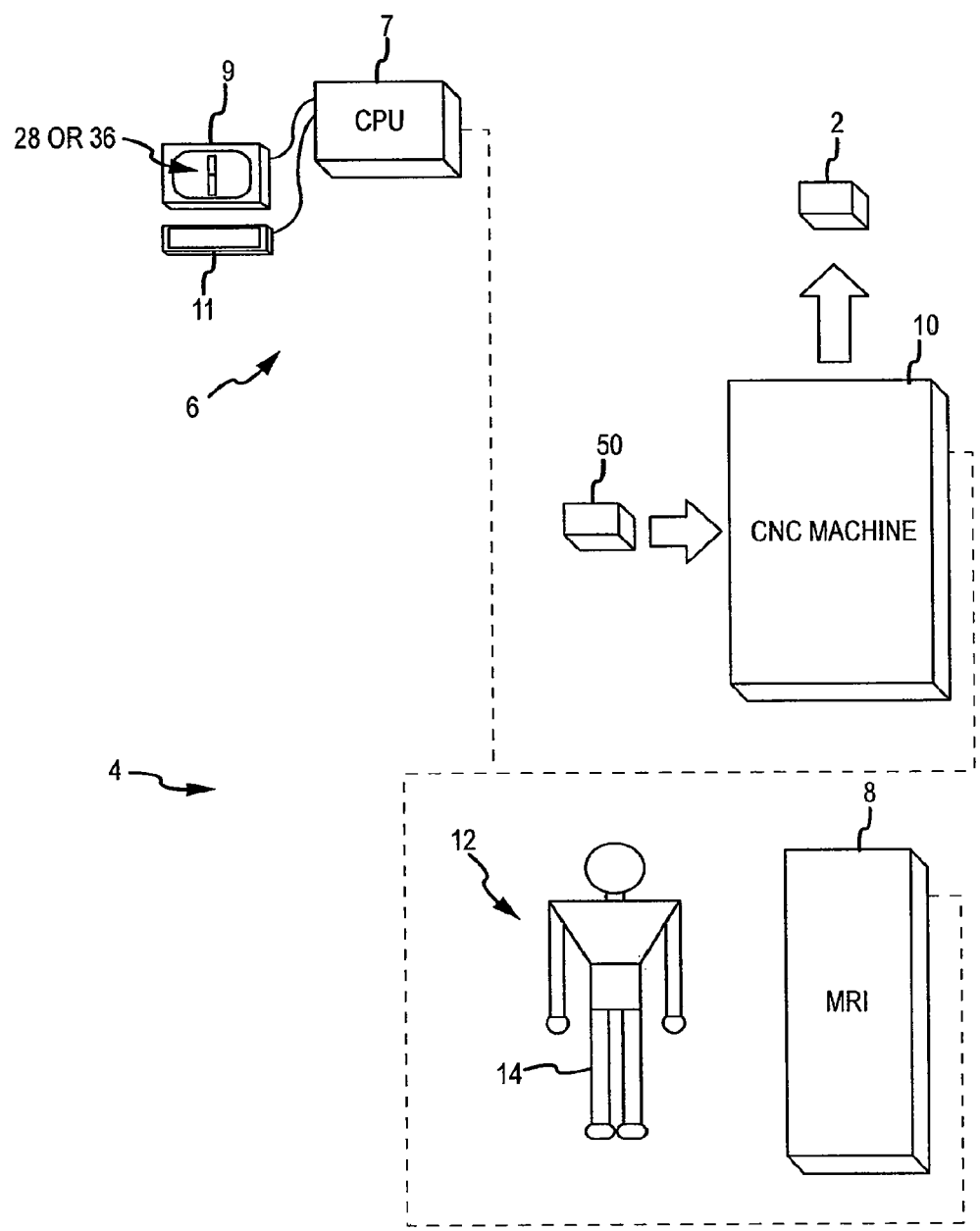
FIG. 1A is a schematic diagram of a system for employing the automated jig production method disclosed herein.

A. Overview of System and Method for Manufacturing Customized Arthroplasty Cutting Jigs For an overview discussion of the systems 4 for, and methods of, producing the customized arthroplasty jigs 2, reference is made to FIGS. 1A-1E. FIG. 1A is a schematic diagram of a system 4 for employing the automated jig production method disclosed herein. FIGS. 1B-1E are flow chart diagrams outlining the jig production method disclosed herein. The following overview discussion can be broken down into three sections.

The first section, which is discussed with respect to FIG. 1A and [blocks 100-125] of FIGS. 1B, 1C1, 1C2, and 1E, pertains to an example method of determining, in a two-dimensional ("2D") computer model environment, saw cut and drill hole locations 30, 32 relative to 2D images 16 of a patient's joint 14. The resulting "saw cut and drill hole data" 44 is planned to provide saw cuts 30 and drill holes 32 that will allow arthroplasty implants to restore the patient's joint to its pre-degenerated or natural alignment state.

Figure 1B:
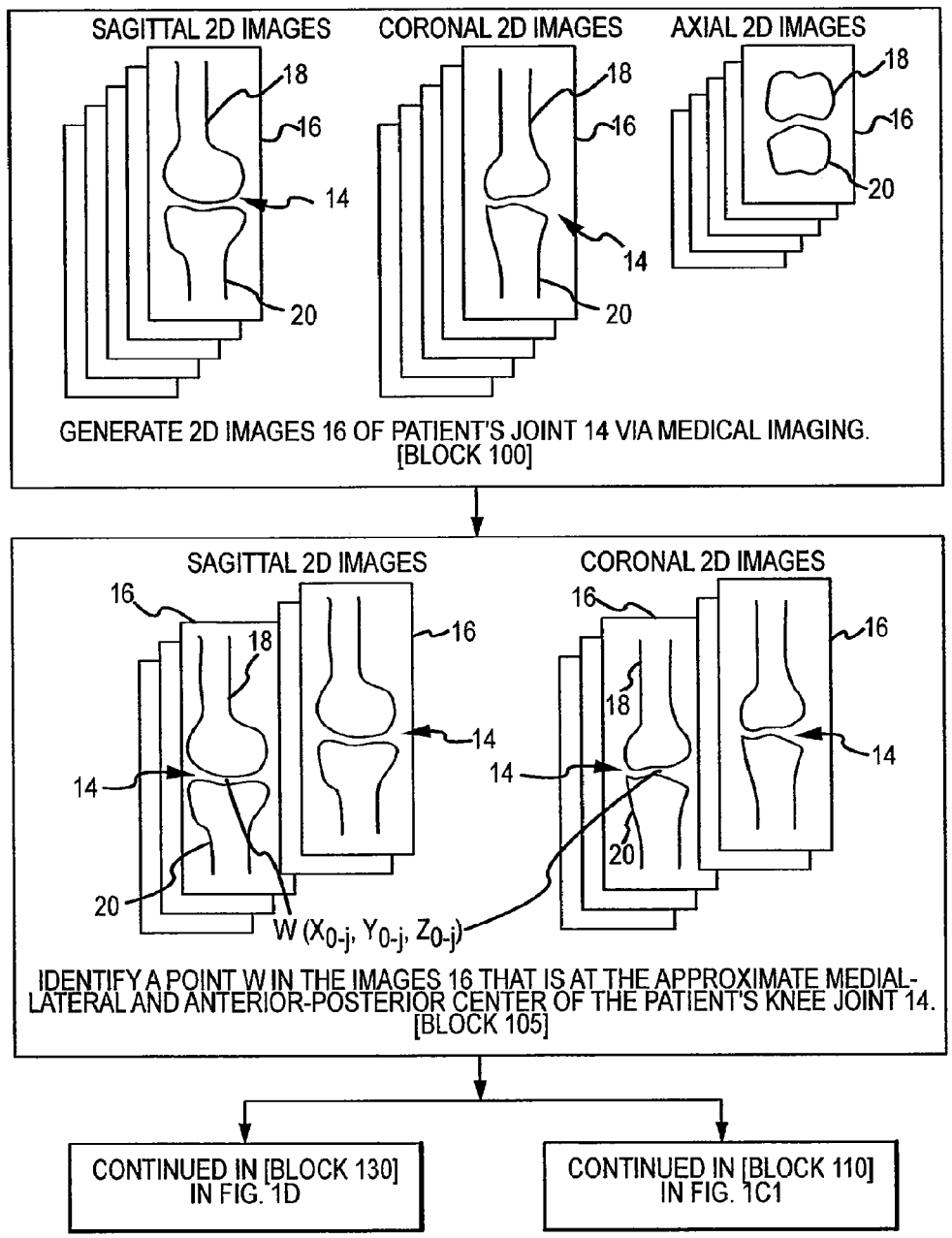
Figure 1D:
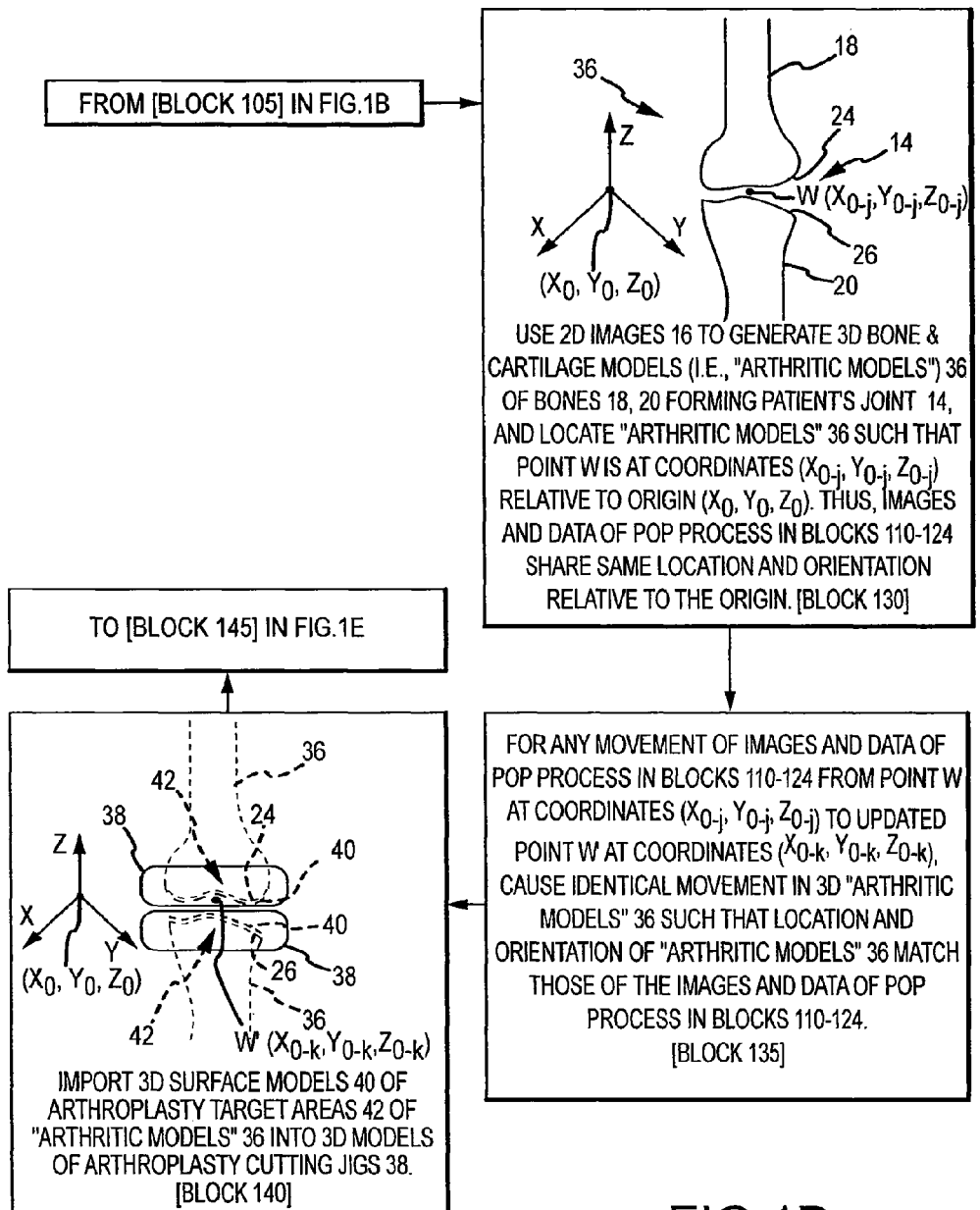
Figure 1E:
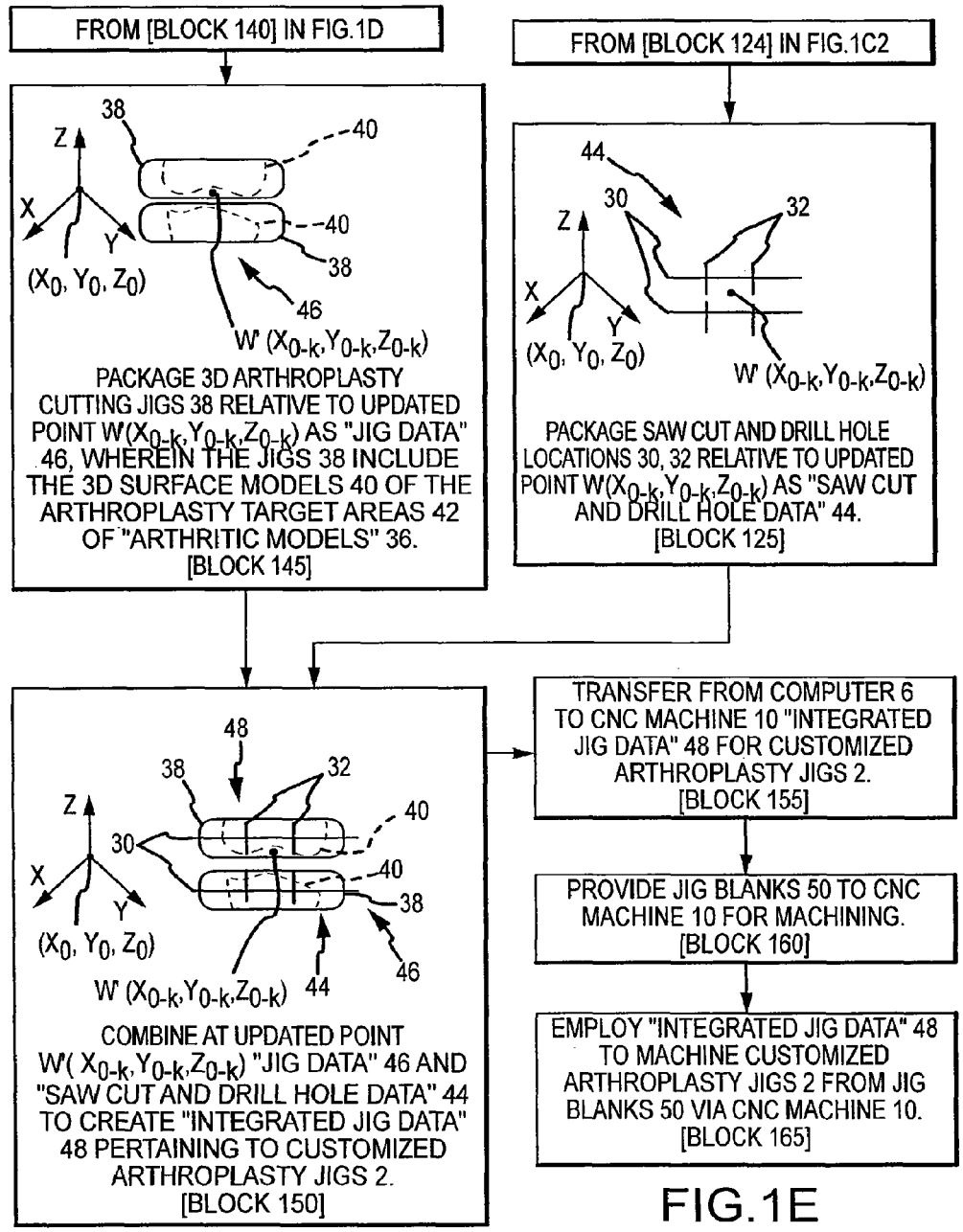

The second section, which is discussed with respect to FIG. 1A and [blocks 100-105 and 130-145] of FIGS. 1B, 1D, and 1E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

The third section, which is discussed with respect to FIG. 1A and [blocks 150-165] of FIG. 1E, pertains to a method of combining or integrating the "saw cut and drill hole data" 44 with the "jig data" 46 to result in "integrated jig data" 48. The "integrated jig data" 48 is provided to the CNC machine 10 or other rapid production machine (e.g., a stereolithography apparatus ("SLA") machine) for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state or natural alignment state.

As shown in FIG. 1A, the system 4 includes a computer 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

As indicated in FIG. 1A, a patient 12 has a joint 14 (e.g., a knee, elbow, ankle, wrist, hip, shoulder, skull/vertebrae or vertebrae/vertebrae interface, etc.) to be replaced. The patient 12 has the joint 14 scanned in the imaging machine 8. The imaging machine 8 makes a plurality of scans of the joint 14, wherein each scan pertains to a thin slice of the joint 14.

As can be understood from FIG. 1B, the plurality of scans is used to generate a plurality of two-dimensional ("2D") images 16 of the joint 14 [block 100]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description. The images 16 may be a variety of orientations, including, for example, sagittal 2D images, coronal 2D images and axial 2D images.

As can be understood from FIG. 1A, the 2D images are sent to the computer 6 for analysis and for creating computer generated 2D models and 3D models. In one embodiment, the bone surface contour lines of the bones 18, 20 depicted in the image slices 16 may be auto segmented via an image segmentation process as disclosed in U.S. Patent Application 61/126,102, which was filed Apr. 30, 2008, is entitled System and Method for Image Segmentation in Generating Computer Models of a Joint to Undergo Arthroplasty, and is hereby incorporated by reference into the present application in its entirety.

As indicated in FIG. 1B, in one embodiment, reference point W is identified in the 2D images 16 [block 105]. In one embodiment, as indicated in [block 105] of FIG. 1A, reference point W may be at the approximate medial-lateral and anterior-posterior center of the patient's joint 14. In other embodiments, reference point W may be at any other location in the 2D images 16, including anywhere on, near or away from the bones 18, 20 or the joint 14 formed by the bones 18, 20. Reference point W may be defined at coordinates $(X_{0-j}, Y_{0-j}, Z_{0-j})$ relative to an origin $(X_0, Y_0, Z_0)$ of an X-Y-Z axis and depicted in FIGS. 1B-1D as W $(X_{0-j}, Y_{0-j}, Z_{0-j})$. Throughout the processes described herein, to allow for correlation between the different types of images, models or any other data created from the images, movements of such images, models or any other data created form the images may be tracked and correlated relative to the origin.

As described later in this overview, point W may be used to locate the 2D images 16 and computer generated 3D model 36 created from the 2D images 16 respectively with the implant images 34 and jig blank model 38 and to integrate information generated via the POP process. Depending on the embodiment, point W, which serves as a position and/or orientation reference, may be a single point, two points, three points, a point plus a plane, a vector, etc., so long as the reference point W can be used to position and/or orient the 2D images 16, 34 and 3D models 36, 38 relative to each other as needed during the POP process.

As shown in FIG. 1C1, the coronal and axial 2D images 16 of the femur 18 forming the patient's joint 14 are analyzed to determine femur reference data [block 110]. For example, the coronal 2D images are analyzed to determine the most distal femur point $D_1$ on a healthy condyle and a joint line perpendicular to a trochlear groove line is used to estimate the location of a hypothetical most distal point $D_2$ on the damaged condyle. Similarly, the axial 2D images are analyzed to determine the most posterior femur point $P_1$ on a healthy condyle and a joint line perpendicular to a trochlear groove line is used to estimate the location of a hypothetical most posterior point $P_2$ on the damaged condyle. The femur reference data points $D_1$, $D_2$, $P_1$, $P_2$ is mapped or otherwise imported to a sagittal or y-z plane in a computer environment and used to determine the sagittal or y-z plane relationship between the femur reference data points $D_1$, $D_2$, $P_1$, $P_2$. The femur reference data $D_1$, $D_2$, $P_1$, $P_2$ is then used to choose candidate femoral implant(s). [Block 112]. The femur reference data points $D_1$, $D_2$, $P_1$, $P_2$ are respectively correlated with similar reference data points $D_1'$, $D_2'$, $P_1'$, $P_2'$ of the selected femur implant 34 in a sagittal or y-z plane [block 114]. This correlation determines the locations and orientations of the cut plane 30 and drill holes 32 needed to cause the patient's joint to returned to a natural, pre-deteriorated alignment with the selected implant 34. The cut plane 30 and drill hole 32 locations determined in block 114 are adjusted to account for cartilage thickness [block 118].

As shown in FIG. 1C2 at block 120, tibia reference data is determined from the images in a manner similar to the process of block 110, except different image planes are employed. Specifically, sagittal and coronal images slices of the tibia are analyzed to identify the lowest (i.e., most distal) and most anterior and posterior points of the tibia recessed condylar surfaces. This tibia reference data is then projected onto an axial view. The tibia reference data is used to select an appropriate tibia implant [Block 121]. The tibia reference data is correlated to similar reference data of the selected tibia implant in a manner similar to that of block 114, except the correlation takes place in an axial view [Block 122]. The cut plane 30 associated with the tibia implant's position determined according to block 122 is adjusted to account for cartilage thickness [Block 123].

Once the saw cut locations 30 and drill hole locations 32 associated with the POP of the femur and tibia implants 34 has been completed with respect to the femur and tibia data 28 (e.g., the 2D femur and tibia images 16 and reference point W), the saw cut locations 30 and drill hole locations 32 are packaged relative to the reference point $W(X_{0-j}, Y_{0-j}, Z_{0-j})$ [Block 124]. As the images 16 and other data created from the images or by employing the images may have moved during any of the processes discussed in blocks 110-123, the reference point $W(X_{0-j}, Y_{0-j}, Z_{0-j})$ for the images or associated data may become updated reference point W' at coordinates $(X_{0-k}, Y_{0-k}, Z_{0-k})$ relative to an origin $(X_0, Y_0, Z_0)$ of an X-Y-Z axis. For example, during the correlation process discussed in blocks 114 and 122, the implant reference data may be moved towards the bone image reference data or, alternatively, the bone image reference data may be moved towards the implant reference data. In the latter case, the location of the bone reference data will move from reference point $W(X_{0-j}, Y_{0-j}, Z_{0-j})$ to updated reference point $W'(X_{0-k}, Y_{0-k}, Z_{0-k})$, and this change in location with respect to the origin will need to be matched by the arthritic models 36 to allow for "saw cut and drill hole" data 44 obtained via the POP process of blocks 110-125 to be merged with "jig data" 46 obtained via the jig mating surface defining process of blocks 130-145, as discussed below.

As can be understood from FIG. 1E, the POP process may be completed with the packaging of the saw cut locations 30 and drill hole locations 32 with respect to the updated reference point $W'(X_{0-k}, Y_{0-k}, Z_{0-k})$ as "saw cut and drill hole data" 44 [Block 125]. The "saw cut and drill hole data" 44 is then used as discussed below with respect to [block 150] in FIG. 1E.

In one embodiment, the POP procedure is a manual process, wherein 2D bone images 28 (e.g., femur and tibia 2D images in the context of the joint being a knee) are manually analyzed to determine reference data to aid in the selection of a respective implant 34 and to determine the proper placement and orientation of saw cuts and drill holes that will allow the selected implant to restore the patient's joint to its natural pre-deteriorated state. (The reference data for the 2D bone images 28 may be manually calculated or calculated by a computer by a person sitting in front of a computer 6 and visually observing the images 28 on the computer screen 9 and determining the reference data via the computer controls 11. The data may then be stored and utilized to determine the candidate implants and proper location and orientation of the saw cuts and drill holes. In other embodiments, the POP procedure is totally computer automated or a combination of computer automation and manual operation via a person sitting in front of the computer.

In some embodiments, once the selection and placement of the implant has been achieved via the 2D POP processes described in blocks 110-125, the implant selection and placement may be verified in 2D by superimposing the implant models 34 over the bone images data, or vice versa. Alternatively, once the selection and placement of the implant has been achieved via the 2D POP processes described in blocks 110-125, the implant selection and placement may be verified in 3D by superimposing the implant models 34 over 3D bone models generated from the images 16. Such bone models may be representative of how the respective bones may have appeared prior to degeneration. In superimposing the implants and bones, the joint surfaces of the implant models can be aligned or caused to correspond with the joint surfaces of the 3D bone models. This ends the overview of the POP process. A more detailed discussion of various embodiments of the POP process is provided later in this Detailed Description As can be understood from FIG. 1D, the 2D images 16 employed in the 2D POP analysis of blocks 110-124 of FIGS. 1C1-1C2 are also used to create computer generated 3D bone and cartilage models (i.e., "arthritic models") 36 of the bones 18, 20 forming the patient's joint 14 [block 130]. Like the above-discussed 2D images and femur and tibia reference data, the arthritic models 36 are located such that point W is at coordinates $(X_{0-j}, Y_{0-j}, Z_{0-j})$ relative to the origin $(X_0, Y_0, Z_0)$ of the X-Y-Z axis [block 130]. Thus, the 2D images and femur and tibia data of blocks 110-125 and arthritic models 36 share the same location and orientation relative to the origin $(X_0, Y_0, Z_0)$. This position/orientation relationship is generally maintained throughout the process discussed with respect to FIGS. 11B-1E. Accordingly, movements relative to the origin $(X_0, Y_0, Z_0)$ of the 2D images and femur and tibia data of blocks 110-125 and the various descendants thereof (i.e., bone cut locations 30 and drill hole locations 32) are also applied to the arthritic models 36 and the various descendants thereof (i.e., the jig models 38). Maintaining the position/orientation relationship between the 2D images and femur and tibia data of blocks 110-125 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2, as discussed with respect to block 150 of FIG. 1E.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

The arthritic models 36 depict the bones 18, 20 in the present deteriorated condition with their respective degenerated joint surfaces 24, 26, which may be a result of osteoarthritis, injury, a combination thereof, etc. The arthritic models 36 also include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1D and already mentioned above, to coordinate the positions/orientations of the 2D images and femur and tibia data of blocks 110-125 and arthritic models 36 and their respective descendants, any movement of the 2D images and femur and tibia data of blocks 110-125 from point W to point W' is tracked to cause a generally identical displacement for the "arthritic models" 36, and vice versa [block 135].

As depicted in FIG. 1D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point W' ($X_{0-k}$, $Y_{0-k}$, $Z_{0-k}$) can also be imported into the jig models 38, resulting in jig models 38 positioned and oriented relative to point W' ($X_{0-k}$, $Y_{0-k}$, $Z_{0-k}$) to allow their integration with the bone cut and drill hole data 44 of [block 125].

In one embodiment, the procedure for indexing the jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007, now U.S. Pat. No. 8,221,430 and is incorporated by reference in its entirety into this Detailed Description. For example, a computer program may create 3D computer generated surface models 40 of the arthroplasty target areas 42 of the arthritic models 36. The computer program may then import the surface models 40 and point W' ($X_{0-k}$, $Y_{0-k}$, $Z_{0-k}$) into the jig models 38, resulting in the jig models 38 being indexed to matingly receive the arthroplasty target areas 42 of the arthritic models 36. The resulting jig models 38 are also positioned and oriented relative to point W' ($X_{0-k}$, $Y_{0-k}$, $Z_{0-k}$) to allow their integration with the bone cut and drill hole data 44 of [block 125].

In one embodiment, the arthritic models 36 may be 3D volumetric models as generated from the closed-loop process discussed in U.S. patent application Ser. No. 11/959, 344 filed by Park. In other embodiments, the arthritic models 36 may be 3D surface models as generated from the open-loop process discussed in U.S. patent application Ser. No. 11/959,344 filed by Park.

In one embodiment, the models 40 of the arthroplasty target areas 42 of the arthritic models 36 may be generated via an overestimation process as disclosed in U.S. Provisional Patent Application 61/083,053, which is entitled System and Method for Manufacturing Arthroplasty Jigs Having Improved Mating Accuracy, was filed by Park Jul. 23, 2008, and is hereby incorporated by reference in its entirety into this Detailed Description.

As indicated in FIG. 1E, in one embodiment, the data regarding the jig models 38 and surface models 40 relative to point W' ($X_{0-k}$, $Y_{0-k}$, $Z_{0-k}$) is packaged or consolidated as the "jig data" 46 [block 145]. The "jig data" 46 is then used as discussed below with respect to [block 150] in FIG. 1E.

As can be understood from FIG. 1E, the "saw cut and drill hole data" 44 is integrated with the "jig data" 46 to result in the "integrated jig data" 48 block 1501. As explained above, since the "saw cut and drill hole data" 44, "jig data" 46 and their various ancestors (e.g., 2D images and femur and tibia data of blocks 110-125 and models 36, 38) are matched to each other for position and orientation relative to point W and W', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated state or natural alignment state.

As can be understood from FIGS. 1A and 1E, the "integrated jig data" 44 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50 [block 165].

Figure 2A:
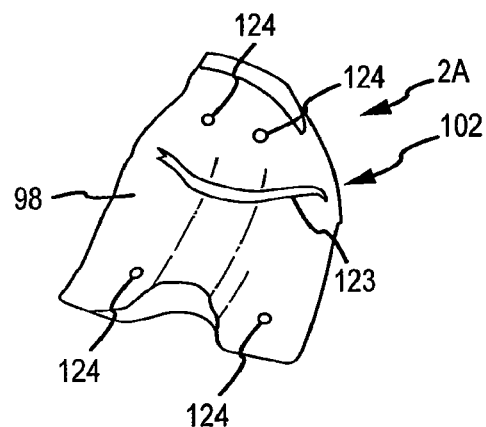
FIGS. 2A and 2B are, respectively, bottom and top perspective views of an example customized arthroplasty femur jig.
Figure 2B:
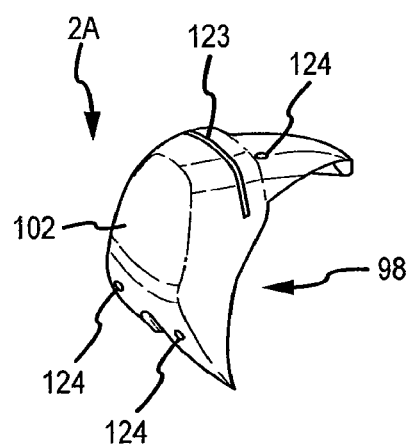
Figure 2C:
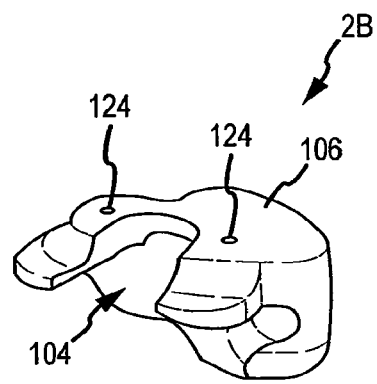
FIGS. 2C and 2D are, respectively, top/posterior and bottom/anterior perspective views of an example customized arthroplasty tibia jig.
Figure 2D:
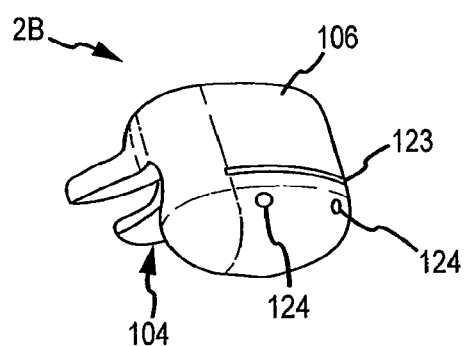

For a discussion of example customized arthroplasty cutting jigs 2 capable of being manufactured via the above-discussed process, reference is made to FIGS. 2A-2D. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 2A-2D are for total knee replacement ("TKR") or partial knee ("uni-knee") replacement procedures. Thus, FIGS. 2A and 2B are, respectively, bottom and top perspective views of an example customized arthroplasty femur jig 2A, and FIGS. 2C and 2D are, respectively, bottom and top perspective views of an example customized arthroplasty tibia jig 2B.

As indicated in FIGS. 2A and 2B, a femur arthroplasty jig 2A may include an interior side or portion 98 and an exterior side or portion 102. When the femur cutting jig 2A is used in a TKR procedure, the interior side or portion 98 faces and matingly receives the arthroplasty target area 42 of the femur lower end, and the exterior side or portion 102 is on the opposite side of the femur cutting jig 2A from the interior portion 98.

The interior portion 98 of the femur jig 2A is configured to match the surface features of the damaged lower end (i.e., the arthroplasty target area 42) of the patient's femur 18. Thus, when the target area 42 is received in the interior portion 98 of the femur jig 2A during the TKR surgery, the surfaces of the target area 42 and the interior portion 98 match.

The surface of the interior portion 98 of the femur cutting jig 2A is machined or otherwise formed into a selected femur jig blank 50A and is based or defined off of a 3D surface model 40 of a target area 42 of the damaged lower end or target area 42 of the patient's femur 18.

As indicated in FIGS. 2C and 2D, a tibia arthroplasty jig 2B may include an interior side or portion 104 and an exterior side or portion 106. When the tibia cutting jig 2B is used in a TKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20.

While the discussion provided herein is given in the context of TKR and TKR jigs and the generation thereof, the disclosure provided herein is readily applicable to uni-compartmental or partial arthroplasty procedures in the knee or other joint contexts. Thus, the disclosure provided herein should be considered as encompassing jigs and the generation thereof for both total and uni-compartmental arthroplasty procedures.

The remainder of this Detailed Discussion will now focus on various embodiments for performing POP.

B. Overview of Preoperative Planning ("POP") Procedure

In one embodiment, as can be understood from [blocks 100-110] of FIGS. 1B-1C2, medical images 16 of the femur and tibia 18, 20 are generated [Blocks 100 and 105] and coronal, axial and sagittal image slices are analyzed to determine reference data 28, 100, 900. [Block 115]. The sizes of the implant models 34 are selected relative to the femur and tibia reference data. [Block 112, 114 and 121, 122]. The reference data 28, 100, 900 is utilized with the data associated with implant models 34 to determine the cut plane location. The joint spacing between the femur and the tibia is determined. An adjustment value tr is determined to account for cartilage thickness or joint gap of a restored joint. The implant models 34 are shifted or adjusted according to the adjustment value tr [blocks 118 and 123]. Two dimensional computer implant models 34 are rendered into the two dimensional imaging slice(s) of the bones 28 such that the 2D implant models 34 appear alongside the 2D imaging slices of the bones 28. In one embodiment, ITK software, manufactured by Kitware, Inc. of Clifton Park, N.Y. is used to perform this rendering. Once the 2D implant models 34 are rendered into the MRI/CT image, the proper selection, orientation and position of the implant models can be verified. An additional verification process may be used wherein 3D models of the bones and implants are created and proper positioning of the implant may be verified. Two dimensional computer models 34 and three dimensional computer models 1004, 1006 of the femur and tibia implants are generated from engineering drawings of the implants and may be generated via any of the above-referenced 2D and 3D modeling programs to confirm planning. If the implant sizing is not correct, then the planning will be amended by further analysis of the 2D images. If the implant sizing is accurate, then planning is complete. The process then continues as indicated in [block 125] of FIG. 11E.

This ends the overview of the POP process. The following discussions will address each of the aspects of the POP process in detail.

C. Femur and Tibia Images

Figure 3A:
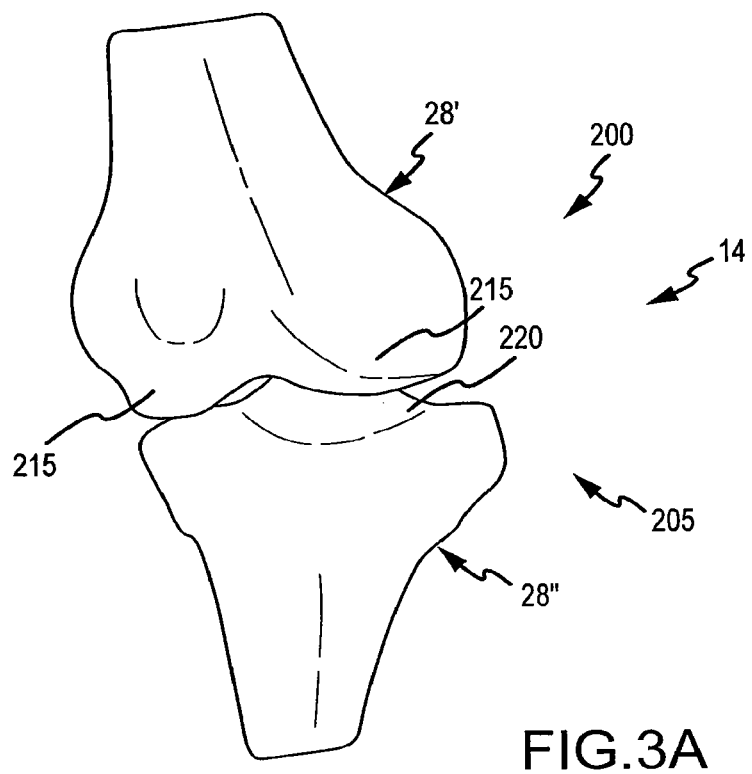
FIG. 3A is an isometric view of a 3D computer model of a femur lower end and a 3D computer model of a tibia upper end in position relative to each to form a knee joint and representative of the femur and tibia in a non-degenerated state.

FIG. 3A depicts 2D bone models or images 28', 28" of the femur and tibia 18, 20 from medical imaging scans 16. While FIG. 3A represents the patient's femur 18 and tibia 20 prior to injury or degeneration, it can be understood that, in other embodiments, the images 28', 28" may also represent the patient's femur 18 and tibia 20 after injury or degeneration. More specifically, FIG. 3A is a 2D image slice 28' of a femur lower end 200 and an 2D image slice 28" of a tibia upper end 205 representative of the corresponding patient bones 18, 20 in a non-deteriorated state and in position relative to each to form a knee joint 14. The femur lower end 200 includes condyles 215, and the tibia upper end 205 includes a plateau 220. The images or models 28', 28" are positioned relative to each other such that the curved articular surfaces of the condyles 215, which would normally mate with complementary articular surfaces of the plateau 220, are instead not mating, but roughly positioned relative to each other to generally approximate the knee joint 14.

As generally discussed above with respect to FIGS. 1A-1C2, the POP begins by using a medical imaging process, such as magnetic resonance imaging (MRI), computed tomography (CT), and/or another other medical imaging process, to generate imaging data of the patient's knee. For example, current commercially available MRI machines use 8 bit (255 grayscale) to show the human anatomy. Therefore, certain components of the knee, such as the cartilage, cortical bone, cancellous bone, meniscus, etc., can be uniquely viewed and recognized with 255 grayscale. The generated imaging data is sent to a preoperative planning computer program. Upon receipt of the data, a user or the computer program may analyze the data (e.g., two-dimensional MRI images 16, and more specifically, the 2D femur image(s) 28' or 2D tibia image(s) 28") to determine various reference points, reference lines and reference planes. In one embodiment, the MRI imaging scans 16 may be analyzed and the reference data for POP may be generated by a proprietary software program called PerForm.

For greater detail regarding the methods and systems for computer modeling joint bones, such as the femur and tibia bones forming the knee, please see the following U.S. patent applications, which are all incorporated herein in their entireties: U.S. patent application Ser. No. 11/656,323 to Park et al., titled "Arthroplasty Devices and Related Methods" and filed Jan. 19, 2007, now U.S. Pat. No. 9,017,336; U.S. patent application Ser. No. 10/146,862 to Park et al., titled "Improved Total Joint Arthroplasty System" and filed May 15, 2002; U.S. patent Ser. No. 11/642,385 to Park et al., titled "Arthroplasty Devices and Related Methods" and filed Dec. 19, 2006.

Figure 3B:
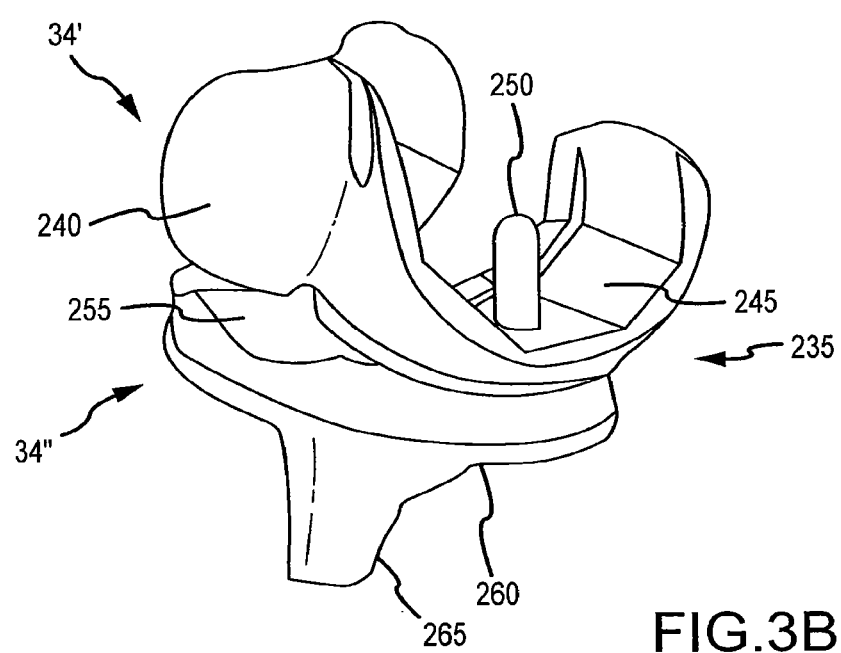
FIG. 3B is an isometric view of a 3D computer model of a femur implant and a 3D computer model of a tibia implant in position relative to each to form an artificial knee joint.

FIG. 3B is an isometric view of a computer model of a femur implant 34' and a computer model of a tibia implant 34" in position relative to each to form an artificial knee joint 14. The computer models 34', 34" may be formed, for example, via computer aided drafting or 3D modeling programs. As will be discussed later in this detailed description, the implant computer models may be in 2D or in 3D as necessary for the particular planning step.

The femur implant model 34' will have a joint side 240 and a bone engaging side 245. The joint side 240 will have a condyle-like surface for engaging a complementary surface of the tibia implant model 34". The bone engaging side 245 will have surfaces and engagement features 250 for engaging the prepared (i.e., sawed to shape) lower end of the femur 18.

The tibia implant model 34" will have a joint side 255 and a bone engaging side 260. The joint side 255 will have a plateau-like surface configured to engage the condyle-like surface of the femur implant model 34'. The bone engaging side 260 will have an engagement feature 265 for engaging the prepared (i.e., sawed to shape) upper end of the tibia 20.

As discussed in the next subsections of this Detailed Description, the reference data of the femur and tibia bone models or images 28', 28" may be used in conjunction with the implant models 34', 34" to select the appropriate sizing for the implants actually to be used for the patient. The resulting selections can then be used for planning purposes, as described later in this Detailed Description.

D. Femur Planning Process

For a discussion of the femur planning process, reference is now made to FIGS. 4-22. FIGS. 4-9 illustrate a process in the POP wherein the system 4 utilizes 2D imaging slices (e.g., MRI slices, CT slices, etc.) to determine femur reference data, such as reference points, lines and planes via their relationship to the trochlear groove plane-GHO of the femur. The resulting femur reference data 100 is then mapped or projected to a y-z coordinate system (sagittal plane). The femur reference data is then applied to a candidate femur implant model, resulting in femoral implant reference data 100'. The data 100, 100' is utilized to select an appropriate set of candidate implants, from which a single candidate implant will be chosen, which selection will be discussed in more detail below with reference to FIGS. 10-22.

1. Determining Femur Reference Data

Figure 4:
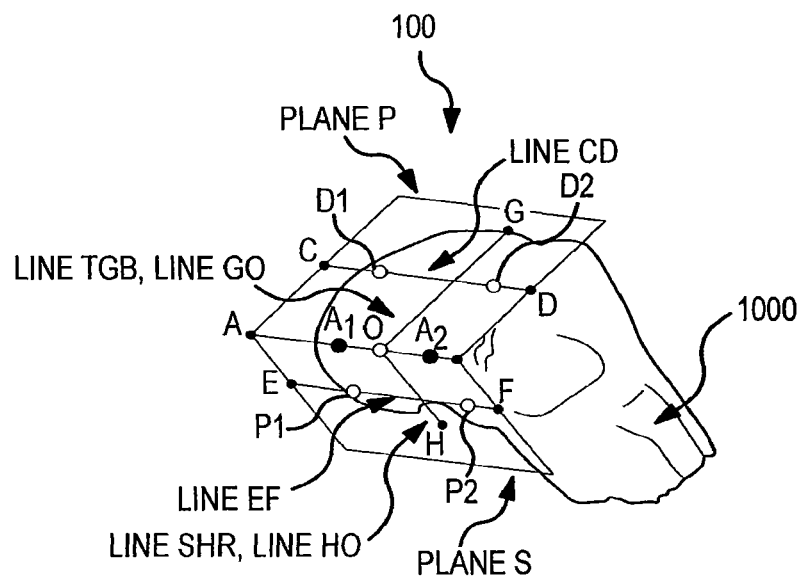
FIG. 4 is a perspective view of the distal end of 3D model of the femur wherein the femur reference data is shown.

For a discussion of a process used to determine the femur reference data, reference is now made to FIGS. 4-7C. FIG. 4 is a perspective view of the distal end of a 3D model 1000 of the femur image of FIG. 3A wherein the femur reference data 100 is shown. As will be explained in more detail below, the femur reference data is generated by an analysis of the 2D image scans and FIG. 4 depicts the relative positioning of the reference data on a 3D model. As shown in FIG. 4, the femur reference data 100 may include reference points (e.g. $D_1$, $D_2$), reference lines (e.g. GO, EF) and reference planes (e.g. P, S). The femur reference data 100 may be determined by a process illustrated in FIGS. 5A-7D and described in the next sections.

Figure 5A:
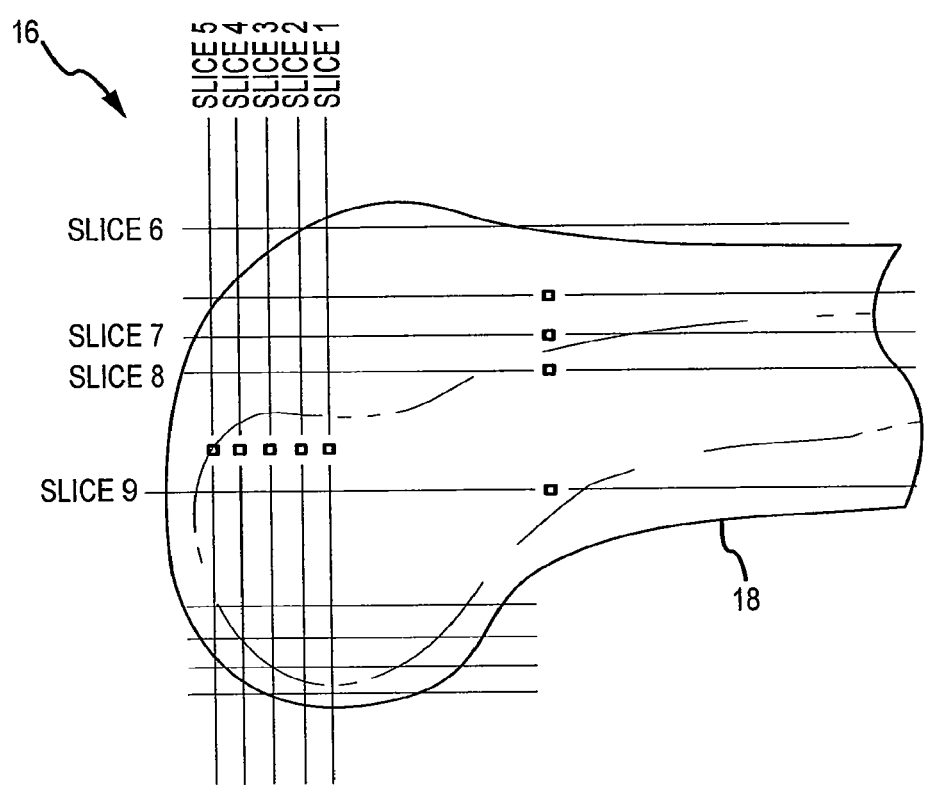
FIG. 5A is a sagittal view of a femur illustrating the orders and orientations of imaging slices utilized in the femur POP.
Figure 5B:
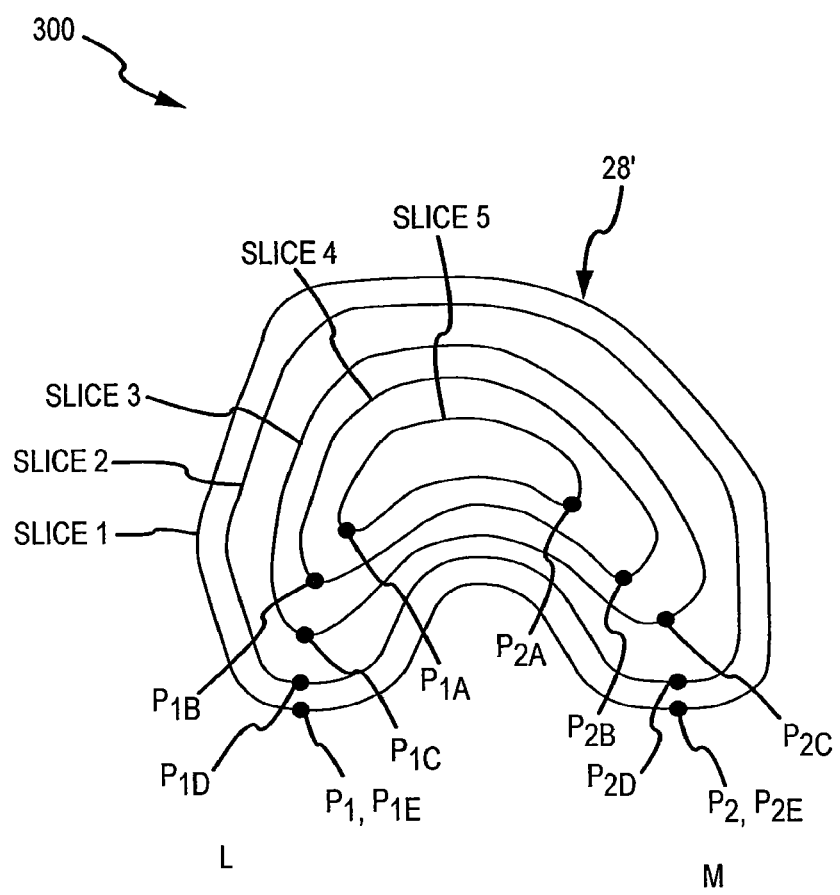
FIG. 5B depicts axial imaging slices taken along section lines of the femur of FIG. 5A.
Figure 5C:
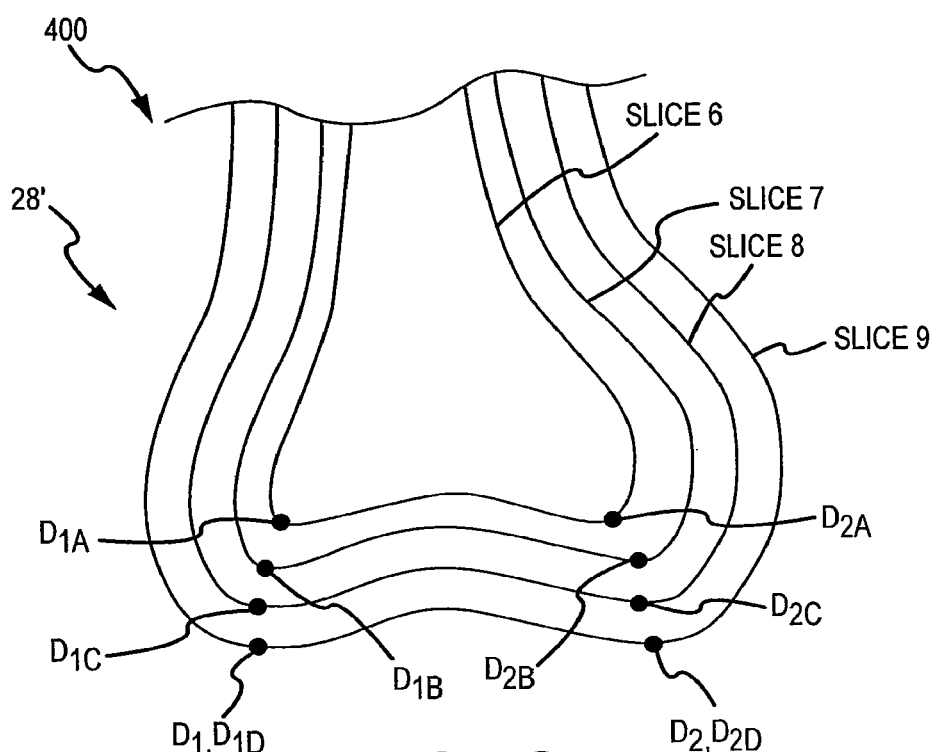
FIG. 5C depicts coronal imaging slices taken along section lines of the femur of FIG. 5A.

As shown in FIG. 5A, which is a sagittal view of a femur 18 illustrating the orders and orientations of imaging slices 16 that are utilized in the femur POP, a multitude of image slices may be compiled. In some embodiments, the image slices may be analyzed to determine, for example, distal contact points prior to or instead of being compiled into a bone model. Image slices may extend medial-lateral in planes that would be normal to the longitudinal axis of the femur, such as image slices 1-5 of FIGS. 5A and 6D. Image slices may extend medial-lateral in planes that would be parallel to the longitudinal axis of the femur, such as image slices 6-9 of FIGS. 5A and 7B. The number of image slices may vary from 1-50 and may be spaced apart in a 2 mm spacing or other spacing.

a. Determining Reference Points $P_1P_2$

In some embodiments, the planning process begins with the analysis of the femur slices in a 2D axial view. As can be understood from FIG. 5B, which depicts axial imaging slices of FIG. 5A, the series of 2D axial femur slices are aligned to find the most posterior point of each condyle. For example, the most posterior points of slice 5, $P_{1A}$, $P_{2A}$, are compared to the most posterior points of slice 4, $P_{1B}$, $P_{2B}$. The most posterior points of slice 4 are more posterior than those of slice 5. Therefore, the points of slice 4 will be compared to slice 3. The most posterior points of slice 3, $P_{1C}$, $P_{2C}$, are more posterior than the posterior points $P_{1B}$, $P_{2B}$ of slice 4. Therefore, the points of slice 3 will be compared to slice 2. The most posterior points of slice 2, $P_{1D}$, $P_{2D}$, are more posterior than the posterior points $P_{1C}$, $P_{2C}$ of slice 3. Therefore, the points of slice 2 will be compared to slice 1. The most posterior points of slice 1, $P_{1E}$, $P_{2E}$, are more posterior than the posterior points $P_{1D}$, $P_{2D}$ of slice 2. In some embodiments, the points of slice 1 may be compared to slice 0 (not shown). The most posterior points of slice 0, $P_{1F}$, $P_{2F}$, are less posterior than the posterior points $P_{1E}$, $P_{2E}$ of slice 1. Therefore, the points of slice 1 are determined to be the most posterior points $P_1P_2$ of the femur. In some embodiments, points $P_1$ and $P_2$ may be found on different axial slices. That is, the most posterior point on the medial side and most posterior point on the lateral side may lie in different axial slices. For example, slice 2 may include the most posterior point on the lateral side, while slice 1 may include the most posterior point on the medial side. It can be appreciated that the number of slices that are analyzed as described above may be greater than five slices or less than five slices. The points $P_1$, $P_2$ are stored for later analysis.

b. Determining Reference Points $D_1$, $D_2$

The planning process continues with the analysis of the femur slices in a 2D coronal view. As can be understood from FIG. 5C, which depicts coronal imaging slices of FIG. 5A, the series of 2D coronal femur slices are aligned to find the most distal point of each condyle. For example, the most distal points of slice 6, $D_{1A}$, $D_{2A}$, are compared to the most distal points of slice 7, $D_{1B}$, $D_{2B}$. The most distal points of slice 7 are more distal than those of slice 6. Therefore, the points of slice 7 will be compared to slice 8. The most distal points of slice 8, $D_{1C}$, $D_{2C}$, are more distal than the distal points $D_{1B}$, $D_{2B}$ of slice 7. Therefore, the points of slice 8 will be compared to slice 9. The most distal points of slice 9, $D_{1D}$, $D_{2D}$, are more distal than the distal points $D_{1C}$, $D_{2C}$ of slice 8. In some embodiments, the points of slice 9 may be compared to slice 10 (not shown). The most distal points of slice 10, $D_{1E}$, $D_{2E}$, are less distal than the distal points $D_{1D}$, $D_{2D}$ of slice 9. Therefore, the points of slice 9 are determined to be the most distal points $D_1$, $D_2$ of the femur. In some embodiments, points $D_1$ and $D_2$ may be found on different coronal slices. That is, the most distal point on the medial side and most distal point on the lateral side may lie in different coronal slices. For example, slice 9 may include the most distal point on the lateral side, while slice 8 may include the most distal point on the medial side. It can be appreciated that the number of slices that are analyzed as described above may be greater than four slices or less than four slices. The points $D_1$, $D_2$ are stored for future analysis.

c. Determining Reference Lines CD and GO

Figure 6A:
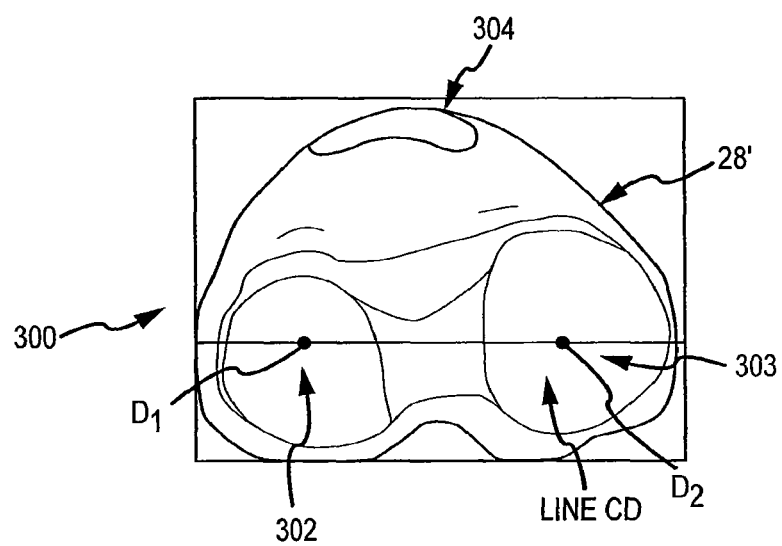
FIG. 6A is an axial imaging slice taken along section lines of the femur of FIG. 5A, wherein the distal reference points are shown.

Analysis of the 2D slices in the axial view aid in the determination of internal/external rotation adjustment. The points $D_1$, $D_2$ represent the lowest contact points of each of the femoral lateral and medial condyles 302, 303. Thus, to establish an axial-distal reference line, line CD, in 2D image slice(s), the analysis utilizes the most distal point, either $D_1$ or $D_2$, from the undamaged femoral condyle. For example, as shown in FIG. 6A, which is an axial imaging slice of the femur of FIG. 5A, when the lateral condyle 302 is undamaged but the medial condyle 303 is damaged, the most distal point $D_1$ will be chosen as the reference point in establishing the axial-distal reference line, line CD. The line CD is extended from the lateral edge of the lateral condyle, through point $D_1$, to the medial edge of the medial condyle. If the medial condyle was undamaged, then the distal point $D_2$ would be used as the reference point through which line CD would be extended. The distal points $D_1$, $D_2$ and line CD are stored for later analysis.

A line CD is verified. A most distal slice of the series of axial views is chosen to verify the position of an axial-distal reference line, line CD. As shown in FIG. 6A, the most distal slice 300 of the femur (e.g., slice 5 in FIGS. 5A and 6D) is chosen to position line CD such that line CD is generally anteriorly-posteriorly centered in the lateral and medial condyles 302, 303. Line CD is generally aligned with the cortical bone of the undamaged posterior condyle. For example, if the medial condyle 303 is damaged, the line CD will be aligned with the undamaged lateral condyle, and vice versa. To verify the location of line CD and as can be understood from FIGS. 4 and 6C, the line CD will also connect the most distal points $D_1$, $D_2$. The geography information of line CD will be stored for future analysis.

Line GO is determined. The "trochlear groove axis" or the "trochlear groove reference plane" is found. In the knee flexion/extension motion movement, the patella 304 generally moves up and down in the femoral trochlear groove along the vertical ridge and generates quadriceps forces on the tibia. The patellofemoral joint and the movement of the femoral condyles play a major role in the primary structure and mechanics across the joint. In a normal knee model or properly aligned knee, the vertical ridge of the posterior patella is generally straight (vertical) in the sliding motion. For the OA patients' knees, there is rarely bone damage in the trochlear groove; there is typically only cartilage damage. Therefore, the trochlear groove of the distal femur can serve as a reliable bone axis reference. In relation to the joint line assessment, as discussed with reference to FIGS. 14A-14J, the trochlear groove axis of the distal femur is perpendicular or nearly perpendicular to the joint line of the knee. A detailed discussion of the trochlear groove axis or the trochlear groove reference plane may be found in co-owned U.S. patent application Ser. No. 12/111,924, now U.S. Pat. No. 8,480,679, which is incorporated by reference in its entirety.

Figure 6B:
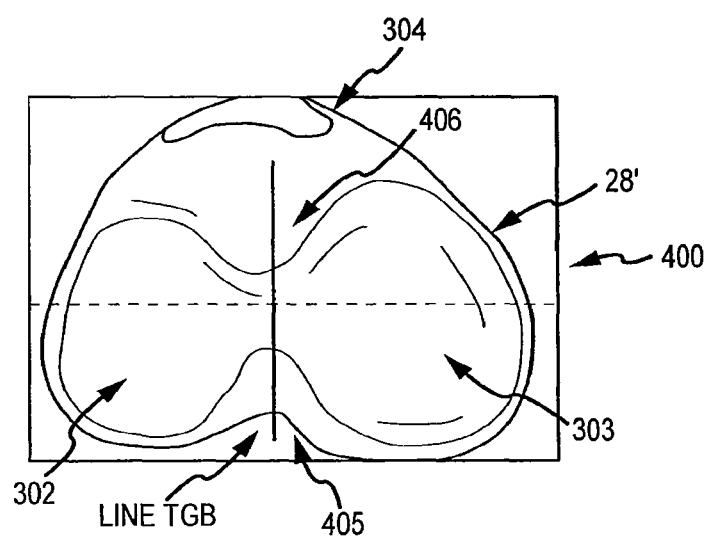
FIG. 6B is an axial imaging slice taken along section lines of the femur of FIG. 5A, wherein the trochlear groove bisector line is shown.
Figure 6C:
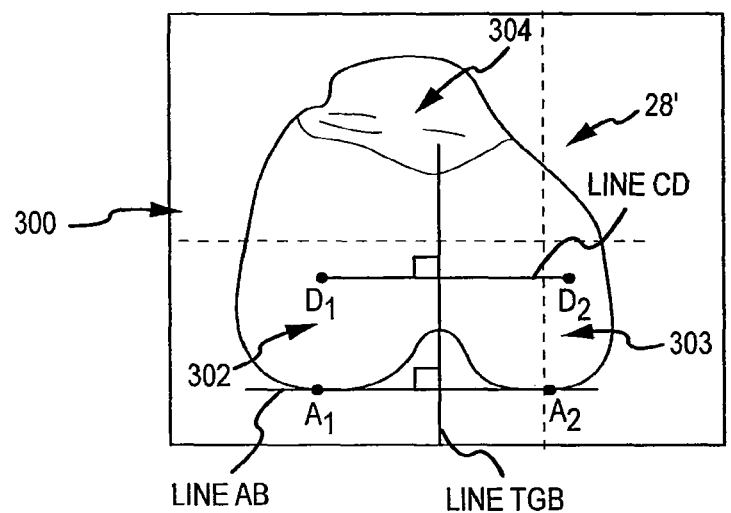
FIG. 6C is an axial imaging slice taken along section lines of the femur of FIG. 5A, wherein the femur reference data is shown.
Figure 6D:
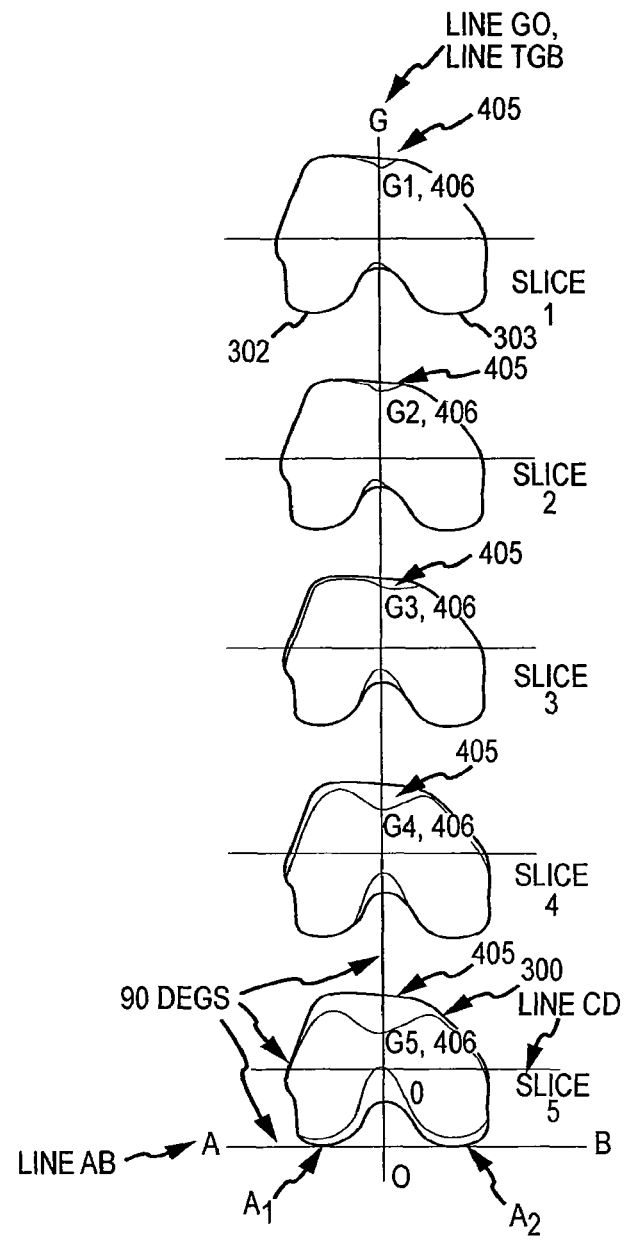
FIG. 6D is the axial imaging slices taken along section lines of the femur in FIG. 5A.

To perform the trochlear groove analysis, the MRI slice in the axial view with the most distinct femoral condyles (e.g., the slice with the largest condyles such as slice 400 of FIG. 6B) will be chosen to position the trochlear groove bisector line, line TGB. As shown in FIG. 6B, which is an axial imaging slice of the femur of FIG. 5A, the most distinct femoral condyles 302, 303 are identified. The trochlear groove 405 is identified from image slice 400. The lowest extremity 406 of the trochlear groove 405 is then identified. Line TGB is then generally aligned with the trochlear groove 405 across the lowest extremity 406. In addition, and as shown in FIG. 6D, which is the axial imaging slices 1-5 taken along section lines 1-5 of the femur in FIG. 5A, each of the slices 1-5 can be aligned vertically along the trochlear groove 405, wherein points G1, G2, G3, G4, G5 respectively represent the lowest extremity 406 of trochlear groove 405 for each slice 1-5. By connecting the various points G1, G2, G3, G4, G5, a point O can be obtained. As can be understood from FIGS. 4 and 6C, resulting line GO is perpendicular or nearly perpendicular to line $D_1D_2$. In a 90° knee extension, line GO is perpendicular or nearly perpendicular to the joint line of the knee and line $P_1P_2$. Line GO is stored for later analysis.

d. Determining Reference Lines EF and HO

Figure 7A:
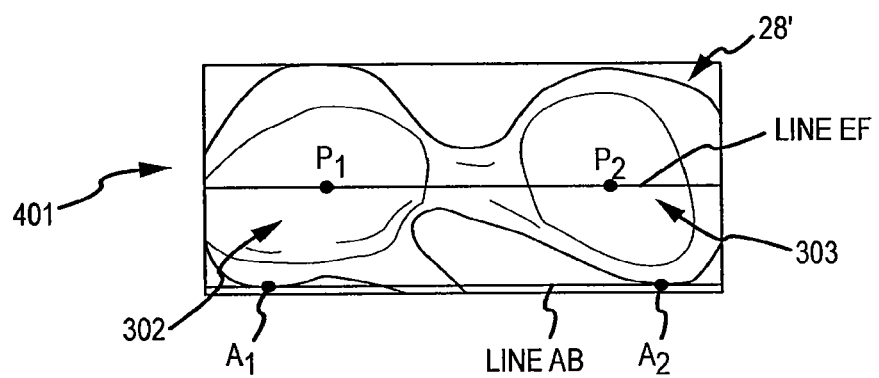
FIG. 7A is a coronal slice taken along section lines of the femur of FIG. 5A, wherein the femur reference data is shown

Analysis of the 2D slices in the coronal view aid in the determination of femoral varus/valgus adjustment. The points $P_1$, $P_2$ determined above represent the most posterior contact points of each of the femoral lateral and medial condyles 302, 303. Thus, to establish a coronal posterior reference line, line EF, in 2D image slice(s), the analysis utilizes the most posterior point, either $P_1$ or $P_2$, from the undamaged femoral condyle. For example, as shown in FIG. 7A, when the lateral condyle 302 is undamaged but the medial condyle 303 is damaged, the most posterior point $P_1$ will be chosen as the reference point in establishing the coronal posterior reference line, line EF. The line EF is extended from the lateral edge of the lateral condyle, through point $P_1$, to the medial edge of the medial condyle. If the medial condyle was undamaged, then the posterior point $P_2$ would be used as the reference point through which line EF would be extended. The posterior points $P_1$, $P_2$ and line EF are stored for later analysis.

The points, $P_1P_2$ were determined as described above with reference to FIG. 5B. Line EF is then verified. A most posterior slice of the series of coronal views is chosen to verify the position of a coronal posterior reference line, line EF. As shown in FIG. 7A, which is a coronal imaging slice of FIG. 5A, the most posterior slice 401 of the femur (e.g., slice 6 in FIGS. 5A and 7B) is chosen to position line EF such that line EF is generally positioned in the center of the lateral and medial condyles 302, 303. Line EF is generally aligned with the cortical bone of the undamaged posterior condyle. For example, if the medial condyle 303 is damaged, the line EF will be aligned with the undamaged lateral condyle, and vice versa. To verify the location of line EF and as can be understood from FIG. 4, the line EF will also connect the most posterior points $P_1$, $P_2$. The geography information of line EF will be stored for future analysis.

Figure 7B:
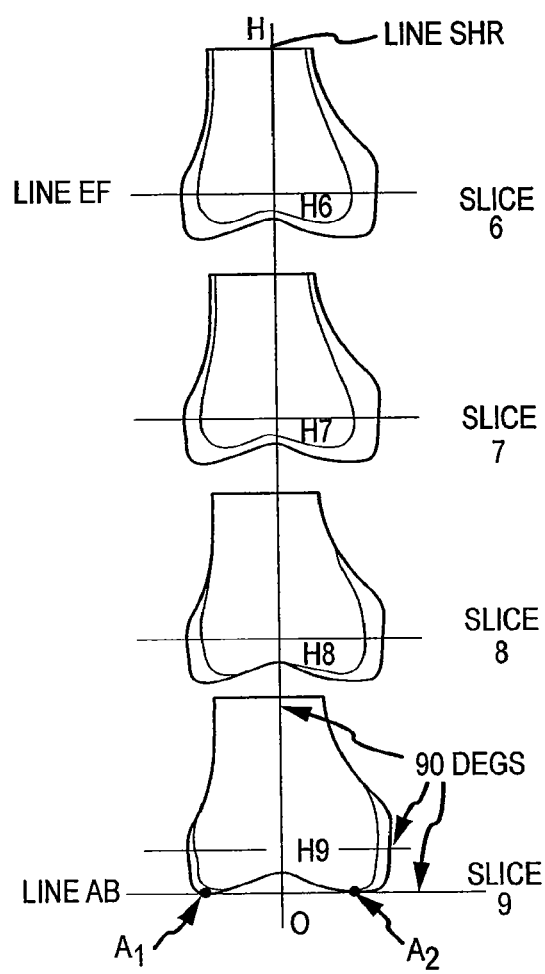
FIG. 7B is the coronal imaging slices taken along section lines of the femur in FIG. 5A.

In some embodiments, line HO may be determined. As shown in FIG. 7B, which are coronal imaging slices 6-9 taken along section lines 6-9 of the femur in FIG. 5A, each of the image slices 6-9 taken from FIG. 5A can be aligned along the trochlear groove. The points H6, H7, H8, H9 respectively represent the lowest extremity of the trochlear groove for each of the image slices 6-8 from FIG. 5A. By connecting the various points H6, H7, H8, the point O can again be obtained. The resulting line HO is established as the shaft reference line-line SHR. The coronal-posterior reference line, line EF and coronal-distal reference line, line AB may be adjusted to be perpendicular or nearly perpendicular to the shaft reference line-line SHR (line HO). Thus, the shaft reference line, line SHR (line HO) is perpendicular or nearly perpendicular to the coronal-posterior reference line, line EF and to the coronal-distal reference line, line AB throughout the coronal image slices.

As can be understood from FIGS. 4 and 7B, the trochlear groove plane-GHO, as the reference across the most distal extremity of the trochlear groove of the femur and in a 90° knee extension, should be perpendicular to line AB. The line-HO, as the reference across the most posterior extremity of trochlear groove of the femur and in a 0° knee extension, should be perpendicular to line AB.

e. Determining Reference Line AB and Reference Planes P and S

As can be understood from FIG. 4, a posterior plane S may be constructed such that the plane S is normal to line GO and includes posterior reference points $P_1$, $P_2$. A distal plane P may be constructed such that it is perpendicular to posterior plane S and may include distal reference points $D_1$, $D_2$ (line CD). Plane P is perpendicular to plane S and forms line AB therewith. Line HO and line GO are perpendicular or nearly perpendicular to each other. Lines CD, AB and EF are parallel or nearly parallel to each other. Lines CD, AB and EF are perpendicular or nearly perpendicular to lines HO and GO and the trochlear plane GHO.

f. Verification of the Femoral Reference Data

Figure 7C:
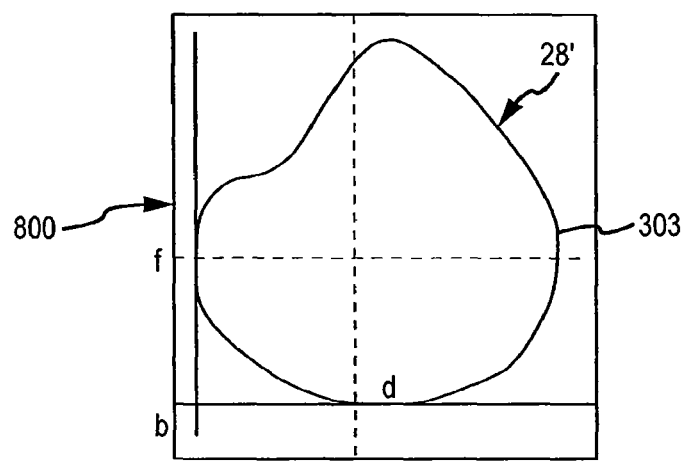
FIG. 7C is a sagittal imaging slice of the femur in FIG. 5A.

As shown in FIG. 7C, which is an imaging slice of the femur of FIG. 5A in the sagittal view, after the establishment of the reference lines from the axial and coronal views, the axial-distal reference line CD and coronal-posterior reference line EF and planes P, S are verified in the 2D sagittal view. The sagittal views provide the extension/flexion adjustment. Thus, as shown in FIG. 7C, slice 800 shows a sagittal view of the femoral medial condyle 303. Line-bf and line-bd intersect at point-b. As can be understood from FIGS. 4 and 7C, line-bf falls on the coronal plane-S, and line-bd falls on the axial plane-P. Thus, in one embodiment of POP planning, axial and coronal views are used to generate axial-distal and coronal-posterior reference lines CD, EF. These two reference lines CD, EF can be adjusted (via manipulation of the reference data once it has been imported and opened on the computer) to touch in the black cortical rim of the femur. The adjustment of the two reference lines on the femur can also be viewed simultaneously in the sagittal view of the MRI slice, as displayed in FIG. 7C. Thus, the sagittal view in FIG. 7C provides one approach to verify if the two reference lines do touch or approximately touch with the femur cortical bone. In some embodiments, line-bf is perpendicular or nearly perpendicular to line-bd. In other embodiments, line bf may not be perpendicular to bd. This angle depends at least partially on the rotation of femoral bone within MRI.

With reference to FIGS. 4-7C, in one embodiment, lines HO and GO may be within approximately six degrees of being perpendicular with lines $P_1P_2$, $D_1D_2$ and $A_1A_2$ or the preoperative planning for the distal femur will be rejected and the above-described processes to establish the femoral reference data 100 (e.g. reference lines CD, EF, AB, reference points $P_1P_2$, $D_1D_2$) will be repeated until the femoral reference data meets the stated tolerances, or a manual segmentation for setting up the reference lines will be performed. In other embodiments, if there are multiple failed attempts to provide the reference lines, then the reference data may be obtained from another similar joint that is sufficiently free of deterioration. For example, in the context of knees, if repeated attempts have been made without success to determined reference data in a right knee medial femur condyle based on data obtained from the right knee lateral side, then reference data could be obtained from the left knee lateral or medial sides for use in the determination of the femoral reference data.

g. Mapping the Femoral Reference Data to a Y-Z Plane

Figure 7D:
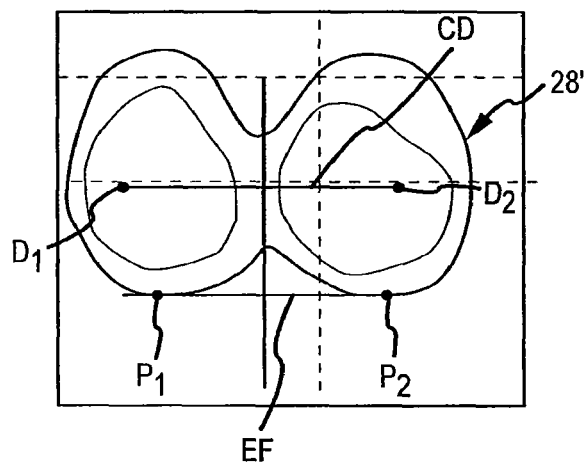
FIG. 7D is an axial imaging slice taken along section lines of the femur of FIG. 5A, wherein the femur reference data is shown.
Figure 7E:
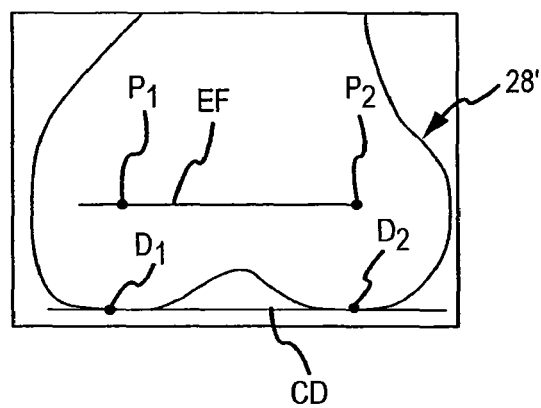
FIG. 7E is a coronal imaging slice taken along section lines of the femur of FIG. 5A, wherein the femur reference data is shown.

As can be understood from FIGS. 7D-9, the femoral reference data 100 will be mapped to a y-z coordinate system to aid in the selection of an appropriate implant. As shown in FIGS. 7D-7E, which are axial and coronal slices, respectively, of the femur, the points $D_1D_2$ of the distal reference line $D_1D_2$ or CD were determined from both a 2D axial view and a 2D coronal view and therefore are completely defined in 3D. Similarly, the points $P_1P_2$ of the posterior reference line $P_1P_2$ or EF were determined from both a 2D axial view and a 2D coronal view and therefore are completely defined in 3D.

Figure 8:
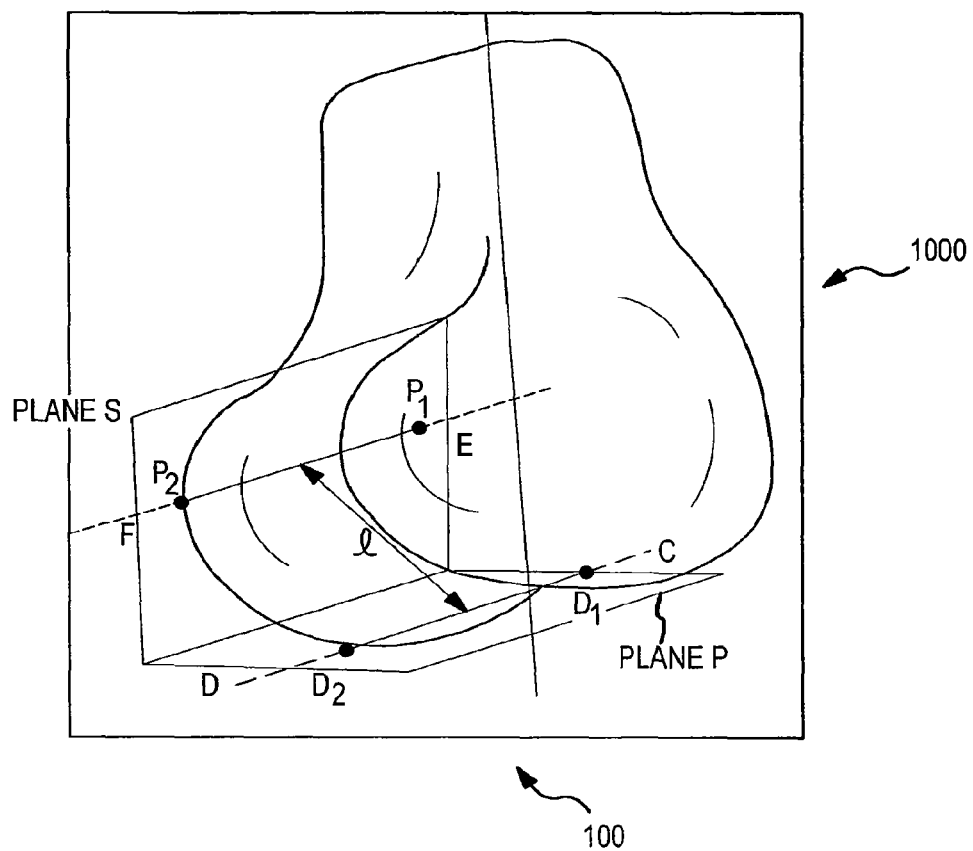
FIG. 8 is a posterior view of a 3D model of a distal femur.

As shown in FIG. 8, which is a posterior view of a femur 3D model 1000, the reference data 100 determined by an analysis of 2D images may be imported onto a 3D model of the femur for verification purposes. The distance L between line EF and line CD can be determined and stored for later analysis during the selection of an appropriate implant size.

Figure 9:
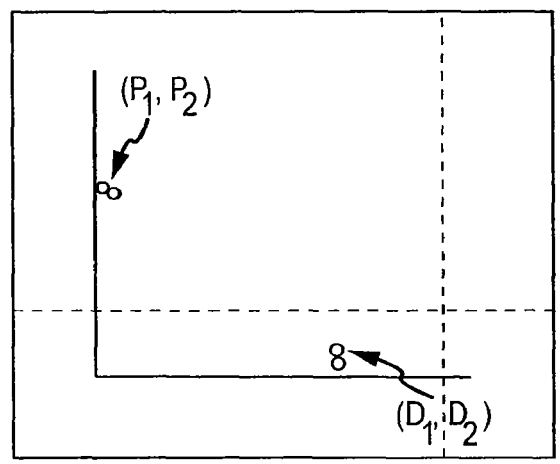
FIG. 9 depicts a y-z coordinate system wherein the femur reference data is shown.

As indicated in FIG. 9, which depicts a y-z coordinate system, the posterior points $P_1P_2$ and distal points $D_1D_2$ of the 2D images 28' may also be projected onto a y-z plane and this information is stored for later analysis.

2. Determining Femoral Implant Reference Data

Figure 10:
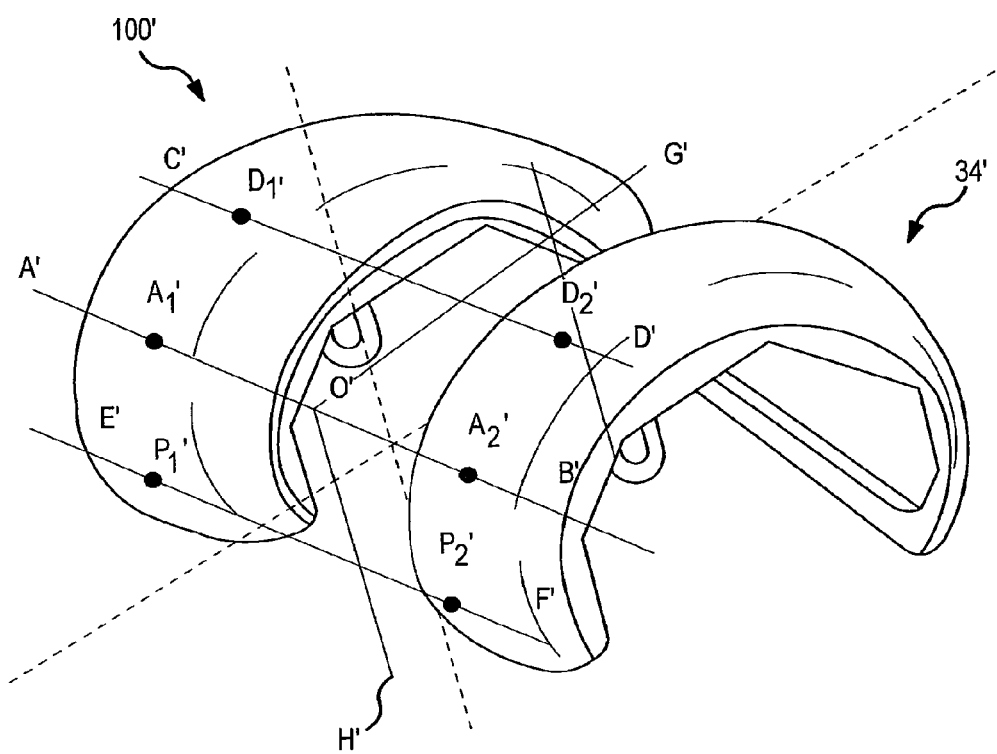
FIG. 10 is a perspective view of a femoral implant model, wherein the femur implant reference data is shown.
Figure 11:
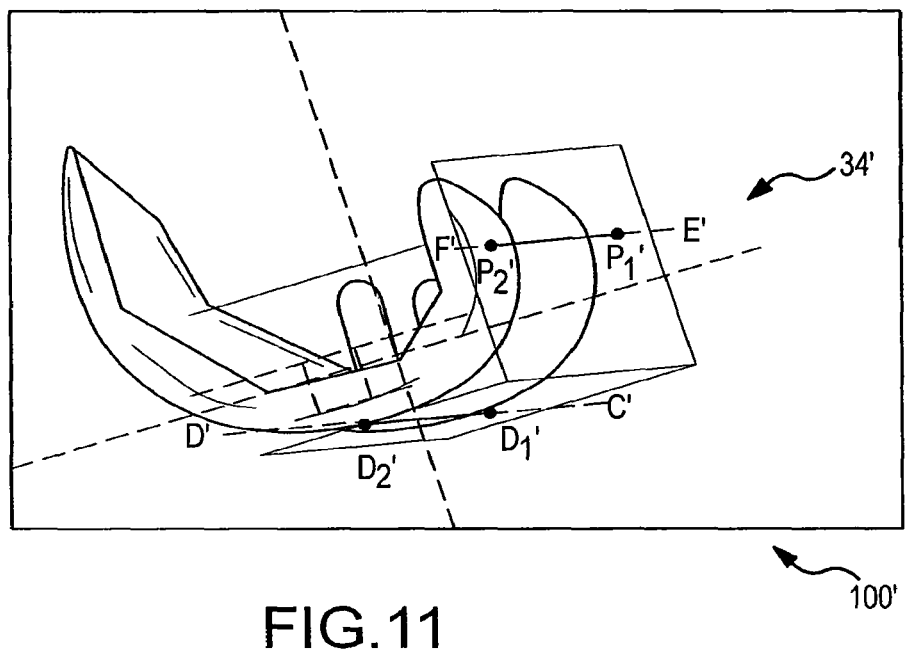
FIG. 11 is another perspective view of a femoral implant model, wherein the femur implant reference data is shown.

There are 6 degrees of freedom for a femoral implant to be moved and rotated for placement on the femoral bone. The femur reference data 100 (e.g. points $P_1P_2$, $D_1D_2$, reference lines EF, CD, reference planes P, S) is utilized in the selection and placement of the femoral implant. For a discussion of a process used to determine the implant reference data, reference is now made to FIGS. 10-22.

a. Map Femur Reference Data to Implant Model to Establish Femoral Implant Reference Data As shown in FIGS. 10 and 11, which are perspective views of a femoral implant model 34', the femur reference data 100 may be mapped to a 3D model of the femur implant model 34' in a process of POP. The femur reference data 100 and the femur implant model 34' are opened together. The femur implant model 34' is placed on a 3D coordinate system and the data 100 is also transferred to that coordinate system thereby mapping the data 100 to the model 34' to create femoral implant data 100'. The femoral implant data 100' includes an axial-distal reference line (line-C'D') and a coronal-posterior reference line (line-E'F').

As can be understood from FIGS. 10 and 11, distal line-$D_1'D_2'$ represents the distance between the two most distal points $D_1'$, $D_2'$. Posterior line-$P_1'P_2'$ represents the distance between the two most posterior points $P_1'$, $P_2'$. The lines-$D_1'D_2'P_1'P_2'$ of the implant model 34' can be determined and stored for further analysis.

Figure 12:
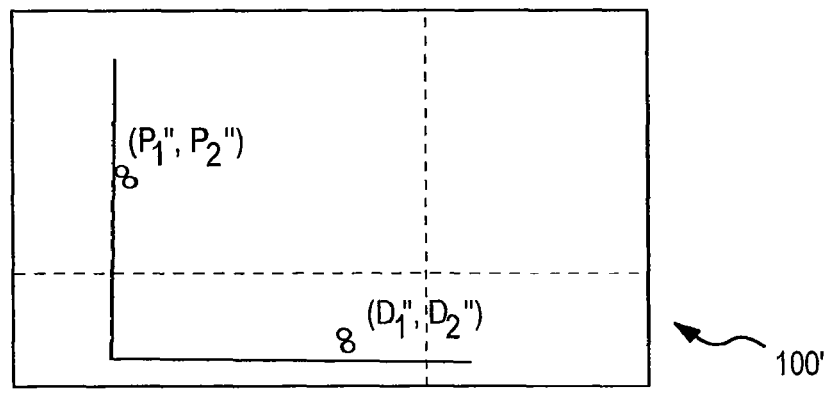
FIG. 12 is a y-z coordinate system wherein some of the femur implant reference data is shown.
Figure 13:
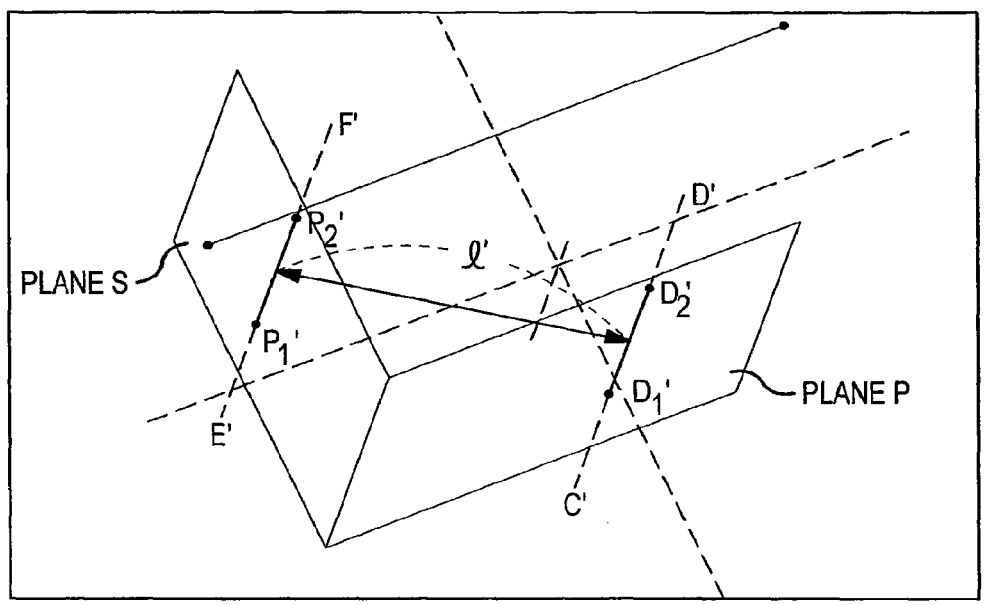
FIG. 13 is an x-y-z coordinate system wherein the femur implant reference data is shown.

As shown in FIG. 12, which shows a coordinate system wherein some of the femoral implant reference data 100' is shown, the endpoints $D_1'D_2'$ and $P_1'P_2'$ may also be projected onto a y-z plane and this information is stored for later analysis. As shown in FIG. 13, the implant reference data 100' may also be projected onto the coordinate system. The distance L' between line E'F' and line C'D', and more specifically between lines $D_1'D_2'$, $P_1'P_2'$ can be determined and stored for later use during the selection of an implant.

3. Determining Joint Line and Adjustment to Implant that Allows Condylar Surfaces of Implant Model to Restore Joint to Natural Configuration In order to allow an actual physical arthroplasty implant to restore the patient's knee to the knee's pre-degenerated or natural configuration with the natural alignment and natural tensioning in the ligaments, the condylar surfaces of the actual physical implant generally replicate the condylar surfaces of the pre-degenerated joint bone. In one embodiment of the systems and methods disclosed herein, condylar surfaces of the 2D implant model 34' are matched to the condylar surfaces of the 2D bone model or image 28'. However, because the bone model 28' may be bone only and not reflect the presence of the cartilage that actually extends over the pre-degenerated condylar surfaces, the alignment of the implant 34' may be adjusted to account for cartilage or proper spacing between the condylar surfaces of the cooperating actual physical implants (e.g., an actual physical femoral implant and an actual physical tibia implant) used to restore the joint such that the actual physical condylar surfaces of the actual physical cooperating implants will generally contact and interact in a manner substantially similar to the way the cartilage covered condylar surfaces of the pre-degenerated femur and tibia contacted and interacted. Thus, in one embodiment, the implant models are modified or positionally adjusted to achieve the proper spacing between the femur and tibia implants.

a. Determine Adjustment Value tr

To achieve the correct adjustment, an adjustment value tr may be determined. In one embodiment, the adjustment value tr may be determined in 2D by a calipers measuring tool (a tool available as part of the software). The calipers tool is used to measure joint spacing between the femur and the tibia by selection of two points in any of the 2D MRI views and measuring the actual distance between the points. In another embodiment, the adjustment value tr that is used to adjust the implant during planning may be based off of an analysis associated with cartilage thickness. In another embodiment, the adjustment value tr used to adjust the implant during planning may be based off of an analysis of proper joint gap spacing. Both the cartilage thickness and joint gap spacing methods are discussed below in turn.

i. Determining Cartilage Thickness and Joint Line

Figure 14A:
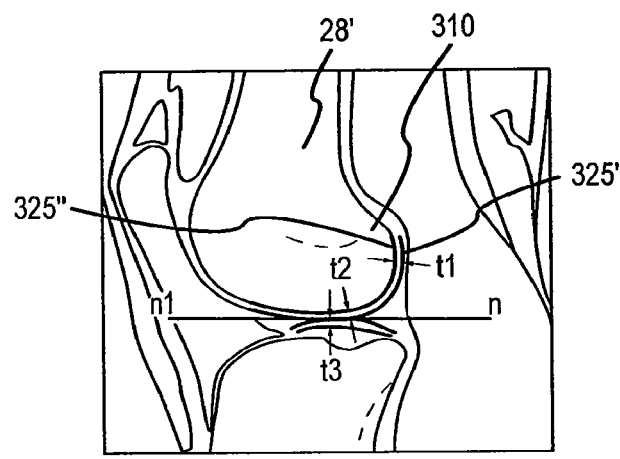
FIG. 14A shows the femoral condyle and the proximal tibia of the knee in a sagittal view MRI image slice.

FIG. 14A shows the femoral condyle 310 and the proximal tibia of the knee in a sagittal MRI image slice. The distal femur 28' is surrounded by the thin black rim of cortical bone. Due to the nature of irregular bone and cartilage loss in OA patients, it can be difficult to find the proper joint line reference for the models used during the POP.

The space between the elliptical outlining 325', 325" along the cortical bone represents the cartilage thickness of the femoral condyle 310. The ellipse contour of the femoral condyle 310 can be seen on the MRI slice shown in FIG. 14A and obtained by a three-point tangent contact spot (i.e., point t1, t2, t3) method. In a normal, healthy knee, the bone joint surface is surrounded by a layer of cartilage. Because the cartilage is generally worn-out in OA and the level of cartilage loss varies from patient to patient, it may be difficult to accurately account for the cartilage loss in OA patients when trying to restore the joint via TKA surgery. Therefore, in one embodiment of the methodology and system disclosed herein, a minimum thickness of cartilage is obtained based on medical imaging scans (e.g., MRI, etc.) of the undamaged condyle. Based on the cartilage information, the joint line reference can be restored. For example, the joint line may be line 630 in FIG. 14B.

The system and method disclosed herein provides a POP method to substantially restore the joint line back to a "normal or natural knee" status (i.e., the joint line of the knee before OA occurred) and preserves ligaments in TKA surgery (e.g., for a total knee arthroplasty implant) or partial knee arthroplasty surgery (e.g., for a uni-knee implant).

Figure 14B:
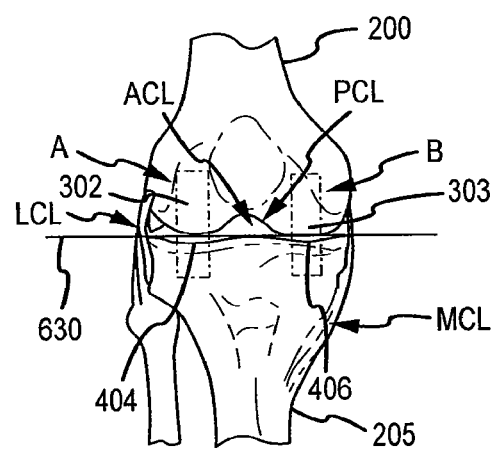
FIG. 14B is a coronal view of a knee model in extension.

FIG. 14B is a coronal view of a knee model in extension. As depicted in FIG. 14B, there are essentially four separate ligaments that stabilize the knee joint, which are the medial collateral ligament (MCL), anterior cruciate ligament (ACL), lateral collateral ligament (LCL), and posterior cruciate ligament (PCL). The MCL and LCL lie on the sides of the joint line and serve as stabilizers for the side-to-side stability of the knee joint. The MCL is a broader ligament, whereas the LCL is a distinct cord-like structure.

The ACL is located in the front part of the center of the joint. The ACL is a very important stabilizer of the femur on the tibia and serves to prevent the tibia from rotating and sliding forward during agility, jumping, and deceleration activities. The PCL is located directly behind the ACL and serves to prevent the tibia from sliding to the rear. The system and method disclosed herein provides POP that allows the preservation of the existing ligaments without ligament release during TKA surgery. Also, the POP method provides ligament balance, simplifying TKA surgery procedures and reducing pain and trauma for OA patients.

As indicated in FIG. 14B, the joint line reference 630 is defined between the two femoral condyles 302, 303 and their corresponding tibia plateau regions 404, 406. Area A illustrates a portion of the lateral femoral condyle 302 and a portion of the corresponding lateral plateau 404 of tibia 205. Area B illustrates the area of interest showing a portion of the medial femoral condyle 303 and a portion of the corresponding medial plateau 406 of tibia 205.

Figure 14C:
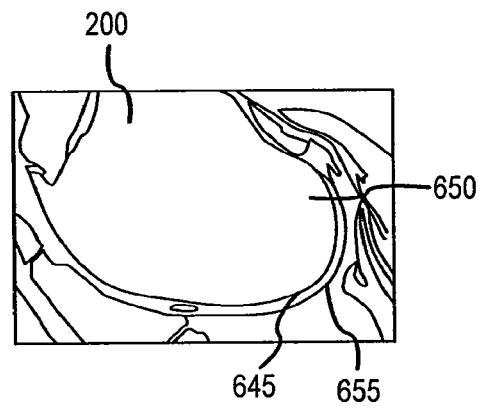
FIGS. 14C and 14D illustrate MRI segmentation slices for joint line assessment.
Figure 14D:
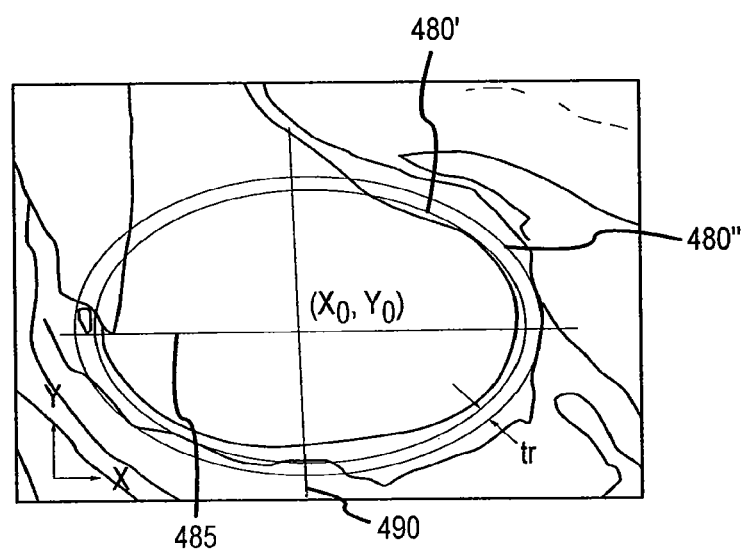
Figure 14F:
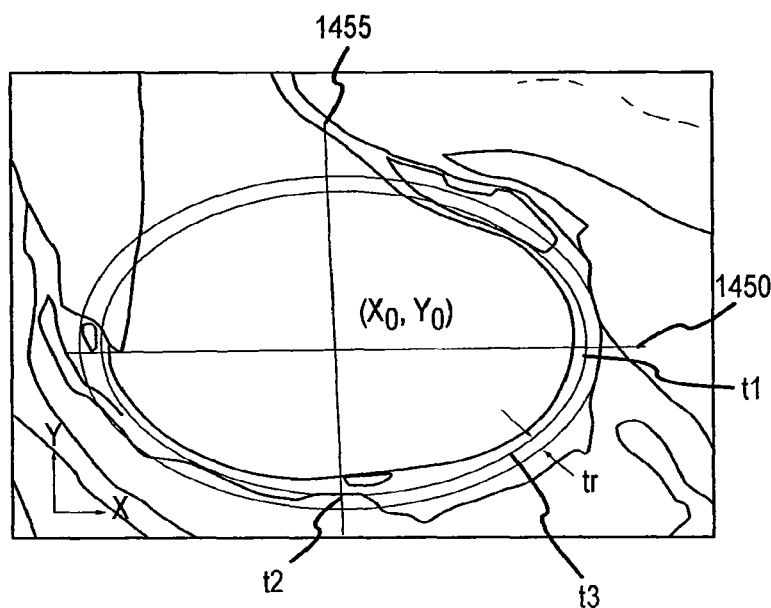
FIG. 14F illustrates a MRI segmentation slice for joint line assessment.

FIGS. 14C, 14D and 14F illustrate MRI segmentation slices for joint line assessment. FIG. 14E is a flow chart illustrating the method for determining cartilage thickness used to determine proper joint line. The distal femur 200 is surrounded by the thin black rim of cortical bone 645. The cancellous bone (also called trabecular bone) 650 is an inner spongy structure. An area of cartilage loss 655 can be seen at the posterior distal femur. For OA patients, the degenerative cartilage process typically leads to an asymmetric wear pattern that results in one femoral condyle with significantly less articulating cartilage than the other femoral condyle. This occurs when one femoral condyle is overloaded as compared to the other femoral condyle.

As can be understood from FIGS. 14C, 14E and 14F, the minimum cartilage thickness is observed and measured for the undamaged and damaged femoral condyle 302, 303 [block 1170]. If the greatest cartilage loss is identified on the surface of medial condyle 303, for example, then the lateral condyle 302 can be used as the cartilage thickness reference for purposes of POP. Similarly, if the greatest cartilage loss is identified on the lateral condyle 302, then the medial condyle 303 can be used as the cartilage thickness reference for purposes of POP. In other words, use the cartilage thickness measured for the least damaged condyle cartilage as the cartilage thickness reference for POP [block 1175].

As indicated in FIG. 14D, the thickness of cartilage can be analyzed in order to restore the damaged knee compartment back to its pre-OA status. In each of the MRI slices taken in regions A and B in FIG. 14B, the reference lines as well as the major and minor axes 485, 490 of ellipse contours 480', 480" in one femoral condyle 303 can be obtained.

As shown in FIG. 14F, for the three-point method, the tangents are drawn on the condylar curve at zero degrees and 90 degrees articular contact points. The corresponding tangent contact spots t1 and t2 are obtained from the tangents. The line 1450 perpendicular to the line 1455 determines the center of the ellipse curve, giving the origin of (0, 0). A third tangent contact spot t3 can be obtained at any point along the ellipse contour between the zero degree, t1 point and the 90 degree, t2 point. This third spot t3 can be defined as k, where k=1 to n points.

The three-point tangent contact spot analysis may be employed to configure the size and radius of the condyle 303 of the femur bone model 28'. This provides the "x" coordinate and "y" coordinate, as the (x, y) origin (0, 0) shown in FIG. 14D. The inner ellipse model 480' of the femoral condyle shows the femoral condyle surrounded by cortical bone without the cartilage attached. The minimum cartilage thickness $tm_{min}$ outside the inner ellipse contour 480' is measured. Based on the analysis of the inner ellipse contour 480' (i.e., the bone surface) and outer ellipse contour 480" (i.e., the cartilage surface) of the one non-damaged condyle of the femur bone model 28', the inner ellipse contour 480' (i.e., the bone surface) and the outer ellipse contour 480"

(i.e., the cartilage surface) of the other condyle (i.e., the damage or deteriorated condyle) may be determined.

As can be understood from FIGS. 14B and 14D, ellipse contours 480', 480" are determined in areas A and B for the condyles 302, 303 of the femur bone model 28'. The inner ellipse contour 480', representing the bone-only surface, and the outer ellipse contour 480", representing the bone-and-cartilage surface, can be obtained. The minimum cartilage thickness $tm_{min}$ is measured based on the cartilage thickness tr between the inner ellipse 480' and outer ellipse 480". MRI slices of the two condyles 302, 303 of the femur bone model 28' in areas A and B are taken to compare the respective ellipse contours in areas A and B. If the cartilage loss is greatest at the medial condyle 303 in the MRI slices, the minimum thickness $tm_{min}$ for the cartilage can be obtained from the lateral condyle 302. Similarly, if the lateral condyle 302 has the greatest cartilage loss, the cartilage thickness $tm_{min}$ can be obtained from undamaged medial condyle 303 of the femur restored bone model 28'. The minimum cartilage can be illustrated in the formula, $tm_{min}$=MIN (ti), where i=1 to k.

ii. Determining Joint Gap

As mentioned above, in one embodiment, the adjustment value tr may be determined via a joint line gap assessment. The gap assessment may serve as a primary estimation of the gap between the distal femur and proximal tibia of the bone images. The gap assessment may help achieve proper ligament balancing.

In one embodiment, an appropriate ligament length and joint gap may not be known from the 2D bone models or images 28', 28" (see, e.g. FIG. 3B) as the bone models or images may be oriented relative to each other in a fashion that reflects their deteriorated state. For example, as depicted in FIG. 14J, which is a coronal view of bone models 28', 28" oriented (e.g., tilted) relative to each other in a deteriorated state orientation, the lateral side 1487 was the side of the deterioration and, as a result, has a greater joint gap between the distal femur and the proximal tibia than the medial side 1485, which was the non-deteriorated side of the joint in this example.

In one embodiment, ligament balancing may also be considered as a factor for selecting the appropriate implant size. As can be understood from FIG. 14J, because of the big joint gap in the lateral side 1487, the presumed lateral ligament length (L1+L2+L3) may not be reliable to determine proper ligament balancing. However, the undamaged side, which in FIG. 14J is the medial side 1485, may be used in some embodiments as the data reference for a ligament balancing approach. For example, the medial ligament length (M1+M2+M3) of the undamaged medial side 1485 may be the reference ligament length used for the ligament balancing approach for implant size selection.

In one embodiment of the implant size selection process, it may be assumed that the non-deteriorated side (i.e., the medial side 1485 in FIG. 14J in this example) may have the correct ligament length for proper ligament balancing, which may be the ligament length of (M1+M2+M3). When the associated ligament length ("ALL") associated with a selected implant size equals the correct ligament length of (M1+M2+M3), then the correct ligament balance is achieved, and the appropriate implant size has been selected. However, when the ALL ends up being greater than the correct ligament length (M1+M2+M3), the implant size associated with the ALL may be incorrect and the next larger implant size may need to be selected for the design of the arthroplasty jig 2.

Figure 14G:
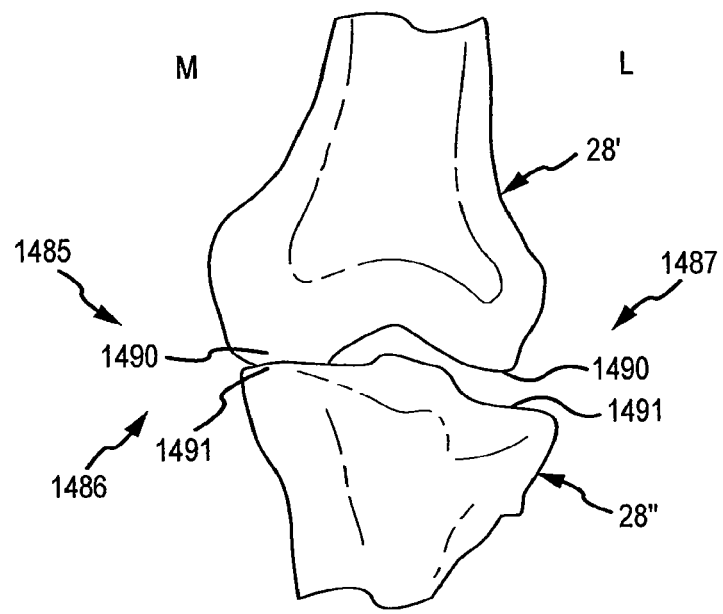
FIGS. 14G and 14H illustrate coronal views of the bone images in their alignment relative to each as a result of OA.
Figure 14H:
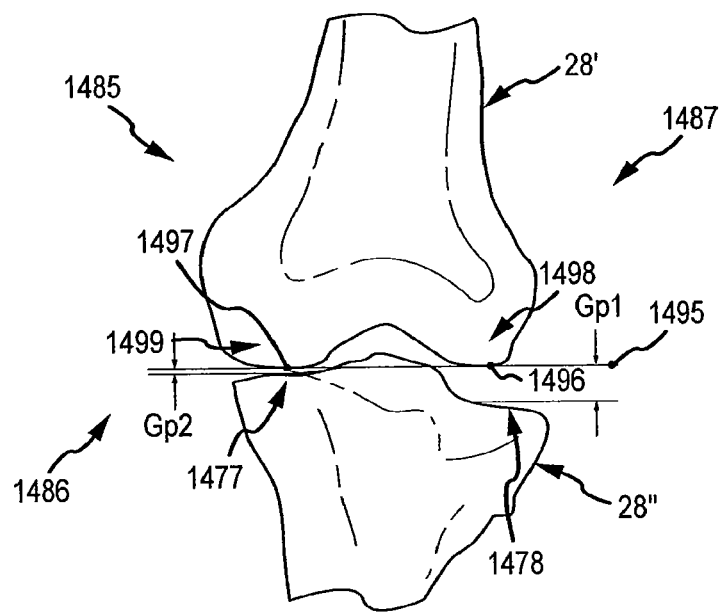

For a discussion regarding the gap assessment, which may also be based on ligament balance off of a non-deteriorated side of the joint, reference is made to FIGS. 14G and 14H. FIGS. 14G and 14H illustrate coronal views of the bone models 28', 28" in their post-degeneration alignment relative to each as a result of OA or injury. As shown in FIG. 14G, the tibia model 28" is tilted away from the lateral side 1487 of the knee 1486 such that the joint gap between the femoral condylar surfaces 1490 and the tibia condylar surfaces 1491 on the lateral side 1487 is greater than the joint gap on the medial side 1485.

As indicated in FIG. 14H, which illustrates the tibia in a coronal cross section, the line 1495 may be employed to restore the joint line of the knee 1486. The line 1495 may be caused to extend across each of lowest extremity points 1496, 1497 of the respective femoral lateral and medial condyles 1498, 1499. In this femur bone model 28', line 1495 may be presumed to be parallel or nearly parallel to the joint line of the knee 1486.

Figure 14I:
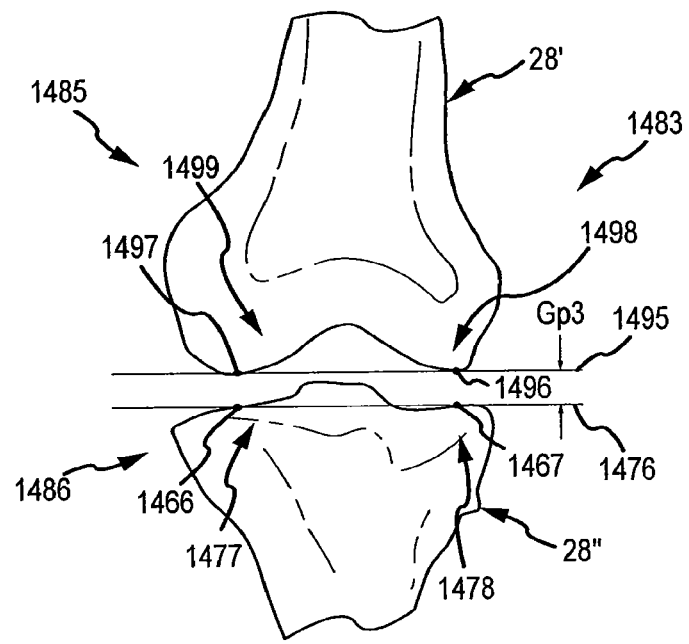
FIG. 14I illustrates a coronal view of the bone images with a restored gap Gp3.
Figure 14J:
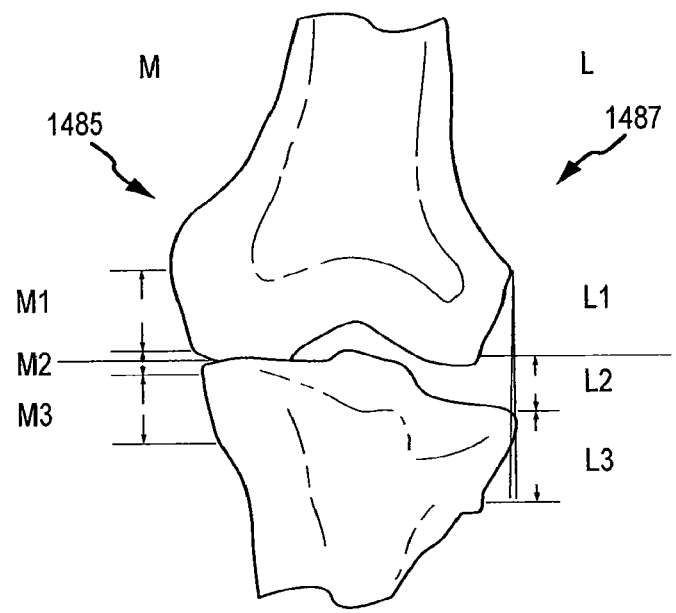
FIG. 14J is a coronal view of bone images oriented relative to each other in a deteriorated state orientation.

As illustrated in FIG. 14H, the medial gap Gp2 represents the distance between the distal femoral medial condyle 1499 and the proximal tibia medial plateau 1477. The lateral gap Gp1 represents the distance between the distal femoral lateral condyle 1498 and the proximal tibia lateral plateau 1478. In this example illustrated in FIG. 14H, the lateral gap Gp1 is significantly larger than the medial gap Gp2 due to degeneration caused by injury, OA, or etc., that occurred in the lateral side 1487 of the knee 1486. It should be noted that the alignment of the bone models 28', 28" relative to each other for the example illustrated in FIGS. 14G and 14H depict the alignment the actual bones have relative to each other in a deteriorated state. To restore the joint line reference and maintain ligament balancing for the medial collateral ligament (MCL) and lateral collateral ligament (LCL), the joint line gap Gp3 that is depicted in FIG. 14I, which is the same view as FIG. 14G, except with the joint line gap Gp3 in a restored state, may be used for the joint spacing compensation adjustment as described below. As illustrated in FIG. 14I, the lines 1495 and 1476 respectively extend across the most distal contact points 1496, 1497 of the femur condyles 1498, 1499 and the most proximal contact points 1466, 1467 of the tibia plateau condyles 1477, 1478.

For calculation purposes, the restored joint line gap Gp3 may be whichever of Gp1 and Gp2 has the minimum value. In other words, the restored joint line gap Gp3 may be as follows: Gp3=MIN (Gp1, Gp2). For purposes of the adjustment for joint spacing compensation, the adjustment value tr may be calculated as being half of the value for Gp3, or in other words, tr=Gp3/2. As can be understood from FIGS. 14G-14H and 14J, in this example, the non-deteriorated side 1485 has Gp2, which is the smallest joint line gap and, therefore, Gp3=Gp2 in the example depicted in FIG. 14G-14J, and tr=Gp2/2.

In one embodiment, the joint line gap assessment may be at least a part of a primary assessment of the geometry relationship between the distal femur and proximal tibia. In such an embodiment, the joint gap assessment step may occur prior to the femur planning steps of the POP process. However, in other embodiments, the joint line gap assessment may occur at other points along the overall POP process.

b. Determine Compensation for Joint Spacing

Figure 15:
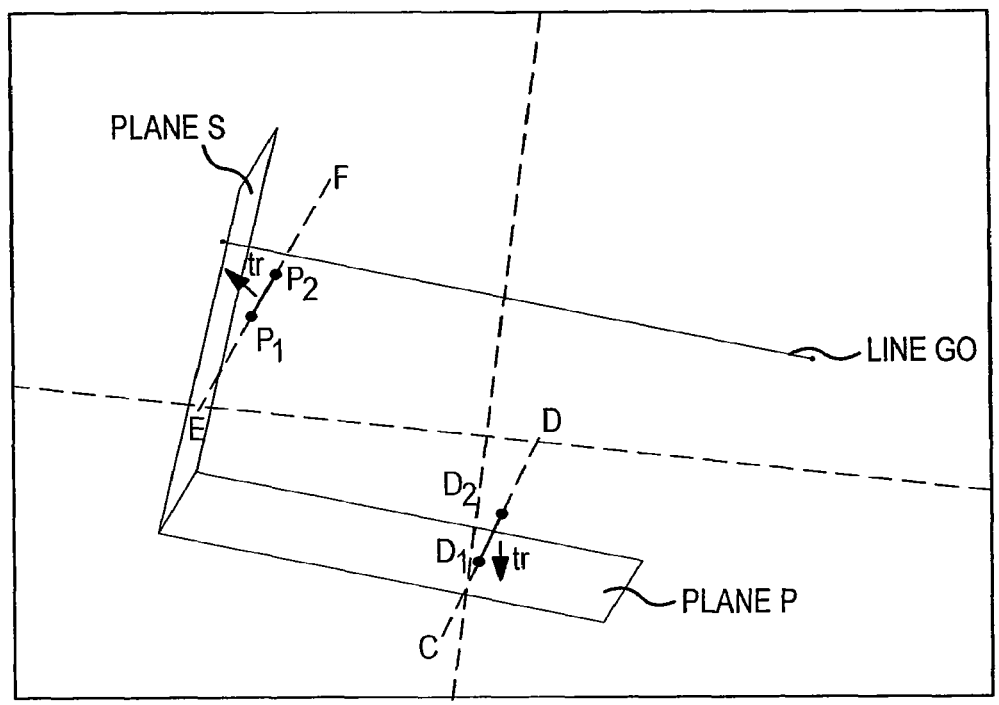
FIG. 15 is a 3D coordinate system wherein the femur reference data is shown.

Once the adjustment value tr is determined based off of cartilage thickness or joint line gap Gp3, the planning for the femoral implant model 34' can be modified or adjusted to compensate for the joint spacing in order to restore the joint line. As shown in FIG. 15, which is a 3D coordinate system wherein the femur reference data 100 is shown, the compensation for the joint spacing is performed both in distal and posterior approaches. Thus, the joint compensation points relative to the femur reference data are determined. As will be discussed later in this Detailed Description, the joint compensation points relative to the femur reference data will be used to determine the joint compensation relative to the femur implant.

Figure 16:
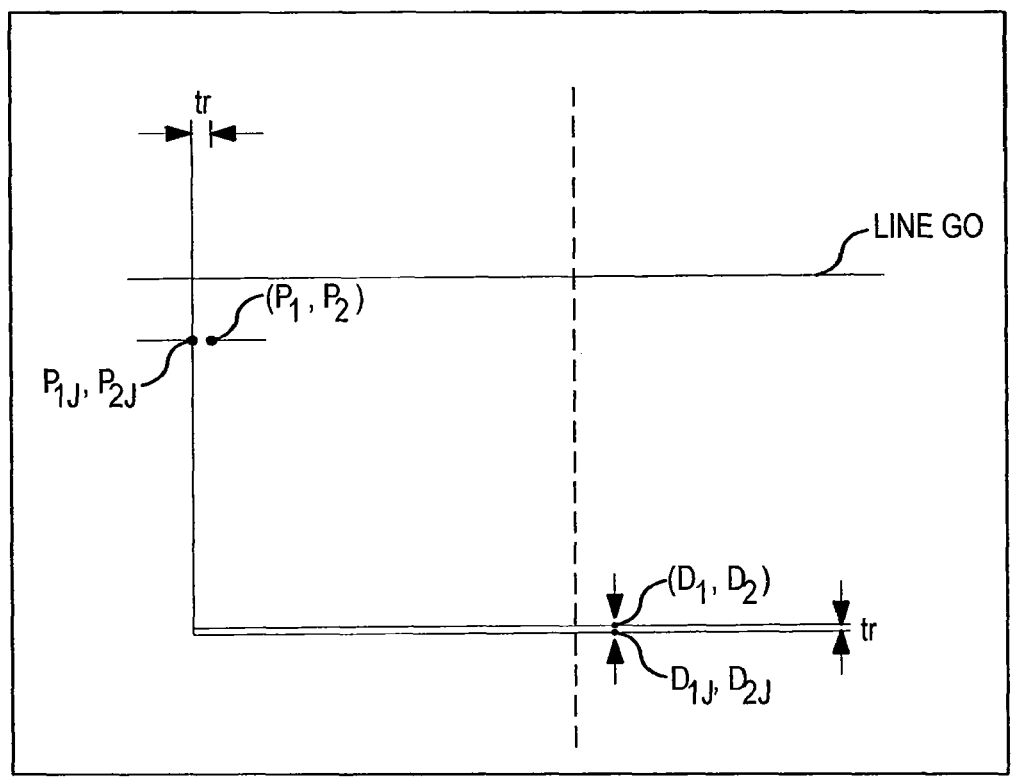
FIG. 16 is a y-z plane wherein the joint compensation points are shown.

As can be understood from FIG. 16, which is a y-z plane wherein the joint compensation points are shown, the posterior plane S and the distal plane P are moved away in the direction of normal of plane S and P respectively by the adjustment value tr. In one embodiment, the adjustment value tr is equal to the cartilage thickness. That is, the joint compensation points will be determined relative to the posterior plane S and the distal plane P which are moved away in the direction of normal of plane S and P, respectively, by an amount equal to the cartilage thickness. In some embodiments, the adjustment value tr is equal to one-half of the joint spacing. That is, the joint compensation points will be determined relative to the posterior plane S and the distal plane P which are moved away in the direction of normal of plane S and P, respectively, by an amount equal one-half the joint spacing. In other words, the femoral implant accounts for half of the joint spacing compensation, while the tibia implant will account for the other half of the joint spacing compensation.

As can be understood from FIG. 15, the femur reference data 100 was uploaded onto a coordinate system, as described above. To compensate for the joint spacing, the distal line-$D_1D_2$ is moved closer to the distal plane-P by an amount equal to the adjustment value tr, thereby resulting in joint spacing compensation points $D_{1J}$, $D_{2J}$ and line $D_{1J}D_{2J}$. The distal plane P was previously moved by adjustment value tr. Similarly, posterior reference line $P_1P_2$ is moved closer to the posterior plane-S by an amount equal to the adjustment value tr, thereby resulting in joint spacing compensation points $P_{1J}$, $P_{2J}$ and line $P_{1J}P_{2J}$. The trochlear groove reference line-line GO does not move and remains as the reference line for the joint spacing compensation. Lines $D_{1J}D_{2J}$ and $P_{1J}P_{2J}$ will be stored and utilized later for an analysis related to the femoral implant silhouette curve.

4. Selecting the Sizes for the Femoral Implants

The next steps are designed to select an appropriate implant size such that the implant will be positioned within the available degrees of freedom and may be optimized by 2D optimization. There are 6 degrees of freedom for a femoral implant to be moved and rotated for placement on the femur. For example, the translation in the x direction is fixed based on the reference planes-S and P and sagittal slices of femur as shown in FIGS. 4 and 7C. Rotation around the y axis, which corresponds to the varus/valgus adjustment is fixed based on the reference lines determined by analysis of the coronal slices, namely, lines EF and AB, and coronal plane-S as shown in FIGS. 4 and 7B. Rotation around the z axis, which corresponds to internal/external rotation, is fixed by the trochlear groove reference line, line GO or TGB, axial-distal reference line, line CD, and axial-posterior reference line, line AB, as shown in the axial views in FIGS. 4 and 6A-6E. By fixing these three degrees of freedom, the position of the implant can be determined so that the outer silhouette line of the implant passes through both the distal reference line and posterior reference line. Optimization will search for a sub-optimal placement of the implant such that an additional angle of flange contact is greater than but relatively close to 7 degrees. Thus, by constraining the 3 degrees of freedom, the appropriate implant can be determined.

a. Overview of Selection of Femoral Implant

Figure 20A:
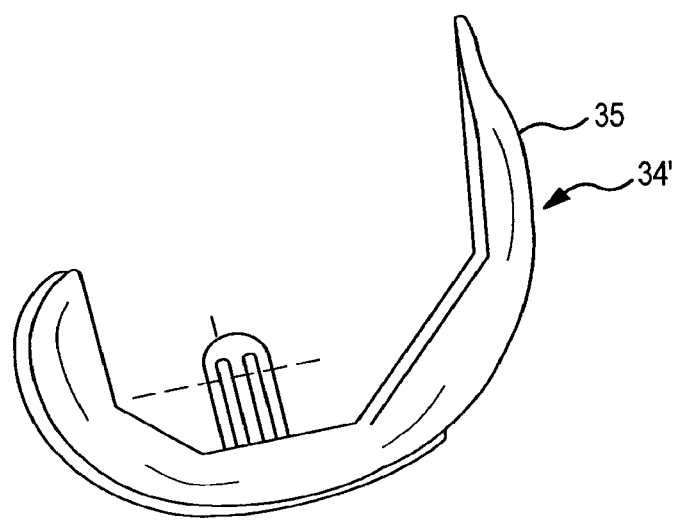
FIG. 20A is a candidate implant model mapped onto a y-z plane.
Figure 20B:
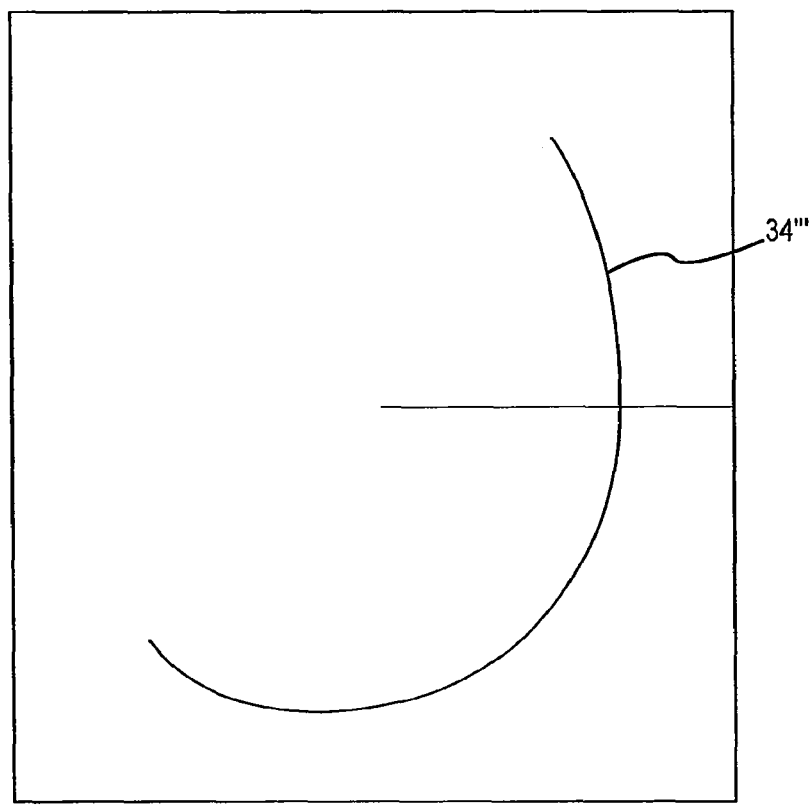
FIG. 20B is the silhouette curve of the articular surface of the candidate implant model.
Figure 20C:
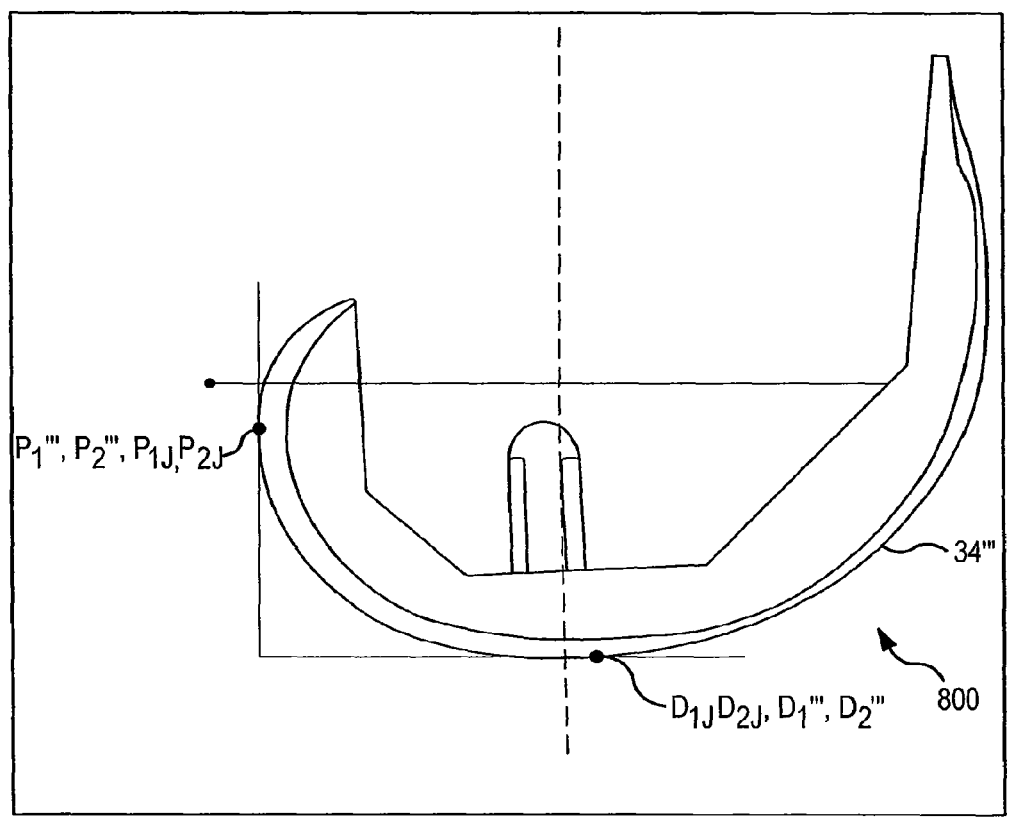
FIG. 20C, is the silhouette curve of the candidate implant model aligned with the joint spacing compensation points $D_{1,j}D_{2,j}$ and $P_{1,j}P_{2,j}$.

Based on previously determined femoral implant data 100', as shown in FIGS. 11-13, a set of 3 possible sizes of implants are chosen. For each implant, the outer 2D silhouette curve of the articular surface of the candidate implant model is computed and projected onto a y-z plane, as shown in FIGS. 20A-20C. The calculated points of the silhouette curve are stored. Then, the sagittal slice corresponding to the inflection point 500 (see FIG. 21A) is found and the corresponding segmentation spline is considered and the information is stored. Then an iterative closest point alignment is devised to find the transform to match the implant to the femur.

The next sections of this Detailed Description will now discuss the process for determining the appropriate implant candidate, with reference to FIGS. 17-22.

i. Implant Selection

In one embodiment, there is a limited number of sizes of a candidate femoral implant. For example, one manufacturer may supply six sizes of femoral implants and another manufacturer may supply eight or another number of femoral implants. A first implant candidate 700 (see FIG. 17) may be chosen based on the distance L' between the posterior and distal reference lines $P_1'P_2'$ and $D_1'D_2'$ determined above in FIG. 13, with reference to the femoral implant reference data 100'. The distance L' of the candidate implants may be stored in a database and can be retrieved from the implant catalogue. In some embodiments, a second and third implant candidate 702, 704 (not shown) may be chosen based on the distance L between the posterior and distal reference lines $P_1P_2$ and $D_1D_2$ of the femur 28' determined above in FIG. 8, with reference to the femoral reference data 100 and distance L'. First implant candidate 700 has the same distance L as the patient femur. Second implant candidate 702 is one size smaller than the first implant candidate 700. Third implant candidate 704 is one size larger than the first implant candidate 700. In some embodiments, more than 3 implant candidates may be chosen.

The following steps 2-6 are performed for each of the implant candidates 700, 702, 704 in order to select the appropriate femoral implant 34'.

ii. Gross Alignment of Implant onto Femur

In some embodiments, the gross alignment of the implant 34' onto the femur 28' may be by comparison of the implant reference data 100' and the femur reference data 100. In some embodiments, gross alignment may be via comparison of the medial-lateral extents of both the implant and the femur. In some embodiments, both gross alignment techniques may be used.

Figure 17:
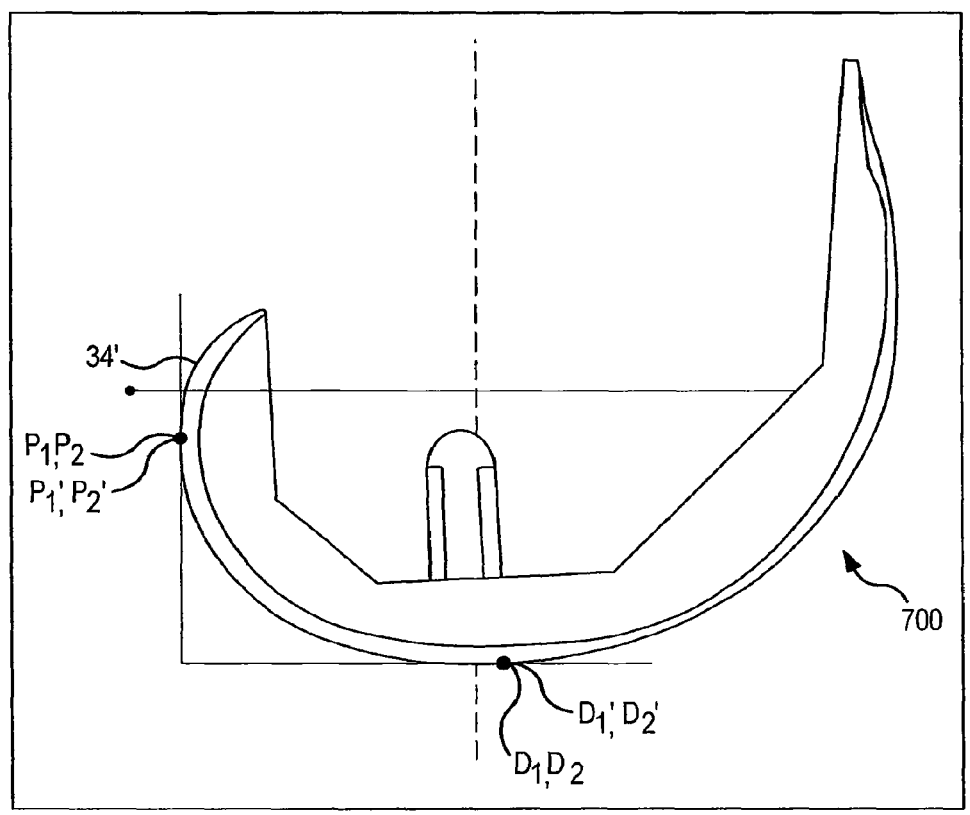
FIG. 17 illustrates the implant model 34' placed onto the same coordinate plane with the femur reference data.

In some embodiments, as shown in FIG. 17, which shows the implant 34' placed onto the same coordinate plane with the femur reference data 100, the implant candidate may be aligned with the femur. Alignment with the femur may be based on the previously determined implant reference lines $D_1'D_2'$ and $P_1'P_2'$ and femur reference lines $D_1D_2$ and $P_1P_2$.

Figures 18A, 18B:
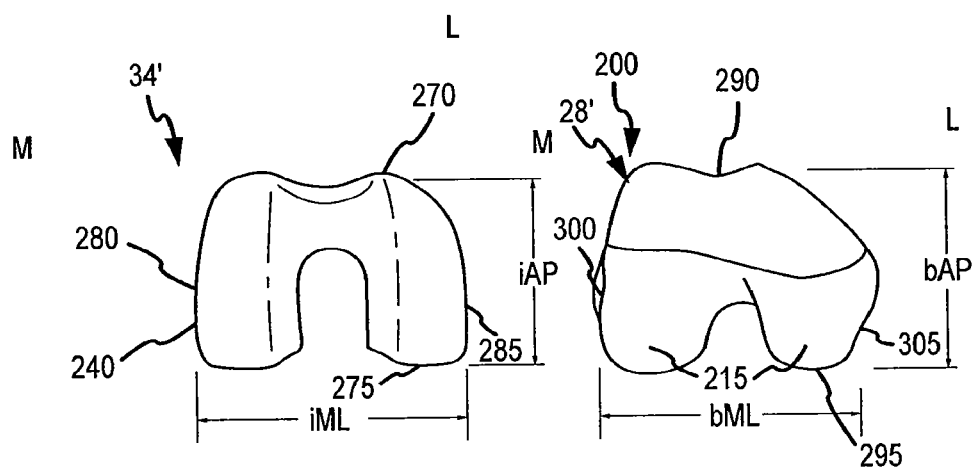
FIG. 18A is a plan view of the joint side of the femur implant model depicted in FIG. 3B.
FIG. 18B is an axial end view of the femur lower end of the femur bone model depicted in FIG. 3A.

In some embodiments, and as can be understood from FIGS. 18A-18C and 19A-19C, the medial lateral extent of the femur and the implant can be determined and compared to ensure the proper initial alignment. FIG. 18A is a plan view of the joint side 240 of the femur implant model 34' depicted in FIG. 3B. FIG. 18B is an axial end view of the femur lower end 200 of the femur bone model 28' depicted in FIG. 3A. The views depicted in FIGS. 18A and 18B are used to select the proper size for the femoral implant model 34'.

As can be understood from FIG. 18A, each femoral implant available via the various implant manufacturers may be represented by a specific femoral implant 3D computer model 34' having a size and dimensions specific to the actual femoral implant. Thus, the representative implant model 34' of FIG. 18A may have an associated size and associated dimensions in the form of, for example, an anterior-posterior extent iAP and medial-lateral extent iML, which data can be computed and stored in a database. These implant extents iAP, iML may be compared to the dimensions of the femur slices from the patient's actual femur 18. For example, the femur bone 18 may have dimensions such as, for example, an anterior-proximal extent bAP and a medial-lateral extent bML, as shown in FIG. 18B. In FIG. 18A, the anterior-posterior extent iAP of the femoral implant model 34' is measured from the anterior edge 270 to the posterior edge 275 of the femoral implant model 34', and the medial-lateral extent iML is measured from the medial edge 280 to the lateral edge 285 of the femoral implant model 34'.

Figure 18C:
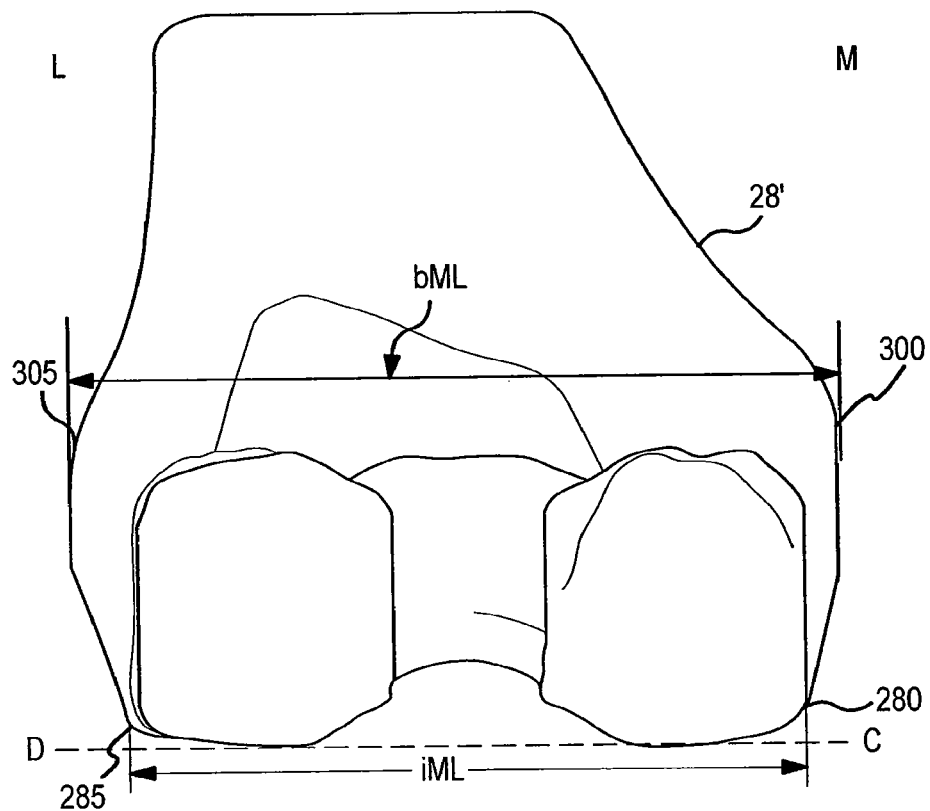
FIG. 18C illustrates the implant extents iAP and iML and the femur extents bAP, bML as they may be aligned for proper implant placement.

Each patient has femurs that are unique in size and configuration from the femurs of other patients. Accordingly, each femur slice will be unique in size and configuration to match the size and configuration of the femur medically imaged. As can be understood from FIG. 18B, the femoral anterior-posterior length bAP is measured from the anterior edge 290 of the patellofemoral groove to the posterior edge 295 of the femoral condyle, and the femoral medial-lateral length bML is measured from the medial edge 300 of the medial condyle to the lateral edge 305 of the lateral condyle. The implant extents iAP and iML and the femur extents bAP bML may be aligned for proper implant placement as shown in FIG. 18C and along the direction of axial-distal reference line-CD.

Figure 19A:
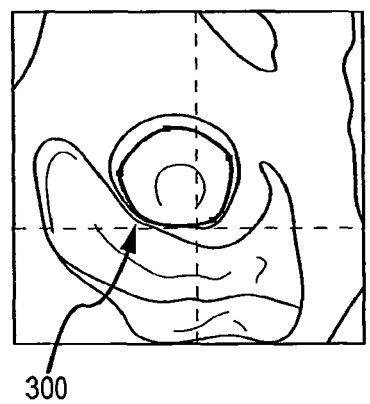
FIG. 19A shows the most medial edge of the femur in a 2D sagittal imaging slice.
Figure 19B:
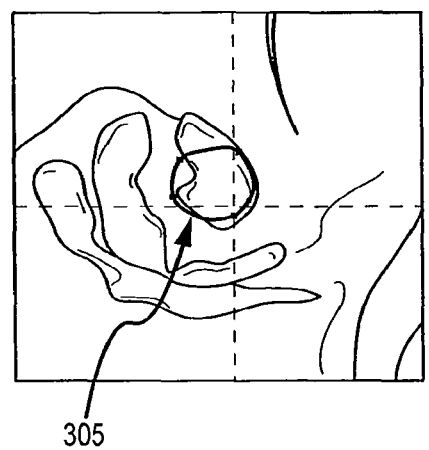
FIG. 19B, illustrates the most lateral edge of the femur in a 2D sagittal imaging slice.
Figure 19C:
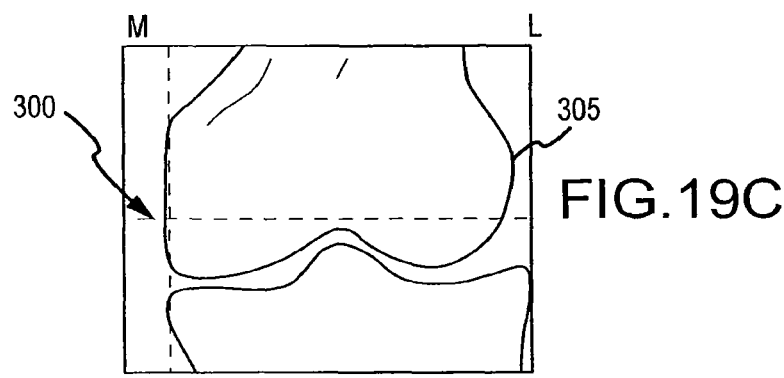
FIG. 19C is a 2D imaging slice in coronal view showing the medial and lateral edges.

As can be understood from FIGS. 19A-19C, these medial-lateral extents of the implant iML and femur bML can be measured from the 2D slices of the femur of FIG. 5A. For example, FIG. 19A, which shows the most medial edge of the femur in a 2D sagittal slice and FIG. 19B, which shows the most lateral edge of the femur in a 2D sagittal slice, can be used to calculate the bML of the femur 28'. The implant 34' will be centered between the medial and lateral edges, as shown in FIG. 19C, which is a 2D slice in coronal view showing the medial and lateral edges, thereby grossly aligning the implant with the femur.

iii. Determine Outer Silhouette Curve of Implant in Y-Z Plane

The silhouette of the femoral implant is the curve formed by farthest points from center in y-z plane projection of the femoral implant geometry. The points of the silhouette curve may be utilized to confirm placement of the implant onto the femur based on the femur reference lines that have been altered to account for the joint compensation.

Figure 21A:
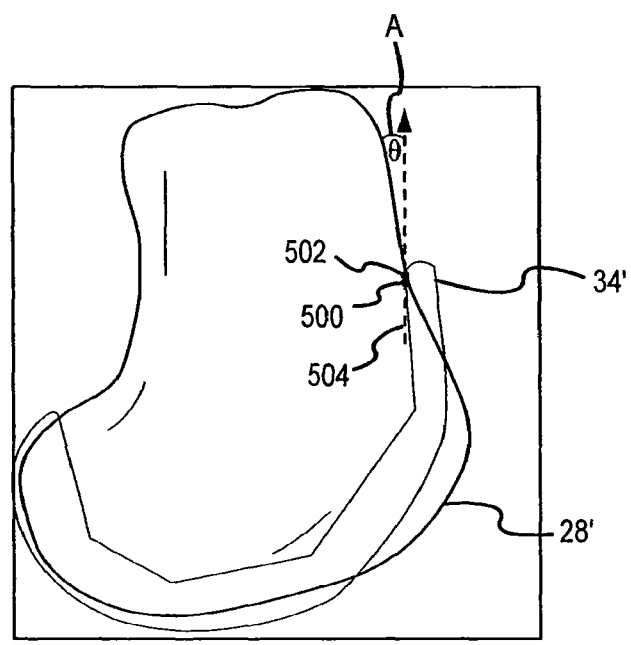
FIG. 21A illustrates a sagittal imaging slice of a distal femur with an implant model.
Figure 21B:
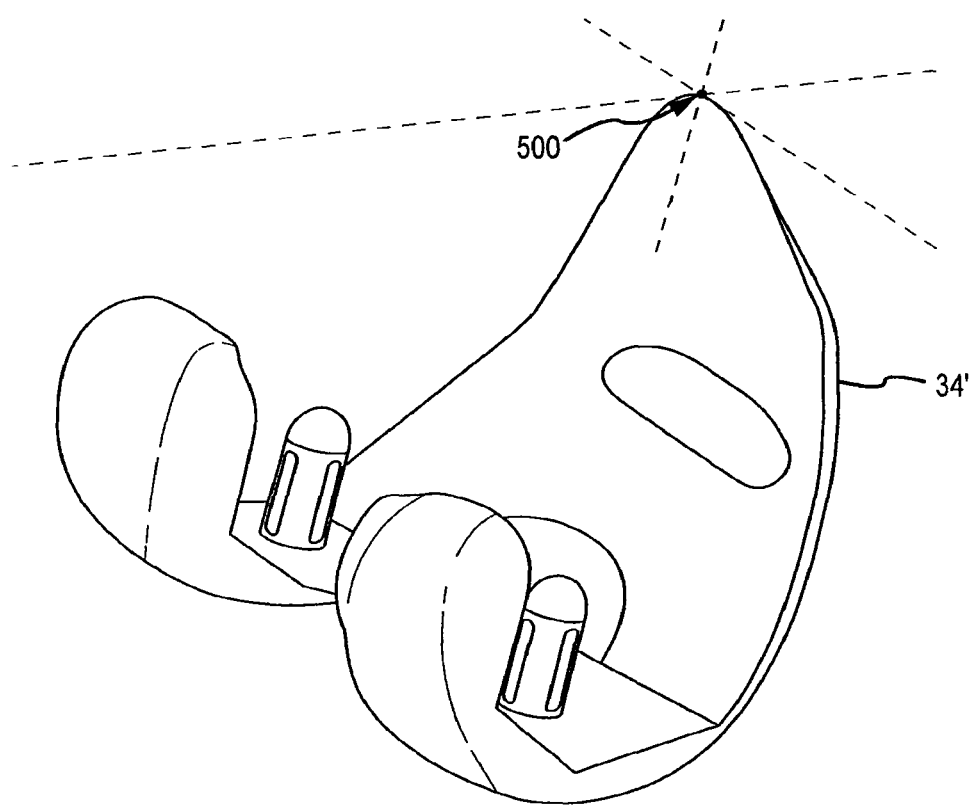
FIG. 21B depicts a femur implant model wherein the flange point on the implant is shown.

For a discussion of the process for determining the points of the silhouette curve of the femoral implant, reference is now made to FIGS. 20A-20C. As can be understood from FIG. 20A, which is an implant 34' mapped onto a y-z plane, the points of a candidate implant are retrieved from the implant database. The points are then imported onto a y-z plane and the silhouette curve can be determined. The silhouette curve 34''' is determined by finding the points that are the farthest from the center along an outer circumference 35 of the articular surface of the implant 34'. FIG. 20B, which is the silhouette curve 34''' of the implant 34', shows the result of the silhouette curve calculations. The silhouette curve data is then imported into a y-z plane that includes the joint spacing compensation data, as shown in FIG. 20C, which is the silhouette curve 34''' aligned with the joint spacing compensation points $D_{1J}D_{2J}$ and $P_{1J}P_{2J}$. The resulting joint spacing compensation and silhouette curve data 800 (e.g. $D_1'''D_2'''P_1'''P_2'''$) is stored for later analysis.

iv. Determination of Inflection Point, Flange Point, Femur Spline and Anterior Femur Cut Plane The flange point is determined and stored. As can be understood from FIG. 21A, which shows a distal femur 28' with an implant 34', the distal femur is analyzed and the flange point 500 of the implant 34' is determined relative to the anterior surface 502 of the distal end of a femur condyle 28'. FIG. 21B, which depicts a femur implant 34', illustrates the location of the flange point 500 on the implant 34' as determined by an analysis such as one illustrated in FIG. 21A.

The anterior cut plane 504 is determined and stored. The range of the anterior cut plane of the implant is determined such that the cut plane (and therefore the implant) is within certain tolerances. As shown in FIG. 21A, a cut plane 504 is determined based on the location of the implant 34' on the femur 28'. An angle A between the cut plane 504 and the flange point 500 is between approximately 7 and approximately 15 degrees. In some embodiments, the angle A is approximately 7 degrees. In some embodiments, the distal cut plane may be found as described below with respect to the final verification step. For each respective implant, the anterior cut plane and the distal cut plane are at a fixed angle for the implant. That is, once the anterior cut plane is found, the distal cut plane can be determined relative to the fixed angle and the anterior cut plane. Alternatively, once the distal cut plane is found, the anterior cut plane can be determined relative to the fixed angle and the distal cut plane.

Figure 21C:
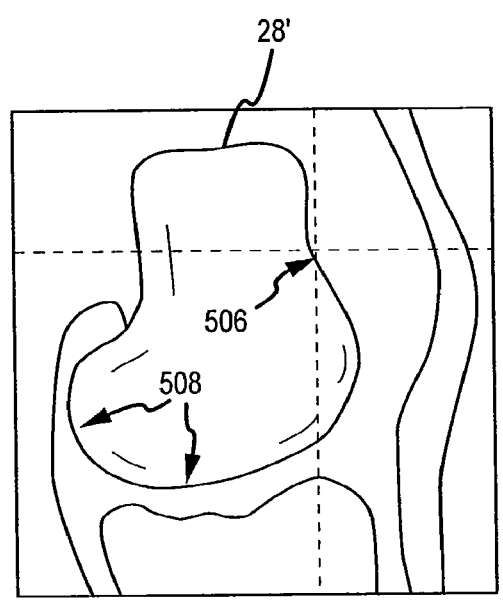
FIG. 21C shows an imaging slice of the distal femur in the sagittal view, wherein the inflection point located on the anterior shaft of the spline is shown.
Figure 21D:
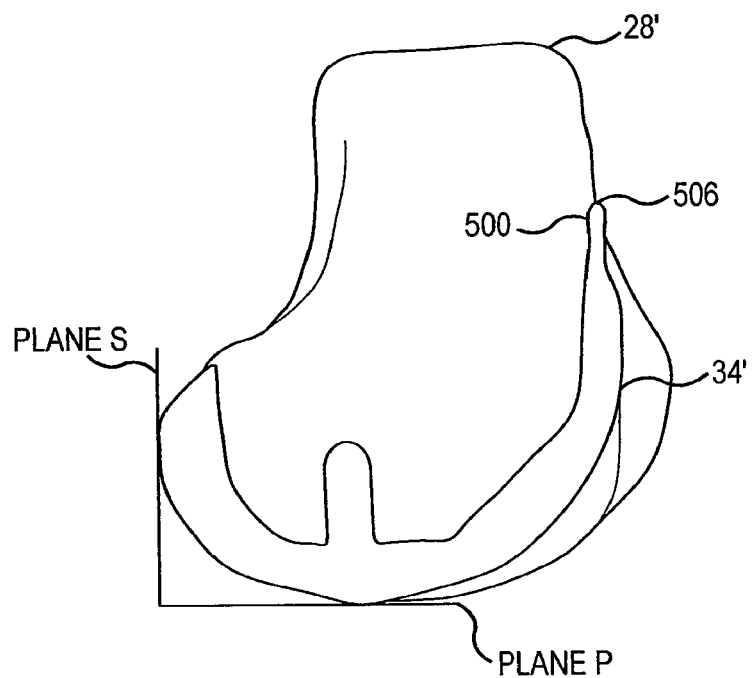
FIG. 21D illustrates the 2D implant model properly positioned on the 2D femur image, as depicted in a sagittal view.

The inflection point 506 is determined and stored. As shown in FIG. 21C, which shows a slice of the distal femur 28' in the sagittal view, the inflection point 506 is located on the anterior shaft of the spline 508 of femur 28' where the flange point 500 of the implant 34' is in contact with the femur 28'. An implant matching algorithm will match the flange point 500 of implant 34' to the spline 508 of the femur at approximately the inflection point 506 of the femur 28'. As can be understood from FIG. 21D, which shows the implant 34' positioned on the femur 28', the implant 34' should be aligned to touch the distal and posterior reference planes P, S respectively to reach proper alignment. In one embodiment, the implant matching algorithm is a customized extension of an algorithm known as iterative closest point matching.

The next section of the Detailed Description now discusses how the data and data points determined above and stored for future analysis will be used in the selection of an appropriate implant.

v. Determine Points of Set A and Set B

Determination of the data sets contained in Set A and Set B aid in determining the appropriate implant and ensuring that the chosen implant mates with the femur within certain tolerances.

The joint spacing compensation points $D_{1J}D_{2J}$ and $P_{1J}P_{2J}$ were determined as described with reference to FIG. 16 and are added to Set A. Next, the joint spacing compensation points $D_{1J}D_{2J}$ and $P_{1J}P_{2J}$ are matched to the closest respective points on the silhouette curve, as shown in FIG. 20C, thereby resulting in points $D_1'''D_2'''$ and $P_1'''P_2'''$ or the joint spacing compensation and silhouette curve data 800. Points $D_1'''D_2'''$ and $P_1'''P_2'''$ will be added to Set B.

The inflection point and flange point data are analyzed. An inflection point 506' is found to represent the inflection point 506 that is closest in proximity to the flange point 500, which were both discussed with reference to FIGS. 21A-21D. The point 506' is added to Set A. The flange point 500 is then projected to a y-z plane. The resulting flange point 500' is added to Set B.

Thus, Set A contains the following points: the joint spacing compensation points $D_{1J}D_{2J}$ and $P_{1J}P_{2J}$ and the inflection point 506'. Set B contains the following points: Points $D_1'''D_2'''$ and $P_1'''P_2'''$ (the joint spacing compensation and silhouette curve data 800) and the flange point 500'.

vi. Utilize the Data of Sets A and B

Find a rigid body transform. The data points of Set A and Set B are compared and a rigid body transform that most closely matches Set A to Set B is chosen. The rigid body transform will transform an object without scaling or deforming. That is, the rigid body transform will show a change of position and orientation of the object. The chosen transform will have rotation about the x-axis and translation in the y-z plane.

Find the inverse of the rigid body transform. The inverse of this rigid body transform is then imported into the y-z plane that also contains the femur reference lines $D_1D_2$ anti $P_1P_2$ and the femur spline 508 that corresponds to the flange point 500 of the implant 34'.

The steps described in subsections iv, v and vi of subsection D4(a) of this Detailed Description are repeated until the relative motion is within a small tolerance. In one embodiment, the steps are repeated fifty times. In some embodiments, the steps are repeated more than fifty times or less than fifty times.

Figure 22A:
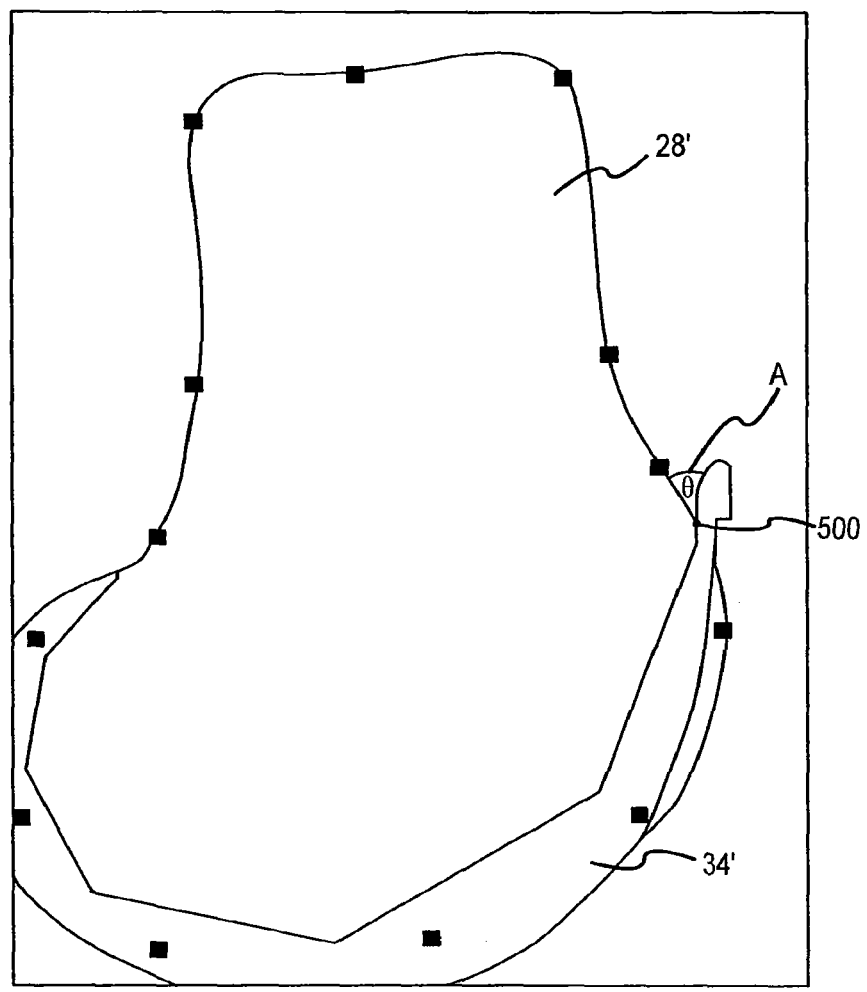
FIG. 22A depicts an implant model that is improperly aligned on a 2D femur image, as depicted in a sagittal view.
Figure 22B:
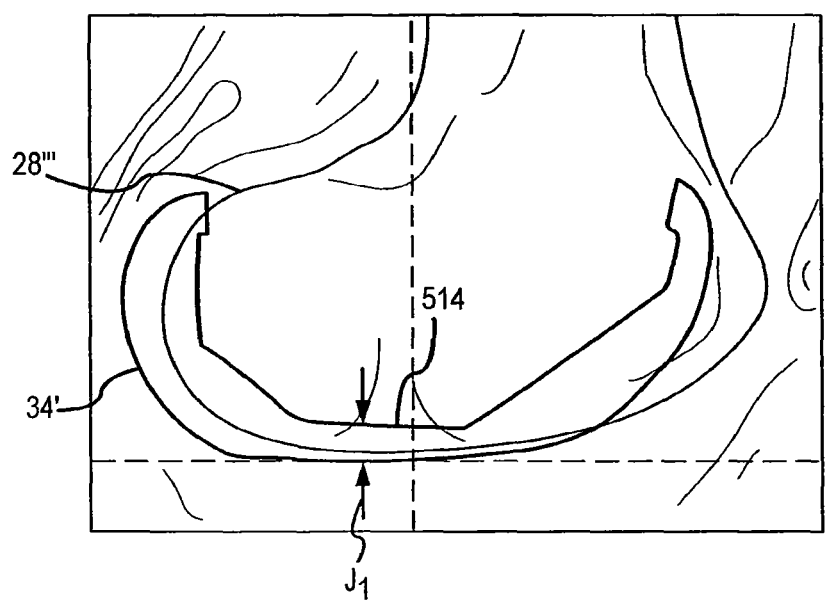
FIG. 22B illustrates the implant positioned on a femur transform wherein a femur cut plane is shown, as depicted in a sagittal view.

In some embodiments, and as shown in FIG. 22A, an acceptable translation in y-z plane may be determined. FIG. 22A depicts an implant that is improperly aligned on a femur, but shows the range of the search for an acceptable angle A. Within this range for angle A, the translation in y-z leads to finding the rigid body transform as described above. In some embodiments, the process may optimize y-z translation and rotation around the x-axis in one step. This can be done by rotating the implant silhouette curve by several half degree increments and then, for each increment, performing the steps described in subsections iv, v and vi of subsection D4(a) of this Detailed Description. Translation in the y-z axis only occurs during the analysis utilizing the inverse of the rigid body transform.

vii. Additional Verification and Confirmation of Femur Cut Plane

By using the above outlined procedure, an appropriate implant is found by choosing the implant and transform combination that provides an inflection angle that is greater than 7 degrees but closest to 7 degrees, as explained with reference to FIG. 21A.

In some embodiments, an additional verification step is performed by placing the implant 34' in the MRI with the transform 28''' that is found by the above described method. As can be understood from FIG. 22B, which illustrates the implant positioned on the femur transform wherein a femur cut plane is shown, during the verification step, a user may determine the amount of bone that is cut J, on the medial and lateral condyles by looking at the distal cut plane 514 of the implant 34'. $J_1$ is determined such that the thickness of the bone cut on both the medial and lateral sides is such that the bone is flat after the cut. Multiple slices in both the distal and medial areas of the bone can be viewed to verify $J_1$ is of proper thickness.

Once an appropriate femur implant is chosen, the preoperative planning process turns to the selection of an appropriate tibia implant. The tibia planning process includes a determination of the tibia reference lines to help determine the proper placement of the tibia implant. The candidate tibia implant is placed relative to the tibia reference lines and placement is confirmed based on comparison with several 2D segmentation splines.

E. Tibia Planning Process

For a discussion of the tibia planning process, reference is now made to FIGS. 23-32D. FIGS. 23-26B illustrate a process in the POP wherein the system 10 utilizes 2D imaging slices (e.g., MRI slices, CT slices, etc.) to determine tibia reference data, such as reference points and reference lines, relative to the undamaged side of the tibia plateau. The resulting tibia reference data 900 is then mapped or projected to an x-y plane (axial plane). A candidate tibia implant is chosen, which selection will be discussed with reference to FIGS. 27A-C. The tibia implant placement is adjusted and confirmed relative to the tibia, as discussed in more detail below with reference to FIGS. 28-32D.

1. Determining Tibia Reference Data

Figure 23:
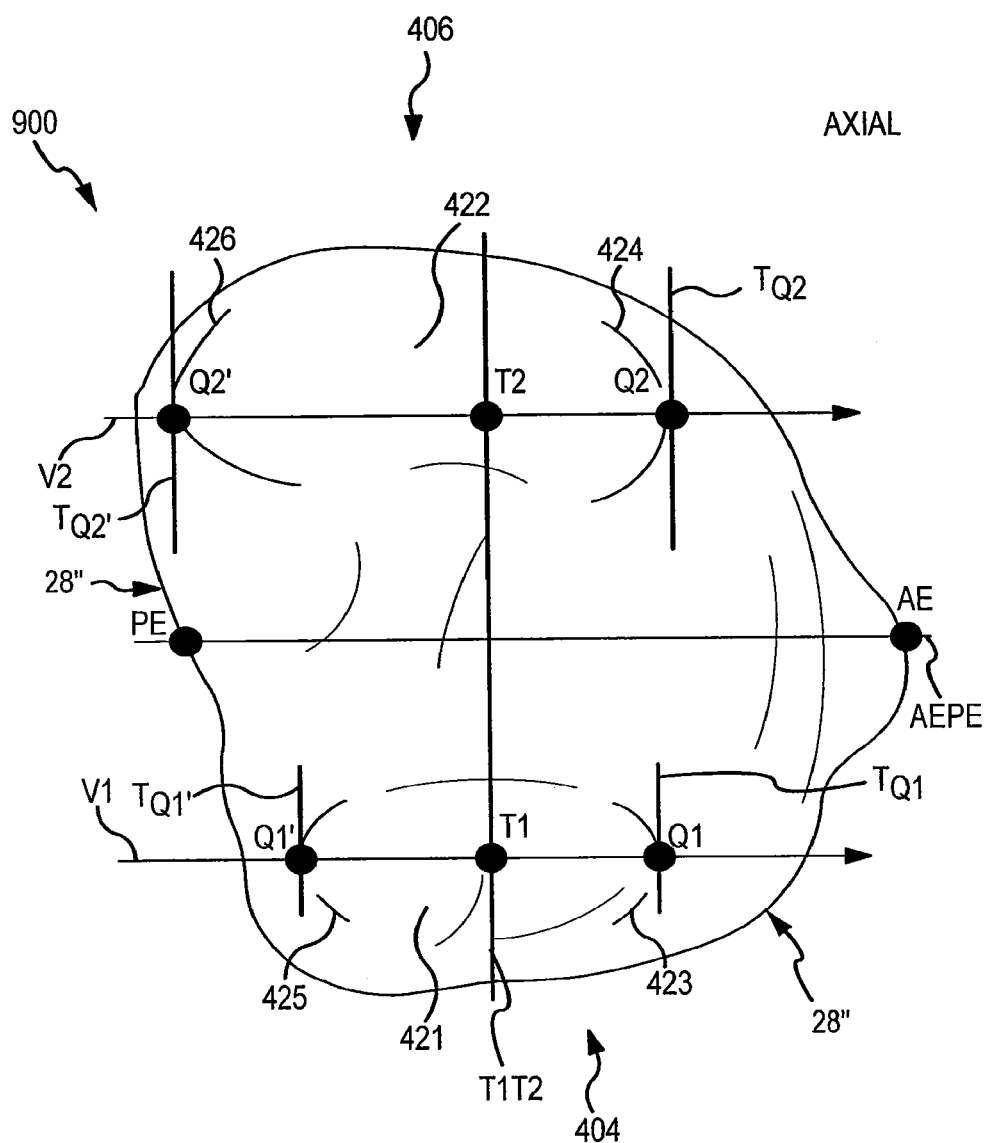
FIG. 23 is a top view of the tibia plateaus of a tibia bone image or model.

For a discussion of a process used to determine the tibia reference data 900, reference is now made to FIGS. 23-27B. As can be understood from FIG. 23, which is a top view of the tibia plateaus 404, 406 of a tibia bone image or model 28", the tibia reference data 900 may include reference points (e.g. $Q_1$, $Q_1'$), reference lines (e.g. $T_1T_2$, $V_1$) and a reference plane (e.g. S') (see FIGS. 26A-26B). In some embodiments, the tibia reference data 900 may also include the anterior-posterior extant (tAP) and the medial-lateral extant (tML) of the tibia 28" (see FIGS. 27A-27B). As shown in FIG. 23, each tibia plateau 404, 406 includes a curved recessed condyle contacting surface 421, 422 that is generally concave extending anterior/posterior and medial/lateral. Each curved recessed surface 421, 422 is generally oval in shape and includes an anterior curved edge 423, 424 and a posterior curved edge 425, 426 that respectively generally define the anterior and posterior boundaries of the condyle contacting surfaces 421, 422 of the tibia plateaus 404, 406. Depending on the patient, the medial tibia plateau 406 may have curved edges 424, 426 that are slightly more defined than the curved edges 423, 425 of the lateral tibia plateau 404.

a. Identify Points Q1, Q2 and Q1', Q2'

2D slices in the sagittal view are analyzed to determine the tibia flexion/extension adjustment. Anterior tangent lines $T_{Q1}$, $T_{Q2}$ can be extended tangentially to the most anterior location on each anterior curved edge 423, 424 to identify the most anterior points Q1, Q2 of the anterior curved edges 423, 424. Posterior tangent lines $T_{Q1}'$, $T_{Q2}'$ can be extended tangentially to the most posterior location on each posterior curved edge 425, 426 to identify the most posterior points Q1', Q2' of the posterior curved edges 425, 426. Thus, in one embodiment, the lateral side tibia plateau 404 can be analyzed via tangent lines to identify the highest points Q1, Q1'. For example, tangent line TQ1 can be used to identify the anterior highest point Q1, and tangent line $T_{Q1}'$ can be used to identify the posterior highest point Q1'. In some embodiments, a vector V1 extending between the highest points Q1, Q1' may be generally perpendicular to the tangent lines $T_{Q1}$, $T_{Q1}'$. Similarly, the medial side tibia plateau 406 can be analyzed via tangent lines to identify the highest points Q2, Q2'. For example, tangent line $T_{Q2}$ can be used to identify the anterior highest point Q2, and tangent line TQ2' can be used to identify the posterior highest point Q2'. In some embodiments, a vector V2 extending between the highest points Q2, Q2' may be generally perpendicular to the tangent lines $T_{Q2}$, $T_{Q2}'$.

i. Confirm points Q1, Q2 and Q1', Q2'

Figure 24A:
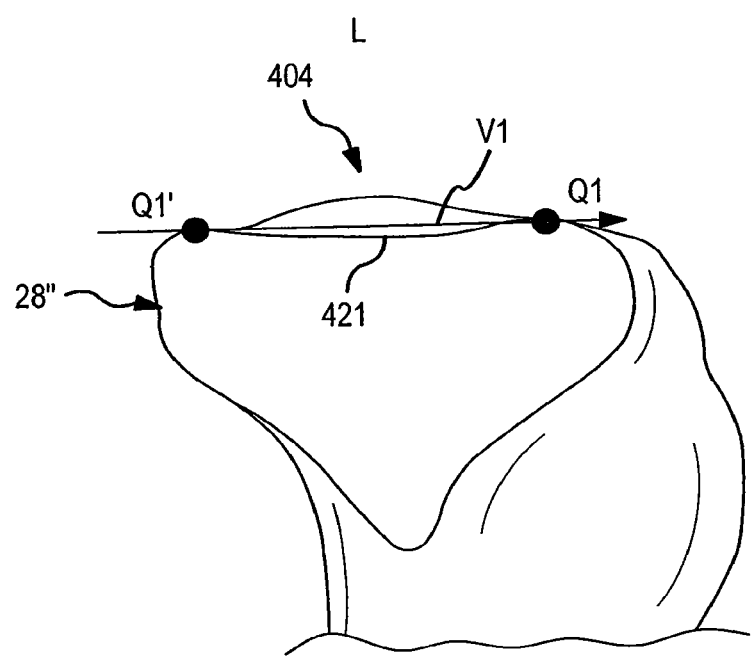
FIG. 24A is a sagittal cross section through a lateral tibia plateau of the 2D tibia bone model or image.
Figure 24B:
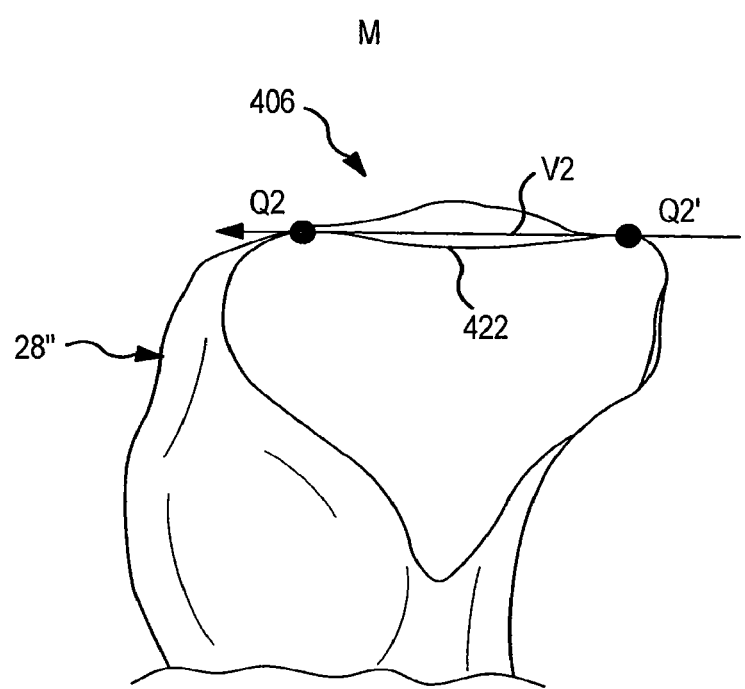
FIG. 24B is a sagittal cross section through a medial tibia plateau of the 2D tibia bone model or image.

As can be understood from FIGS. 24A-24D, the location of Q1, Q1', Q2 and Q2' may also be confirmed by an analysis of the appropriate sagittal slice. As shown in FIG. 24A, which is a sagittal cross section through a lateral tibia plateau 404 of the tibia model or image 28', points Q1 and Q1' can be identified as the most anterior and posterior points, respectively, of the curved recessed condyle contacting surface 421 of the lateral tibia plateau 404. As shown in FIG. 24B, which is a sagittal cross section through a medial tibia plateau 406 of the tibia model 28'', points Q2 and Q2' can be identified as the most anterior and posterior points, respectively, of the curved recessed condyle contacting surface 422 of the medial tibia plateau 406. Such anterior and posterior points may correspond to the highest points of the anterior and posterior portions of the respective tibia plateaus.

b. Determine Lines V1 and V2

As can be understood from FIGS. 23-24B, line V1 extends through anterior and posterior points Q1, Q1', and line V2 extends through anterior and posterior points Q2, Q2'. Line V1 is a lateral anterior-posterior reference line. Line V2 is a medial posterior-anterior reference line. Each line V1, V2 may align with the lowest point of the anterior-posterior extending groove/valley that is the elliptical recessed tibia plateau surface 421, 422. The lowest point of the anterior-posterior extending groove/valley of the elliptical recessed tibia plateau surface 421, 422 may be determined via ellipsoid calculus. Each line V1, V2 will be generally parallel to the anterior-posterior extending valleys of its respective elliptical recessed tibia plateau surface 421, 422 and will be generally perpendicular to its respective tangent lines $T_{Q1}$, $T_{Q1}'$, $T_{Q2}$, $T_{Q2}'$. The anterior-posterior extending valleys of the elliptical recessed tibia plateau surfaces 421, 422 and the lines V1, V2 aligned therewith may be generally parallel. The planes associated with lines V1 and V2 are generally parallel or nearly parallel to the joint line of the knee joint, as determined above.

Figure 24C:
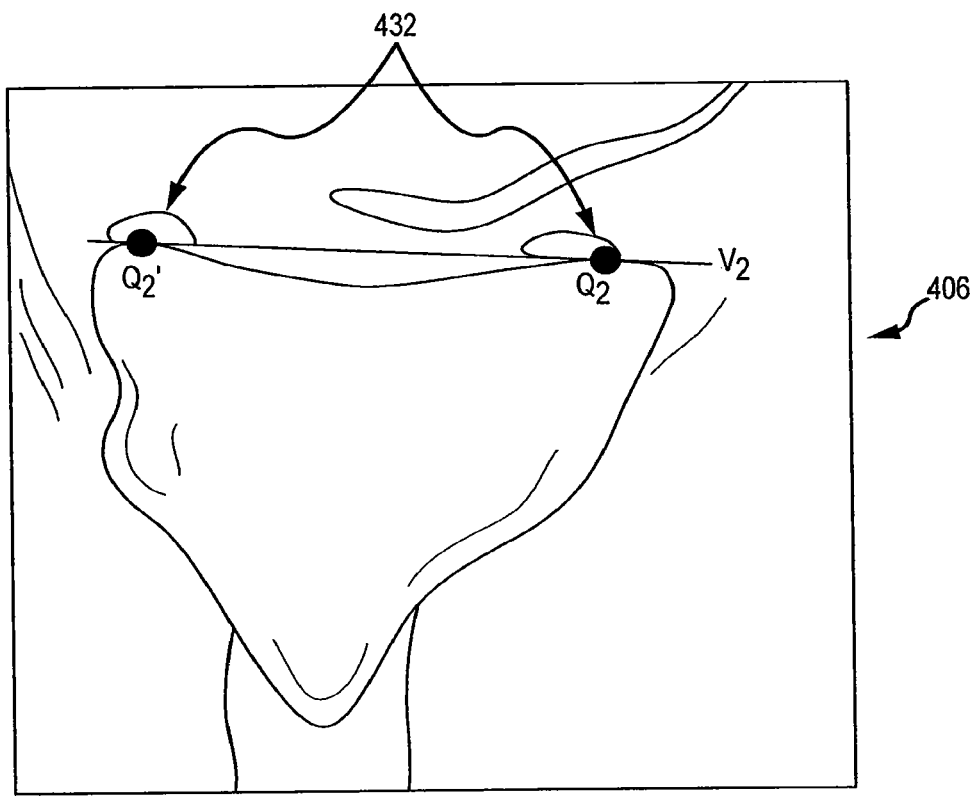
FIG. 24C depicts a sagittal cross section through an undamaged or little damaged medial tibia plateau of the 2D tibia model wherein osteophytes are also shown.
Figure 24D:
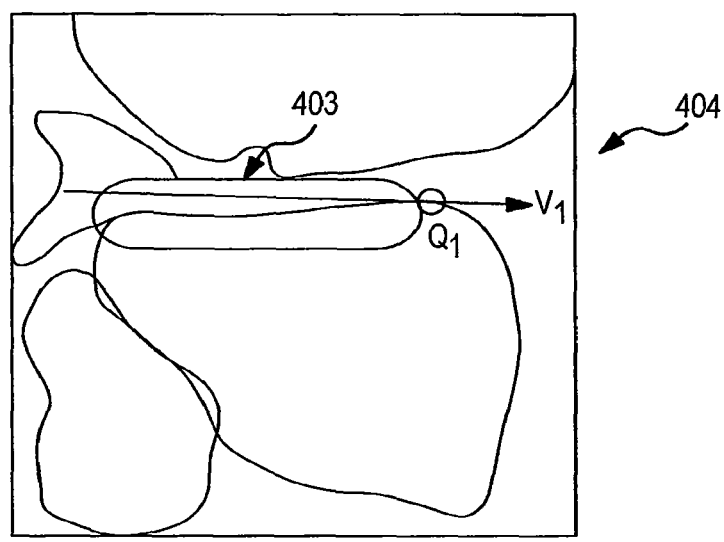
FIG. 24D is a sagittal cross section through a damaged lateral tibia plateau of the 2D tibia model.

Depending on the patient, the medial tibia plateau 406 may be undamaged or less damaged than the lateral tibia plateau 404. In such a case, the reference points Q2, Q2' and reference line V2 of the medial plateau 406 may be used to establish one or more reference points and the reference line of the damaged lateral tibia plateau. FIG. 24C depicts a sagittal cross section through an undamaged or little damaged medial tibia plateau 406 of the tibia model 28'', wherein osteophytes 432 are also shown. As indicated in FIG. 24C, the points Q2, Q2' can be located on the undamaged medial plateau and set as reference points. The anterior-posterior reference line, line V2, can be constructed by connecting the anterior and posterior reference points Q2, Q2'. The reference line V2 from the undamaged or little damaged medial side is saved for use in determining the reference line of the lateral tibia plateau in the case where the lateral tibia plateau is damaged. For example, as shown in FIG. 24D, which is a sagittal cross section through a damaged lateral tibia plateau 404 of the tibia model 28'', the anterior point Q1 is found to be undamaged. In this case, the established reference line V2 from the medial plateau can be applied to the damaged lateral plateau by aligning the reference line V2 with point Q1. By doing so, the reference line V1 of the lateral plateau can be established such that line V1 touches the reference point Q1 and extends through the damaged area 403. Thus, the reference line V1 in the lateral plateau is aligned to be parallel or nearly parallel to the reference line V2 in the medial plateau. While the above described process is described in terms of extrapolating one or more reference lines of a damaged lateral plateau from an analysis of the undamaged medial tibia plateau, it is understood that the same process can be undertaken where the lateral tibia plateau is undamaged and one or more reference lines of a damaged medial plateau can be extrapolated from the lateral tibia plateau.

In other embodiments, as can be understood from FIG. 24D and assuming the damage to the lateral tibia plateau 404 is not so extensive that at least one of the highest anterior or posterior points Q1, Q1' still exists, the damaged tibia plateau 404 can be analyzed via tangent lines to identify the surviving high point Q1, Q1'. For example, if the damage to the lateral tibia plateau 404 was concentrated in the posterior region such that the posterior highest point Q1' no longer existed, the tangent line $T_{Q1}$ could be used to identify the anterior highest point Q1. Similarly, if the damage to the medial tibia plateau 406 was concentrated in the anterior region such that the anterior highest point Q1' no longer existed, the tangent line $T_{Q1}'$ could be used to identify the posterior highest point Q1'. In some embodiments, a vector extending between the highest points Q1, Q1' may be generally perpendicular to the tangent lines $T_{Q1}$, $T_{Q1}'$.

c. Determine Reference Points T1 and T2 and Reference Line T1T2

Figure 25A:
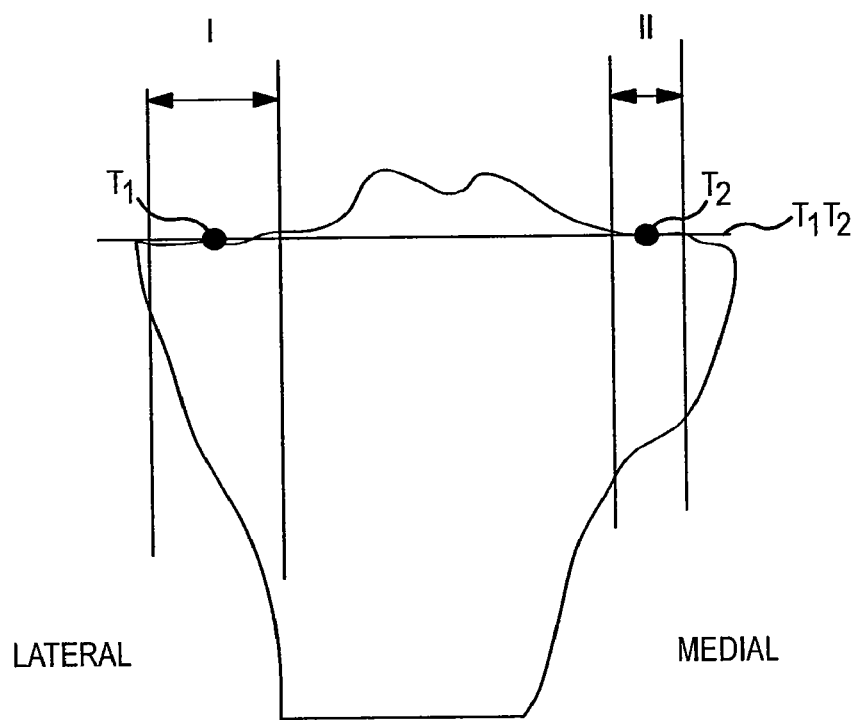
FIG. 25A is a coronal 2D imaging slice of the tibia.
Figure 25B:
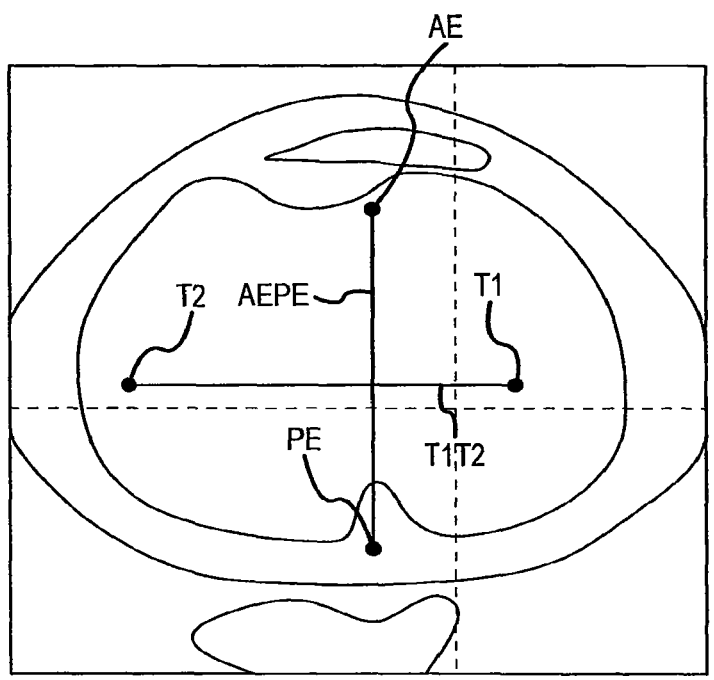
FIG. 25B is an axial 2D imaging slice of the tibia.

2D slices in both the axial and coronal views are analyzed to determine the varus/valgus adjustment by finding the reference points T1 and T2. As shown in FIGS. 25A-25B, which are coronal and axial 2D slices of the tibia, reference points T1 and T2 are determined by an analysis of the most proximal coronal slice (FIG. 25A) and the most proximal axial slice (FIG. 25B). As indicated in FIG. 25A, in which the tibia is shown in a 0° knee extension, reference points T1 and T2 are determined. The points T1 and T2 represent the lowest extremity of tangent contact points on each of the lateral and medial tibia plateaus, respectively. In one embodiment, tangent points T1 and T2 are located within the region between the tibia spine and the medial and lateral epicondyle edges of the tibia plateau, where the slopes of tangent lines in this region are steady and constant. For example, and as shown in FIG. 25A, the tangent point T1 is in the lateral plateau in Area I between the lateral side of the lateral intercondylar tubercle to the attachment of the lateral collateral ligament. For the medial portion, the tangent point T2 is in Area II between the medial side of the medial intercondylar tubercle to the medial condyle of the tibia.

As shown in FIG. 25B, the most proximal slice of the tibia in the axial view is analyzed to find reference points T1 and T2. As above, reference points T1 and T2 represent the lowest extremity of tangent contact points on each of the lateral and medial tibia plateaus. Once the reference points T1 and T2 are found in both the coronal and axial views, a line T1T2 is found.

A line T1T2 is created by extending a line between reference points T1 and T2. In some embodiments, the coronal and axial slices are viewed simultaneously in order to align the lateral and medial anterior-posterior reference lines V1 and V2. As shown in FIG. 23, the lateral and medial anterior-posterior reference lines V1 and V2 are generally perpendicular or nearly perpendicular to line T1T2.

d. Determine the Approximate ACL Attachment Point (AE) and the Approximate PCL Attachment Point (PE) of the Tibia and Reference Line AEPE As can be understood from FIGS. 23 and 25B, the reference points representing the approximate anterior cruciate ligament (ACL) attachment point of the tibia AE and the approximate posterior cruciate ligament (PCL) attachment point of the tibia PE are determined. The reference point AE can be determined by finding the approximate tibia attachment point for the ACL. The reference point PE can be determined by finding the approximate tibia attachment point for the PCL. The line AEPE connects through reference points AE and PE and may also be referred to as an ACL/PCL bisector line.

e. Confirm Location of Tibia Reference Data

As can be understood from FIG. 23, the tibia reference data 900 includes reference points and reference lines that help to define flexion/extension adjustment, varus/valgus adjustment and internal/external rotation. For example, the tibia flexion/extension adjustment is determined by an analysis of the sagittal images as shown in FIGS. 24A-D, which determine reference points Q1, Q1', Q2, Q2'. The tibia varus/valgus adjustment may be found by an analysis of FIG. 25A and finding reference points T1, T2 and reference line T1T2. As can be understood from FIG. 23, the proximal reference line, line T1T2, defines the internal/external rotation as shown in an axial view (line T1T2 in FIG. 25B) and the varus/valgus angle as shown in a coronal view (line T1T2 in FIG. 25A).

The location of the reference points and reference lines may also be confirmed based on their spatial relationship to each other. For example, as shown in FIGS. 23-24B, the anterior-posterior reference lines V1, V2 of the tibia plateau are generally parallel to the ACL/PCL bisector reference line, line AEPE. As indicated in FIGS. 23 and 25B, the axial-proximal reference line, line T1T2 is perpendicular or nearly perpendicular to anterior-posterior reference lines V1, V2. As shown in FIG. 23, the tangent lines $T_{Q1}$, $T_{Q2}$, $T_{Q1}'$, $T_{Q2}'$ are perpendicular or nearly perpendicular to the ACL/PCL bisector reference line, line AEPE.

f. Mapping the Tibia Reference Data to an x-y Plane

Figure 26A:
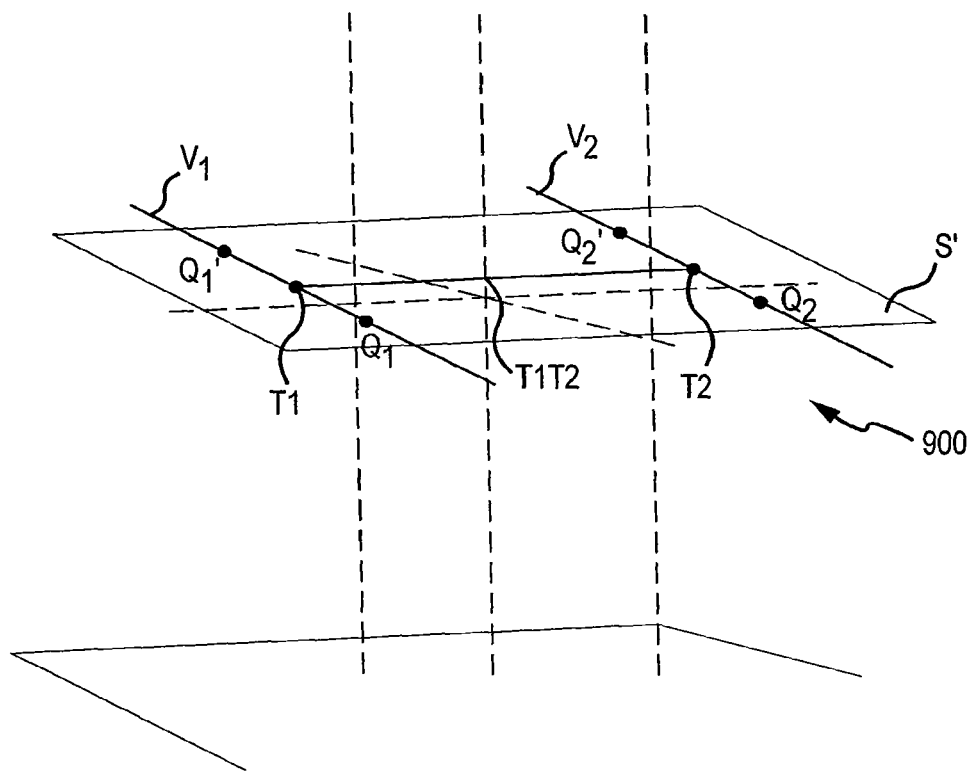
FIG. 26A depicts the tibia reference data on an x-y coordinate system.
Figure 26B:
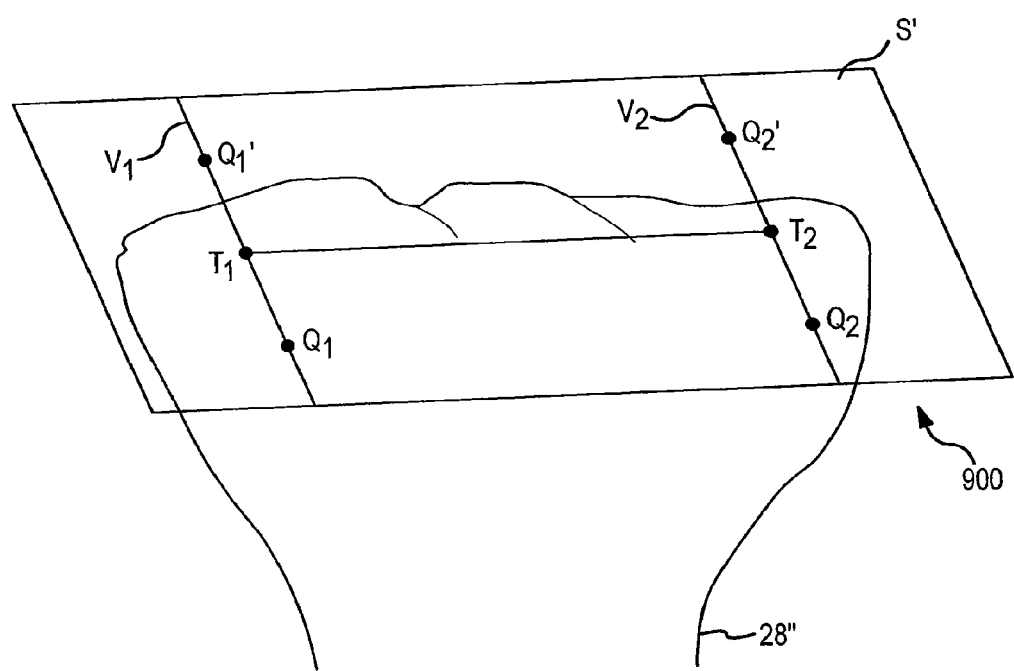
FIG. 26B depicts the tibia reference data on a proximal end of the tibia to aid in the selection of an appropriate tibia implant.

As can be understood from FIGS. 26A-26B, which depict the tibia reference data 900 on a coordinate system (FIG. 26A) and on a proximal end of the tibia (FIG. 26B), the tibia reference data 900 is mapped to an x-y coordinate system to aid in the selection of an appropriate tibia implant. As shown in FIG. 26A, the endpoints Q1, Q1', Q2, Q2' and their respective anterior posterior reference lines V1 and V2 and the endpoints T1, T2 and the proximal reference line T1T2 are each mapped to the reference plane. In addition, and as shown in FIG. 26B, the reference data 900 may be imported onto a 3D model of the tibia 28" for verification purposes. The tibia reference data 900 is stored for later analysis.

2. Selecting Tibia Implant Candidate

There are six degrees of freedom for placing the tibial implant onto the tibia. The reference points and reference lines determined above will constrain all but 2 degrees of freedom which are translated in the x-y plane. The sizing and positioning of the tibia implant (and the femoral component) will be verified with a 2D view of the knee and components.

As briefly discussed above with reference to FIGS. 1A and 1C, when selecting the tibia implant model 34" corresponding to the appropriate tibia implant size to be used in the actual arthroplasty procedure, the system 4 may use one of at least two approaches to select the appropriate size for a tibia implant [block 115]. In one embodiment, the tibia implant is chosen based on the size of the femoral implant that was determined above. In some embodiments, as discussed with reference to FIGS. 27A-27C, the system 4 determines the tibial anterior-posterior length tAP and the tibial medial-lateral length tML and the tibia implant 34" can be selected based on the anterior-posterior extent tAP of the proximal tibia. In some embodiments, the tibia implant may be selected based on both the tibial anterior-posterior length tAP and the tibial medial-lateral length tML In one embodiment, there is a limited number of sizes of a candidate tibia implant. For example, one manufacturer may supply six sizes of tibia implants and another manufacturer may supply eight or another number of tibia implants. The anterior-posterior length jAP and medial-lateral length jML dimensions of these candidate implants may be stored in a database. The tAP and tML are compared to the jAP and jML of candidate tibia implants stored in the database.

Figure 27A:
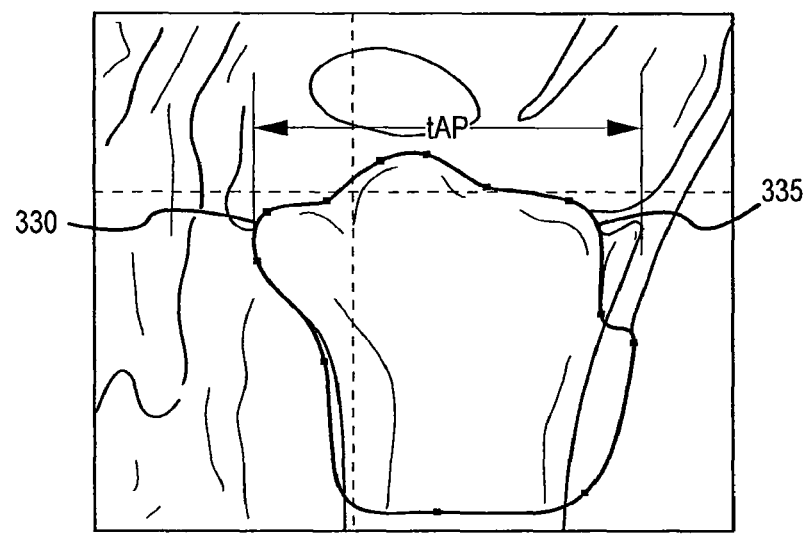
FIG. 27A is a 2D sagittal imaging slice of the tibia wherein a segmentation spline with an AP extant is shown.
Figure 27B:
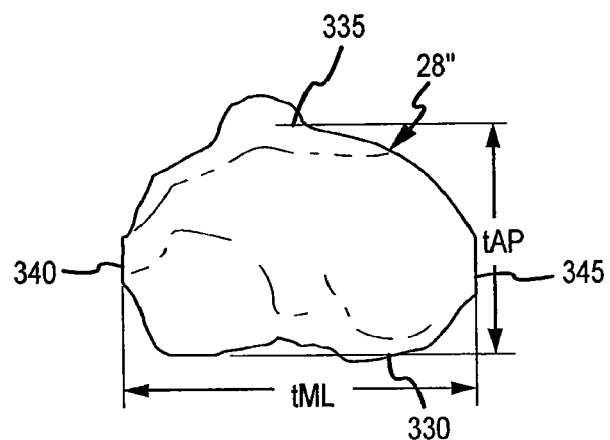
FIG. 27B is an axial end view of the tibia upper end of the tibia bone model depicted in FIG. 3A.
Figure 27C:
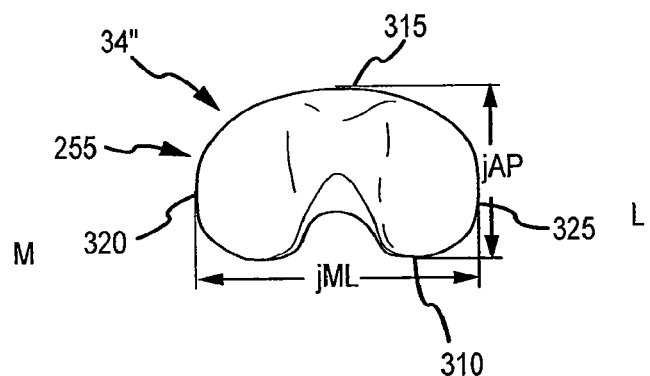
FIG. 27C is a plan view of the joint side of the tibia implant model depicted in FIG. 3B.

FIG. 27A is a 2D sagittal image slice of the tibia wherein a segmentation spline with an AP extant is shown. FIG. 27B is an axial end view of the tibia upper end of the tibia bone image or model 28" depicted in FIG. 3A. FIG. 27C is a plan view of the joint side 255 of the tibia implant model 34" depicted in FIG. 3B. The views depicted in FIGS. 27A-27C are used to select the proper size for the tibial implant model 34". The tibia implant may be chosen based on the maximum tAP extent as measured in an analysis of the segmentation spine as shown in FIG. 27A.

Each patient has tibias that are unique in size and configuration from the tibias of other patients. Accordingly, each tibia bone model 28" will be unique in size and configuration to match the size and configuration of the tibia medically imaged. As can be understood from FIG. 27B, the tibial anterior-posterior length tAP is measured from the anterior edge 335 of the tibial bone model 28" to the posterior edge 330 of the tibial bone model 28", and the tibial medial-lateral length tML is measured from the medial edge 340 of the medial plateau of the tibia bone model 28" to the lateral edge 345 of the lateral plateau of the tibia bone model 28".

As can be understood from FIG. 27C, each tibial implant available via the various implant manufacturers may be represented by a specific tibia implant 3D computer model 34" having a size and dimensions specific to the actual tibia implant. Thus, the representative implant model 34" of FIG. 3D may have an associated size and associated dimensions in the form of, for example, anterior-proximal extent tAP and the medial-lateral extent tML of the tibia model 34", as shown in FIG. 27B. In FIG. 27C, the anterior-posterior extent jAP of the tibia implant model 34" is measured from the anterior edge 315 to the posterior edge 310 of the tibial implant model 34", and the medial-lateral extent jML is measured from the medial edge 320 to the lateral edge 325 of the tibial implant model 34". Once the tibia implant candidate 34" is chosen, the reference lines jML, jAP of the implant candidate 34" are stored by the system 4 for later analysis.

3. Determine Tibia Implant Reference Data

Figure 28:
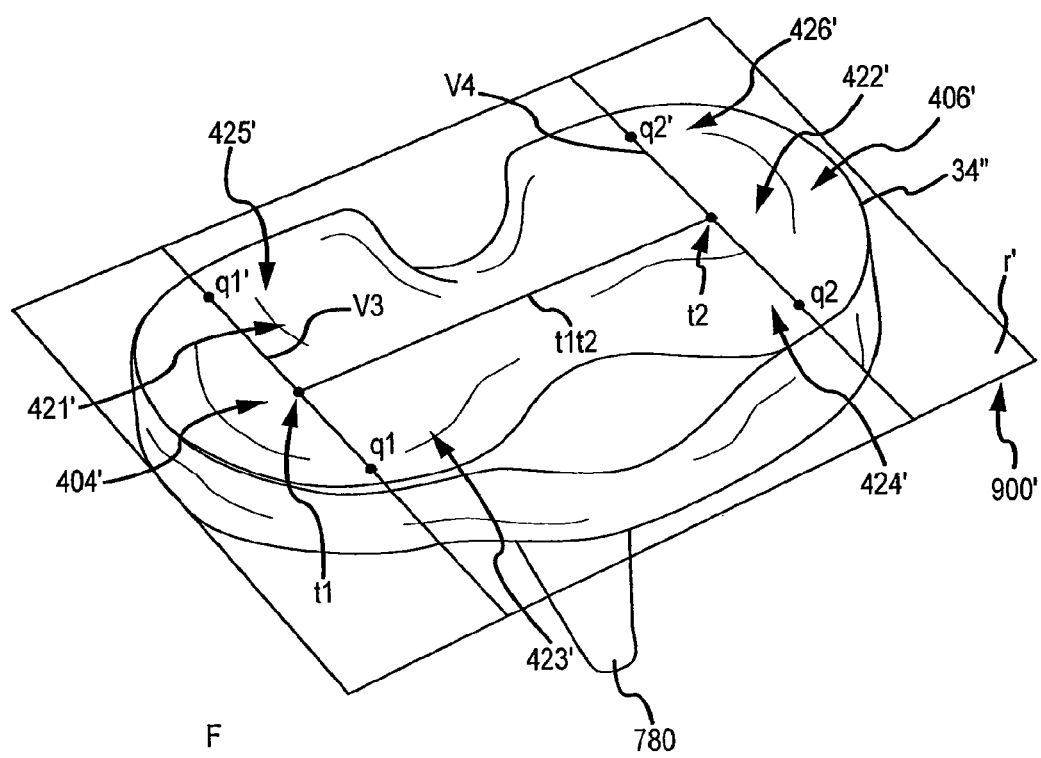
FIG. 28 is a top isometric view of the tibia plateaus of a tibia implant model.

As can be understood from FIG. 28, which is a top view of the tibia plateaus 404', 406' of a tibia implant model 34", wherein the tibia implant reference data 900' is shown, the tibia reference data 900' may include tangent points q1, q1', q2, q2' and corresponding anterior-posterior reference lines V3, V4 and intersection points t1, t2 and its corresponding proximal reference line t1t2.

In order to define the implant reference data 900' relative to the tibia model 28", the implant reference lines jML, jAP are imported into the same x-y plane with the tibia reference data 900 that was previously mapped to the x-y plane. For gross alignment purposes, the medial-lateral extent jML of the tibia implant 34" is aligned with the proximal reference line T1T2 of the tibia model 28". Then, the tibia reference data 900' is determined. The implant 34" and the bone model 28" may then undergo additional alignment processes.

a. Determine Tangent Points q1, q1', q2, q2'

As shown in FIG. 28, each tibia plateau 404', 406' includes a curved recessed condyle contacting surface 421', 422' that is generally concave extending anterior/posterior and medial/lateral. Each curved recessed surface 421', 422' is generally oval in shape and includes an anterior curved edge 423', 424' and a posterior curved edge 425', 426' that respectively generally define the anterior and posterior boundaries of the condyle contacting surfaces 421', 422' of the tibia plateaus 404', 406'. Thus, the lateral tangent points q1, q1' can be identified as the most anterior and posterior points, respectively, of the curved recessed condyle contacting surface 421' of the lateral tibia plateau 404'. The medial tangent points q2, q2' can be identified as the most anterior and posterior points, respectively, of the curved recessed condyle contacting surface 422' of the medial tibia plateau 406'.

b. Determine Reference Lines V3 and V4

As can be understood from FIG. 28, line V3 extends through anterior and posterior points q1, q1', and line V4 extends through anterior and posterior points q2, q2'. Line V3 is a lateral anterior-posterior reference line. Line V4 is a medial posterior-anterior reference line. Each line V3, V4 may align with the lowest point of the anterior-posterior extending groove/valley that is the elliptical recessed tibia plateau surface 421', 422'. The lowest point of the anterior-posterior extending groove/valley of the elliptical recessed tibia plateau surface 421', 422' may be determined via ellipsoid calculus. Each line V3, V4 will be generally parallel to the anterior-posterior extending valleys of its respective elliptical recessed tibia plateau surface 421', 422'. The length of the reference lines V3, V4 can be determined and stored for later analysis.

c. Determine Intersection Points t1, t2 and Implant Proximal Reference Line t1t2

As shown in FIG. 28, the intersection or reference points t1, t2 represent the midpoints of the respective surfaces of the lateral tibia plateau 404' and the medial tibia plateau 406'. Also, each intersection point t1, t2 may represent the most distally recessed point in the respective tibia plateau 404', 406'. An implant proximal reference line t1t2 is created by extending a line between the lateral and medial lowest reference points t1, t2. The length of the reference line t1t2 can be determined and stored for later analysis. This line t1t2 is parallel or generally parallel to the joint line of the knee. Also, as indicated in FIG. 28, the tibia implant 34" includes a base member 780 for being secured to the proximal tibia 28".

d. Align Implant Reference Data 900' with Tibia Reference Data 900

As can be understood from FIGS. 28 and 26A, the implant reference data 900' specifies the position and orientation of the tibia implant 34" and generally aligns with similar data 900 from the tibia bone model 28". Thus, the lateral tangent points q1, q1' and medial tangent points q2, q2' of the implant 34" generally align with the lateral tangent points Q1, Q1' and medial tangent points Q2, Q2' of the tibia 28". The anterior posterior reference lines V3, V4 of the implant 34" generally align with the anterior posterior reference lines V1, V2 of the tibia model 28". The intersection points t1, t2 of the implant 34" generally align with the reference points T1, T2 of the tibia 28". The proximal reference line t1t2 of the implant 34" generally aligns with the proximal reference line T1T2 of the tibia 28". Reference line t1t2 is approximately perpendicular to the anterior-posterior reference lines V3, V4.

The implant reference data 900' lies on a coordinate frame, plane r'. The tibia reference data 900 lies on a coordinate frame, plane s'. Thus, the alignment of the implant 34" with the tibia 28" is the transformation between the two coordinate frames plane r', plane s'. Thus, the gross alignment includes aligning the proximal line t1t2 of the implant 34" to the proximal line T1T2 of the tibia 28". Then, in a further alignment process, the reference points t1, t2 of the implant and the reference points T1, T2 of the tibia 28" are aligned. The implant 34" is rotated such that the sagittal lines of the implant 34" (e.g. V3, V4) are parallel or generally parallel to the sagittal lines of the tibia 28" (e.g. V1, V2). Once the tibia 28" and the implant 34" are in alignment (via the reference data 900, 900'), the tibial cut plane can be determined.

Figure 29A:
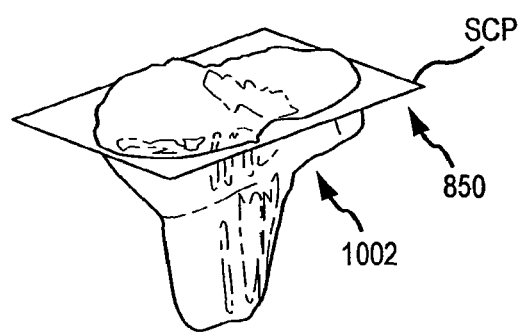
FIG. 29A is an isometric view of the 3D tibia bone model showing the surgical cut plane SCP design.
Figures 29B, 29C:
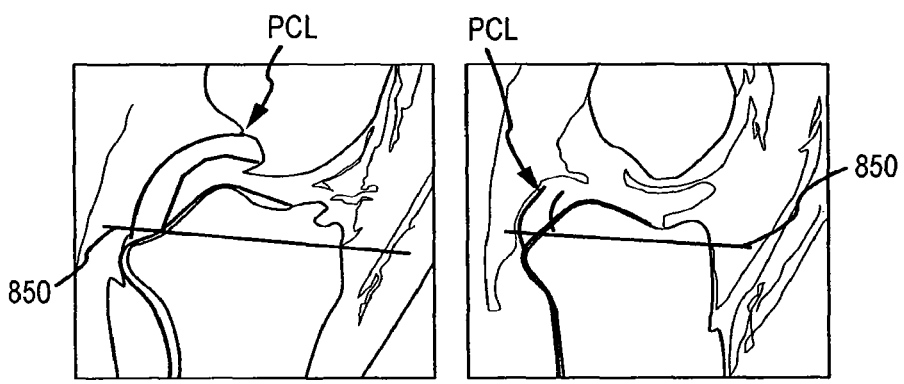
FIGS. 29B and 29C are sagittal MRI views of the surgical tibia cut plane SCP design with the posterior cruciate ligament PCL.

4. Determine Surgical Cut Plane for Tibia a. Determine Cut Plane of the Tibia Implant The cut plane of the tibia implant is determined. The user may determine this cut plane by a method such as one described with respect to FIGS. 29A-29C. FIG. 29A is an isometric view of the 3D tibia bone model 1002 showing the surgical cut plane SCP design. FIGS. 29B and 29C are sagittal MRI views of the surgical tibia cut plane SCP design with the posterior cruciate ligament PCL.

During the TKA surgery, the damaged bone surface portions of the proximal tibia will be resected from the cut plane level 850 and be removed by the surgeon. As shown in FIGS. 29B and 29C, the surgical tibial cut plane 850 may be positioned above the surface where the PCL is attached, thereby providing for the maintenance of the PCL during TKA surgery.

Figure 30A:
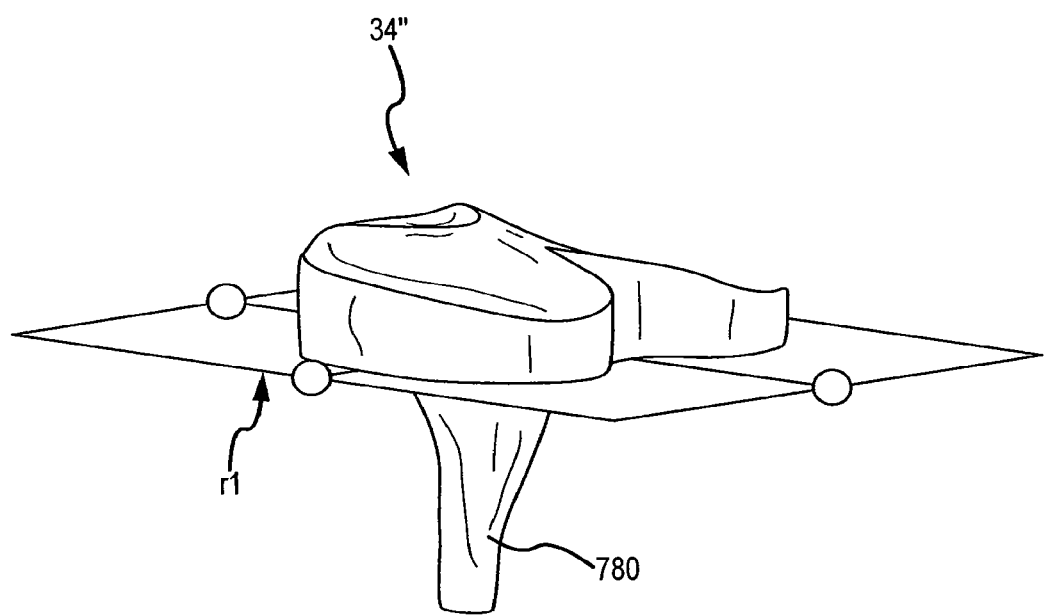
FIG. 30A is an isometric view of the tibia implant wherein a cut plane is shown.

FIG. 30A is an isometric view of the tibia implant 34" wherein a cut plane r1 is shown. As can be understood from FIG. 30A, the cut plane r1 of the implant 34" is the surgical tibial cut plane 850 and is a data point or set of data points that may be stored in the implant database. In order to determine whether an adjustment to the cut plane r1 must be made, the cut plane r1 of the tibia implant 34" is aligned with the tibia 28".

b. Determine Initial Cut Plane of the Tibia

Figure 30B:
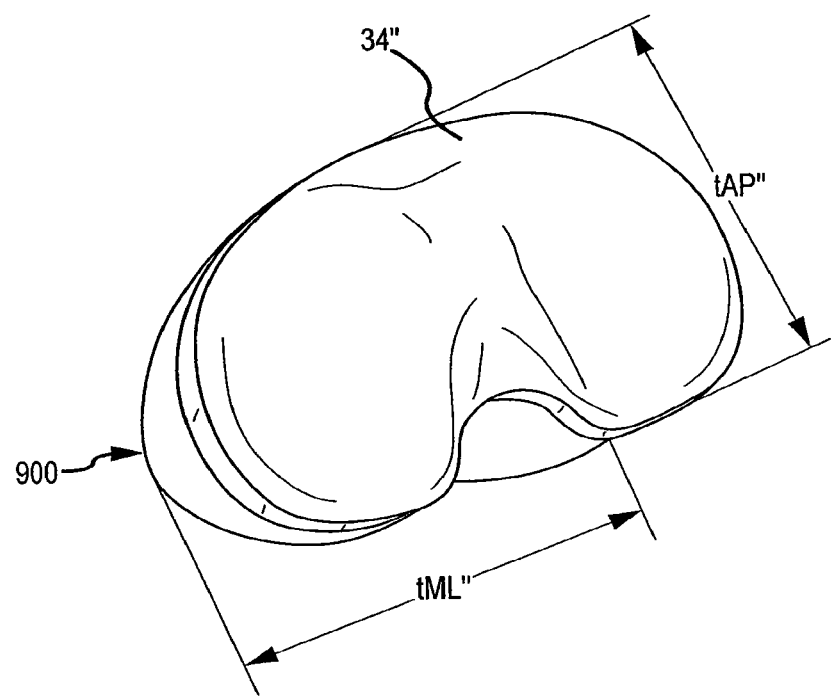
FIG. 30B is a top axial view of the implant superimposed on the tibia reference data.

As shown in FIG. 30B, which is a top axial view of the implant 34" superimposed on the tibia reference data 900, the implant 34" is opened with the tibia reference data 900 and is generally aligned with the tibia reference data 900 at the level of the cut plane r1 by the system 4. However, the implant 34" is not centered relative to the tibia reference data 900. The anterior/posterior extent tAP'" and medial/lateral extent tML'" of the tibia 28" at the cut level are found.

Figure 30C:
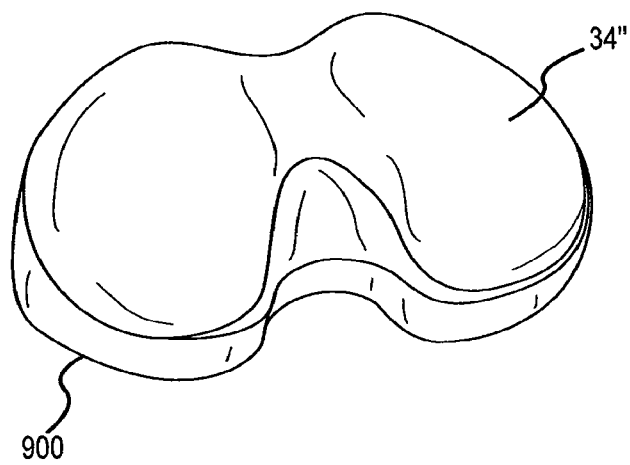
FIG. 30C is an axial view of the tibial implant aligned with the tibia reference data.

The implant 34" may be centered by the system (or manually by a user of the system). As indicated in FIG. 30C, which is an axial view of the tibial implant aligned with the tibia reference data 900, the tibia implant 34" is then centered relative to the anterior posterior extent tAP'" and the medial lateral extents tML'" of the tibia 28".

c. Determine Joint Line and Adjustment

In order to allow an actual physical arthroplasty implant to restore the patient's knee to the knee's pre-degenerated or natural configuration with the its natural alignment and natural tensioning in the ligaments, the condylar surfaces of the actual physical implant generally replicate the condylar surfaces of the pre-degenerated joint bone. In one embodiment of the systems and methods disclosed herein, condylar surfaces of the bone model 28" are surface matched to the condylar surfaces of the implant model 34". However, because the bone model 28" may be bone only and not reflect the presence of the cartilage that actually extends over the pre-degenerated condylar surfaces, the surface matching of the modeled condylar surfaces may be adjusted to account for cartilage or proper spacing between the condylar surfaces of the cooperating actual physical implants (e.g., an actual physical femoral implant and an actual physical tibia implant) used to restore the joint such that the actual physical condylar surfaces of the actual physical cooperating implants will generally contact and interact in a manner substantially similar to the way the cartilage covered condylar surfaces of the pre-degenerated femur and tibia contacted and interacted.

i. Determine Adjustment Value tr

Thus, in one embodiment, the implant model is modified or positionally adjusted (via e.g. the tibia cut plane) to achieve the proper spacing between the femur and tibia implants. To achieve the correct adjustment or joint spacing compensation, an adjustment value tr may be determined. In one embodiment, the adjustment value tr that is used to adjust the implant location may be based off of an analysis associated with cartilage thickness. In another embodiment, the adjustment value tr used to adjust the implant location may be based off of an analysis of proper joint gap spacing, as described above with respect to FIGS. 14G and 14H. Both of the methods are discussed below in turn.

1. Determining Cartilage Thickness

Figure 30D:
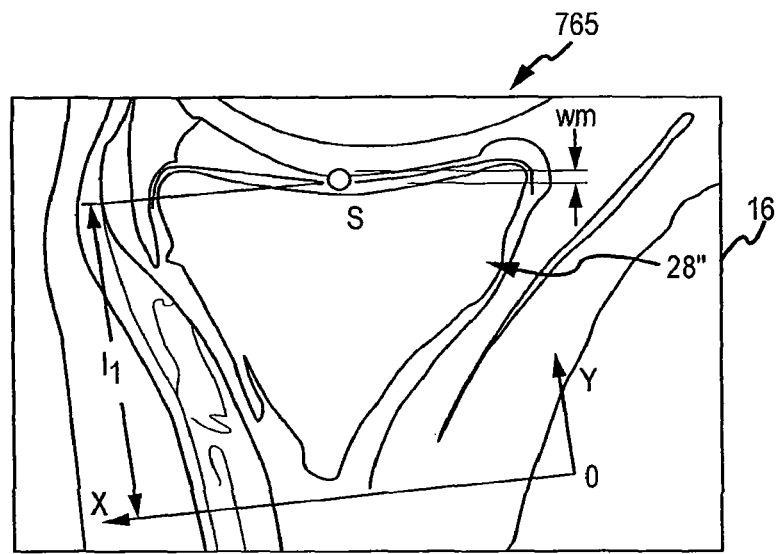
FIG. 30D is a MRI imaging slice of the medial portion of the proximal tibia and indicates the establishment of landmarks for the tibia POP design, as depicted in a sagittal view.
Figure 30E:
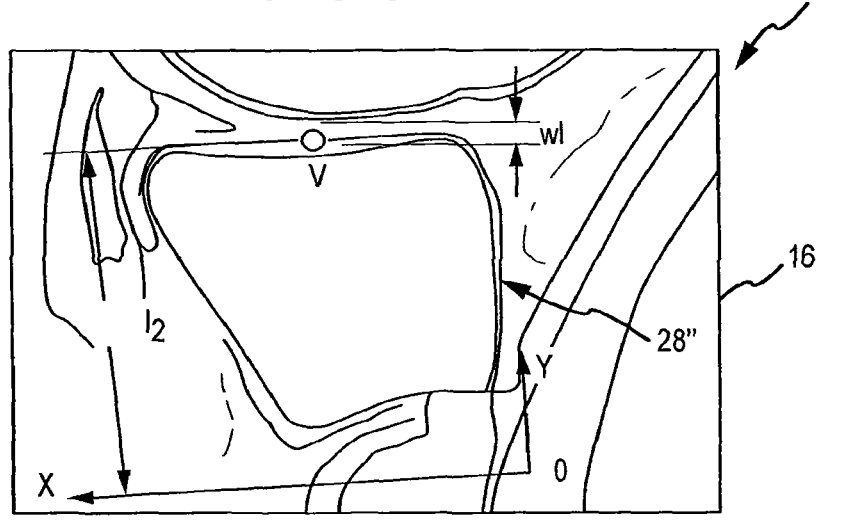
FIG. 30E is a MRI imaging slice of the lateral portion of the proximal tibia, as depicted in a sagittal view.

FIG. 30D is a MRI image slice of the medial portion of the proximal tibia and indicates the establishment of landmarks for the tibia POP design. FIG. 30E is a MRI image slice of the lateral portion of the proximal tibia. The wm in FIG. 30D represents the cartilage thickness of the medial tibia meniscus, and the wl in FIG. 30E represents the cartilage thickness of the lateral tibia meniscus. In one embodiment, the cartilage thicknesses wl and wm are measured for the tibia meniscus for both the lateral and medial plateaus 760, 765 via the MRI slices depicted in FIGS. 30D and 30E. The measured thicknesses may be compared. If the cartilage loss is observed for the medial plateau 765, then the $wl_{min}$ of lateral plateau 760 is selected as the minimum cartilage thickness. Similarly, if the lateral plateau 760 is damaged due to cartilage loss, then the $wm_{min}$ of medial plateau 765 is selected as the minimum cartilage thickness. The minimum cartilage wr may be illustrated in the formula, wr=min (wm, wl). In one embodiment, for purposes of the adjustment to the tibia, the adjustment value tr may be may be equal to the minimum cartilage value wr.

2. Determining Joint Gap

In one embodiment, the joint gap is analyzed as discussed above with respect to FIGS. 14G and 14H to determine the restored joint line gap Gp3. In one embodiment, for purposes of the adjustment to the tibia shape matching, the adjustment value tr may be calculated as being half of the value for Gp3, or in other words, tr=Gp3/2.

d. Determine Compensation for Joint Spacing

Figure 30F:
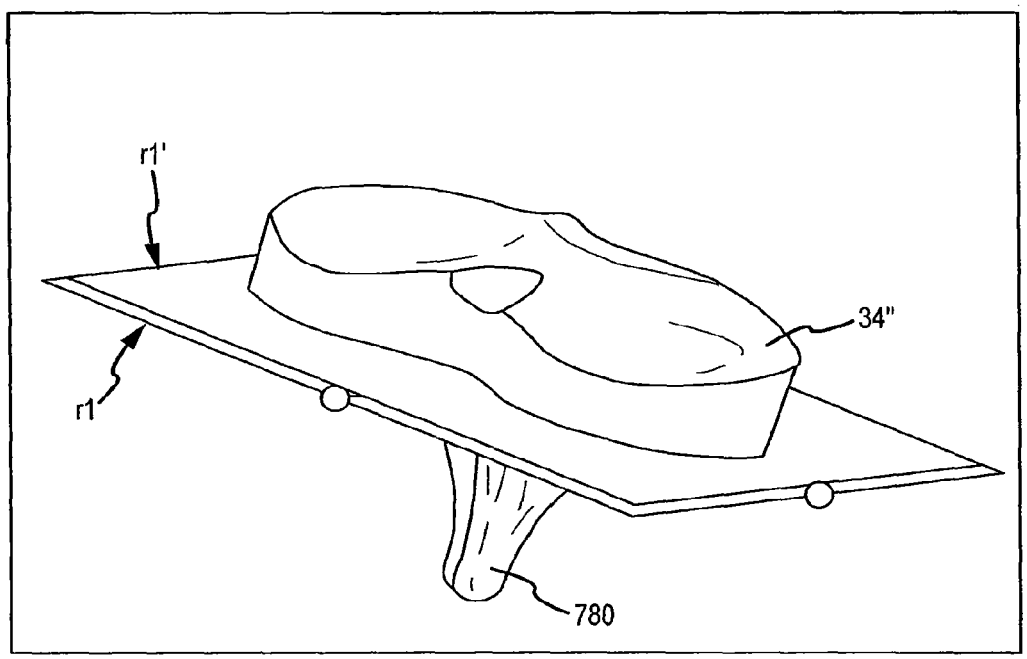
FIG. 30F is an isometric view of the 3D model of the tibia implant and the cut plane.

After centering the implant 34" within the cut plane, joint spacing compensation is taken into account. As shown in FIG. 30F, which is an isometric view of the tibia implant and the cut plane, the implant 34" and cut plane-r1 are moved in a direction that is generally perpendicular to both the proximal and sagittal reference lines by an amount equal to adjustment value tr, thereby creating an adjusted cut plane r1'. In one embodiment, the adjustment value tr is equal to approximately one-half of the joint spacing. In other embodiments, the adjustment value tr is equal to the cartilage thickness.

Thus, the implant candidate may be selected relative to the joint spacing compensation that was determined previously with reference to FIGS. 14G, 14H, 30D and 30E. As discussed above, in one embodiment, once the joint spacing compensation is determined, one-half of the joint spacing compensation will be factored in to the femur planning process and one-half of the joint spacing compensation will be factored in to the tibia planning process. That is, the femur implant is adjusted by an amount equal to one-half of the joint spacing compensation. Thus, the candidate femur implant will be chosen such that when it is positioned on the femur relative to the joint spacing compensation, the candidate implant will approximate the pre-degenerated joint line. Similarly, the tibia implant is adjusted by an amount equal to one-half of the joint spacing compensation. Thus, the candidate tibia implant will be chosen such that when it is positioned on the tibia relative to the joint spacing compensation, the candidate implant will approximate the pre-degenerated joint line. Also, the tibia implant mounting post 780 (see FIG. 31B) and the femur implant mounting post 781 (see FIG. 31A) will be oriented at approximately the center of the tibia and femur.

F. Verification of Implant Planning Models and Generation of Surgical Jigs Based on Planning Model Information FIGS. 31A1-32 illustrate one embodiment of a verification process that may be utilized for the preoperative planning process disclosed herein. FIGS. 31A1-31B are sagittal views of a 2D image slice of the femur 28' (FIGS. 31A1 and 31A2) and the tibia 28" (FIG. 31B) wherein the 2D computer generated implant models 34 are also shown. As can be understood from FIGS. 31A1-31B, verification for both the distal femur and proximal tibia is performed by checking the reference lines/planes in 2D sagittal views. The reference lines/planes may also be checked in other views (e.g. coronal or axial). For example, and as can be understood from FIGS. 31A1 and 31A2, for the femur planning model, the flexion-extension rotation is verified by checking whether the inflection point 506 of the anterior cortex of the femur 28' sufficiently contacts the interior surface 510 of the anterior flange 512 of implant 34'. That is, as can be understood from FIG. 31A2, when the implant 34' is properly aligned with the femur 28', the flange point 500 of the implant should touch the inflection point of the segmentation spline or femur 28'.

Figure 31B:
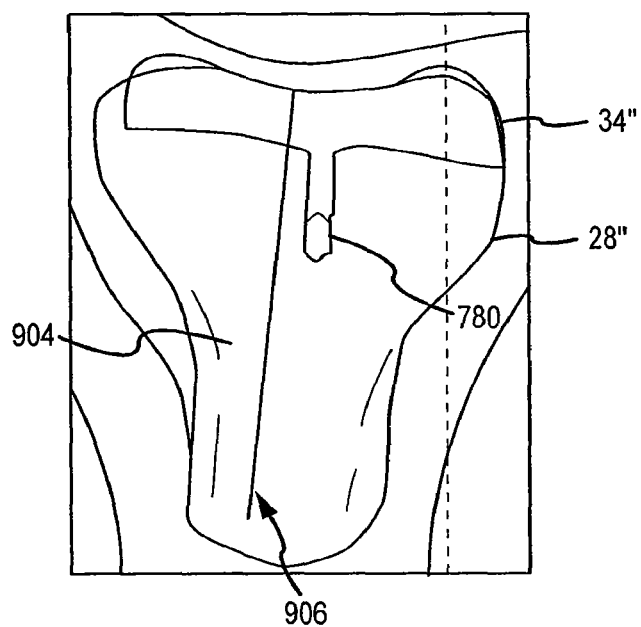
FIG. 31B is a sagittal view of a 2D imaging slice of the tibia wherein the 2D computer generated implant model is also shown.

As can be understood with reference to FIG. 31B, the tibia planning may be verified by looking at a 2D sagittal slice. Depending on the initial planning choice made above, one of the following can be verified: 1) whether the size of the tibial implant 34" matches or corresponds with the size of the femoral implant 34', or 2) whether the tibial implant 34" is one size larger or one size smaller than the femoral implant 34' size (e.g., a size 2 femur, and a size 1 tibia; or a size 2 femur, and a size 2 tibia; or a size 2 femur, and a size 3 tibia). In other embodiments, the size of tibial implant may be chosen without taking into account the size of the femoral implant. One of skill in the art will recognize that different implant manufacturers may utilize a different naming convention to describe different sizes of implants. The examples provided herein are provided for illustrative purposes and are not intended to be limiting.

As indicated in FIG. 31B, the placement of the tibial implant can be verified by viewing the anterior and posterior positions of the implant 34" relative to the tibial bone 28". If the implant is properly positioned, the implant should not extend beyond the posterior or anterior edge of the tibia bone. The flexion-extension of the tibia 28" can be verified by checking that the tibial implant reference line 906, which is a line segment approximating the normal direction of the implant's proximal surface, is at least parallel with the posterior surface 904 of the tibia 28" or converging with the posterior tibial surface 906 around the distal terminus of the tibial shaft.

Figures 32A, 32B, 32C:
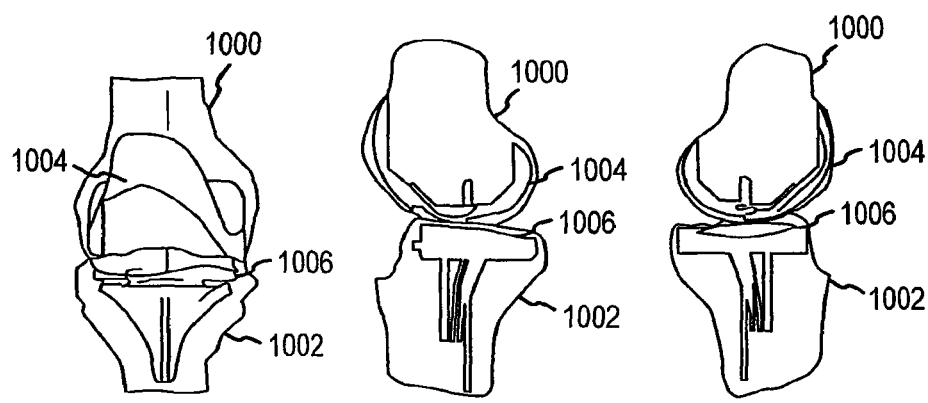
FIGS. 32A-32C are various views of the 2D implant models superimposed on the 2D bone models.
Figure 32D:
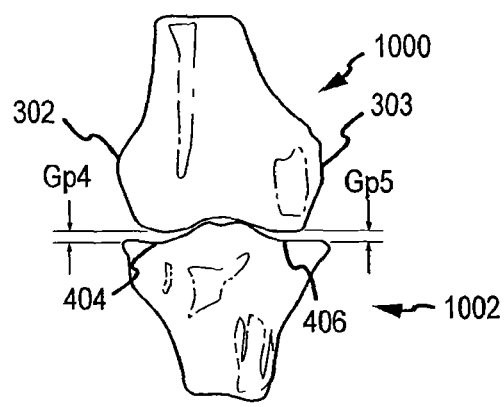
FIG. 32D is a coronal view of the 2D bone models.
Figure 32E:
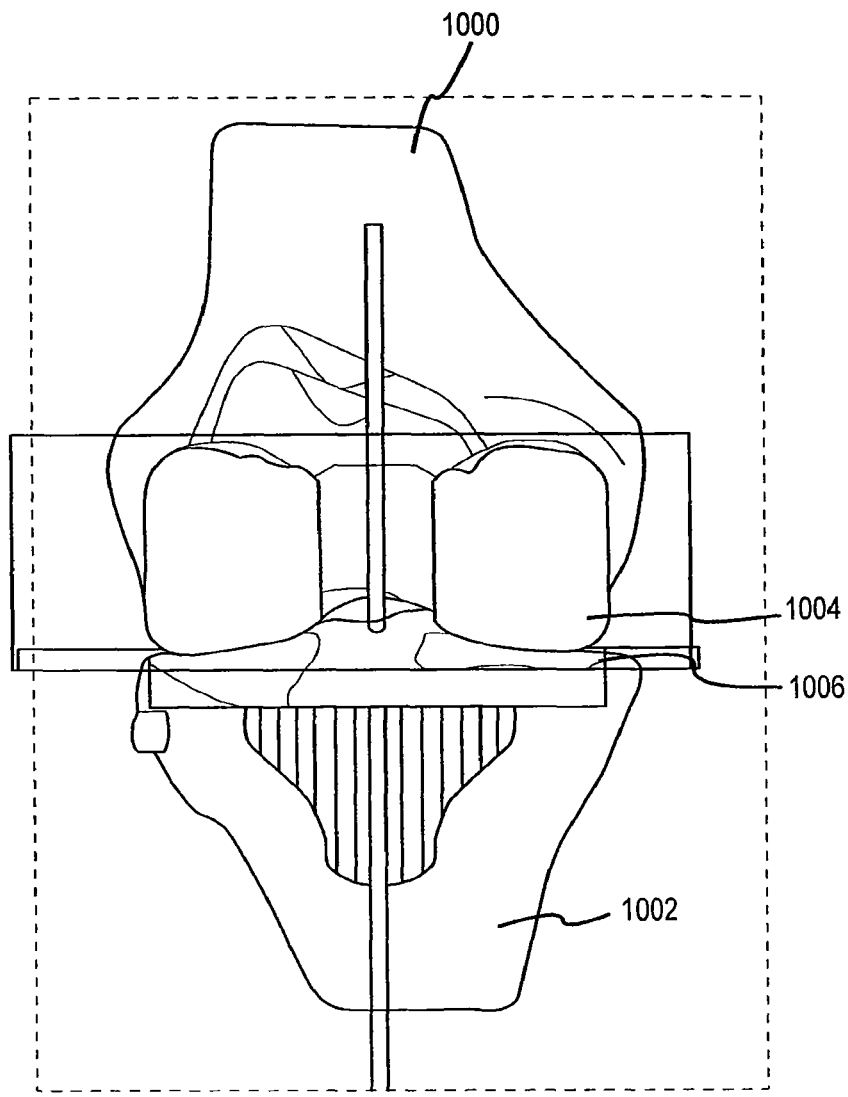
FIGS. 32E-32G are various views of the 2D implant models superimposed on the 2D bone models.

In other embodiments, as shown in FIGS. 32A-32G and FIGS. 33A-33C, the planning can also be confirmed from generated 3D bone models 1000, 1002 and 3D implant models 1004, 1006. If the planning is done incorrectly, the reference lines 100, 100', 900, 900' will be corrected in the 2D MRI views to amend the planning. FIGS. 32A-32C and FIGS. 32E-32G are various views of the implant 3D models 1004, 1006 superimposed on the 3D hone models 1000, 1002. FIG. 32D is a coronal view of the bone models 1000, 1002.

Figure 32F:
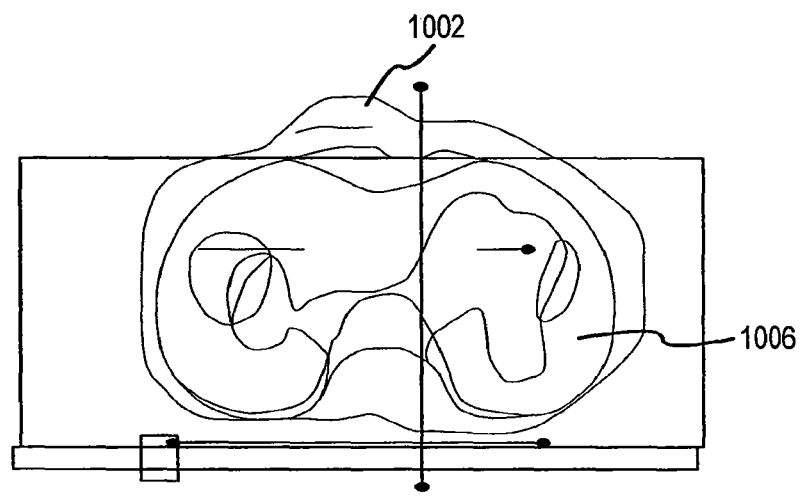
Figure 32G:
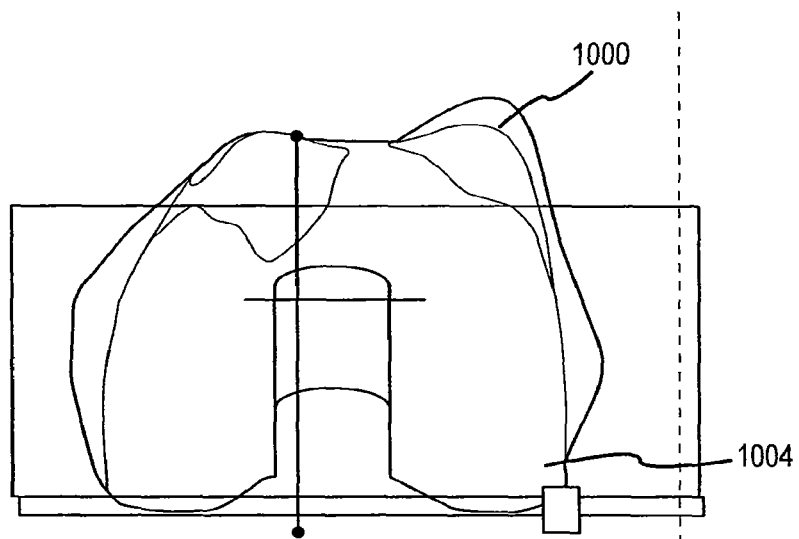

FIGS. 32A-32G show an embodiment of the POP system disclosed herein. The alignment of the implant models 1004, 1006 with the hone models 1000, 1002 is checked in the anterior view (FIG. 32A), the posterior view (FIG. 32E), the lateral view (FIG. 32B), the medial view (FIG. 32C), the top view (FIG. 32F) and the bottom view (FIG. 32G).

The flexion/extension between the femur and tibia implant models 1004, 1006 and the femur and tibia bone models 1000, 1002 is examined in both the medial view and the lateral view. For example, FIG. 32B shows the lateral view wherein the knee is shown in full extension or 0 degree flexion and in its natural alignment similar to its pre-arthritis status (e.g., neutral, varus or valgus), and FIG. 32C shows the medial view of the knee in full extension or 0 degree flexion and in its natural alignment (e.g., neutral, varus or valgus).

FIG. 32D shows the varus/valgus alignment of the knee model 28 $m'$, 28 $m''$ with the absence of the implants 34 $m'$, 34 $m''$. The gaps Gp4, Gp5 between the lowermost portions of distal femoral condyles 302, 303 and the lowermost portions of the tibia plateau 404, 406 will be measured in the femoral and tibia bone models 28 $m'$, 28 $m''$. Gap Gp4 represents the distance between the distal lateral femoral condyle 302 and the lateral tibial plateau 404. Gap Gp5 represents the distance between the distal medial femoral condyle 303 and the medial tibial plateau 406. In the varus/valgus rotation and alignment, Gp4 is substantially equal to Gp5, or |Gp4−Gp5|<<1 mm. FIG. 32D shows the knee model 28 $m'$, 28 $m''$ that is intended to restore the patient's knee back to his pre-OA stage.

The IR/ER rotation between the femur and tibia implant models 1004, 1006 and the femur and tibia bone models 1000, 1002 is examined in both the top and bottom views. For example. FIG. 32F shows the top view of the tibia showing the IR/ER rotation between no flexion and high flexion, and FIG. 32G shows the bottom view of the femur showing the IR/ER rotation between no flexion and high flexion. The stem of the tibia implant model 1006 and the surgical cut plane of the tibia implant model 1006 provide the information for the IR/ER rotation.

Figure 33A:
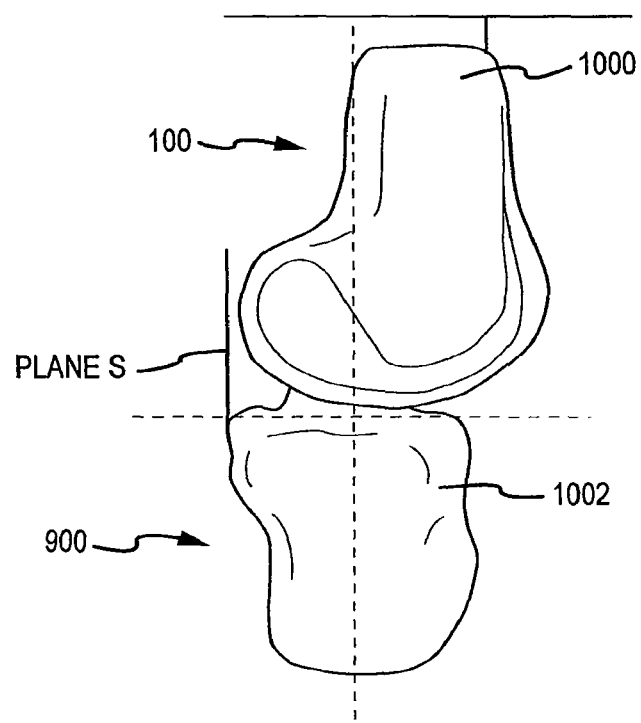
FIG. 33A is a medial view of the 3D bone models.
Figure 33B:
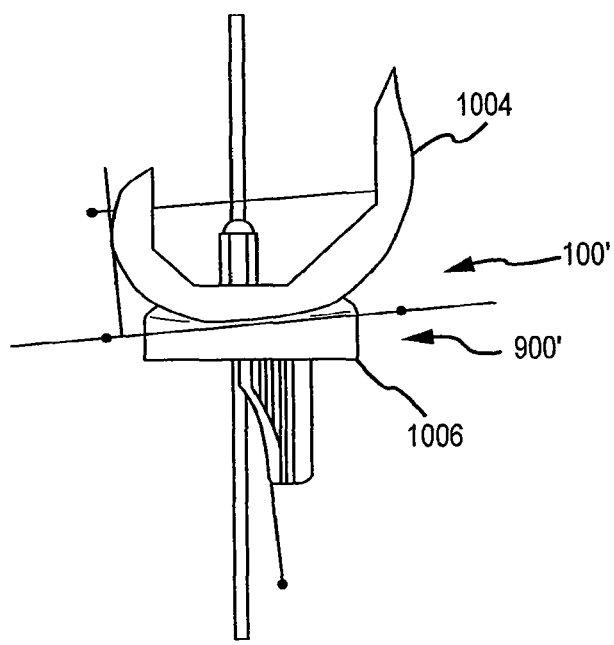
FIG. 33B is a medial view of the 3D implant models
Figure 33C:
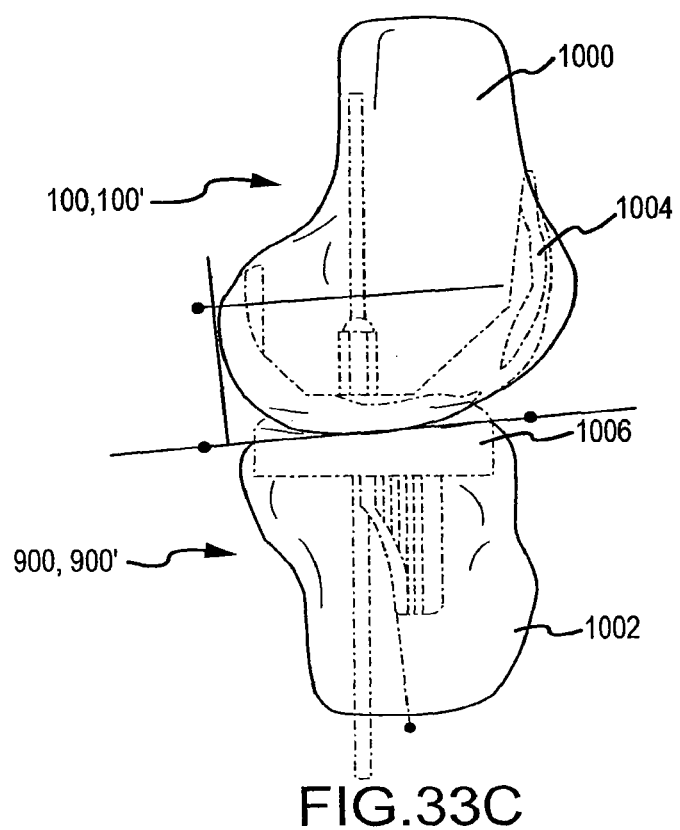
FIG. 33C is a medial view of the 3D implant models superimposed on the 3D bone models.
Figure 34A:
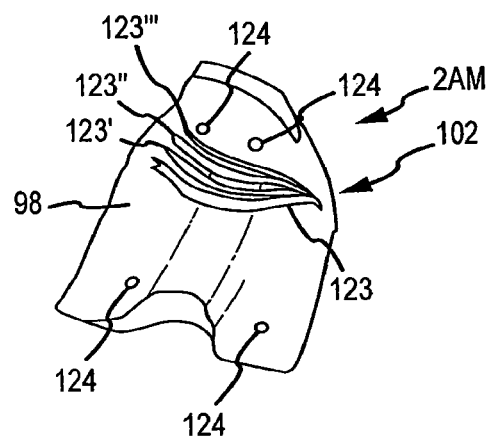
FIGS. 34A-35B illustrate isometric views of embodiments of the arthroplasty jigs configured to provide natural alignment resections, zero degree mechanical axis alignment resections, and resections resulting in alignments between zero degree mechanical axis alignment and natural alignment.
Figure 34B:
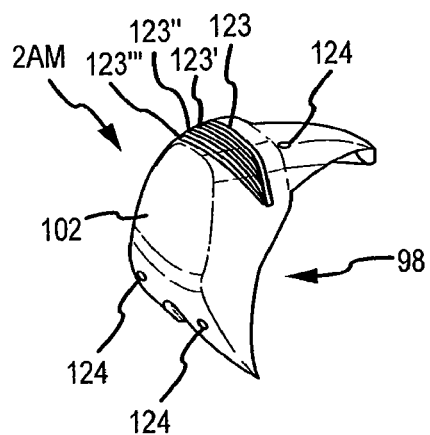
Figure 35A:
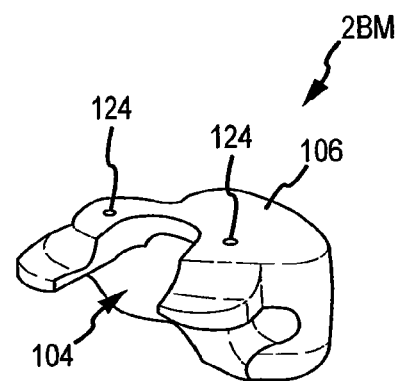
Figure 35B:
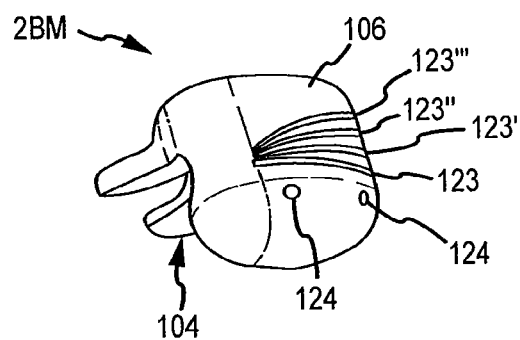

FIGS. 33A-33C show another embodiment of the POP system disclosed herein. FIG. 33A is an medial view of the 3D bone models. FIG. 33B is an medial view of the 3D implant models. FIG. 33C is an medial view of the 3D implant models superimposed on the 3D bone models.

As shown in FIG. 33A, a 3D model of the femur bone 1000 and a 3D model of the tibia bone 1002 may be generated from the 2D segmentation splines of image slices and the reference data 100, 900 determined above for verification of the POP. As shown in FIG. 33B, a 3D model of the femur implant 1004 and a 3D model of the tibia implant 1006 may be generated based on the reference lines 100', 900' determined above for verification of the POP. The implant models 1004, 1006 and the bone models 1000, 1002 are aligned based on the reference lines in a 3D computer modeling environment and the alignment is checked in the sagittal view as shown in FIG. 33C. If the alignment of the bone models 1000, 1002 and the implant models 1004, 1006 is not correct, the reference lines 100, 100', 900, 900' will be corrected in the 2D views to amend the planning.

The knee model 28', 28", 1000, 1002 and associated implant models 34', 34", 1004, 1006 developed through the above-discussed processes include dimensions, features and orientations that the system 10 depicted in FIG. 1A can be utilized to generate 3D models of femur and tibia cutting jigs 2. The 3D model information regarding the cutting jigs can then be provided to a CNC machine 10 to machine the jigs 2 from a polymer or other material.

G. Mechanical Axis Alignment

While much of the preceding disclosure is provided in the context of achieving natural alignment for the patient's knee post implantation of the actual physical femur and tibia implants, it should be noted that the systems and methods disclosed herein can be readily modified to produce an arthroplasty jig 2 that would achieve a zero degree mechanical axis alignment for the patient's knee post implantation.

For example, in one embodiment, the surgeon utilizes a natural alignment femoral arthroplasty jig 2A as depicted in FIGS. 2A and 2B to complete the first distal resection in the patient's femoral condylar region. Instead of utilizing a natural alignment tibia arthroplasty jig 2B as depicted in FIGS. 2C and 2D, the surgeon instead completes the first proximal resection in the patient's tibia plateau region via free hand or a mechanical axis guide to cause the patient's tibia implant to result in a mechanical axis alignment or an alignment based off of the mechanical axis (e.g., an alignment that is approximately one to approximately three degrees varus or valgus relative to zero degree mechanical axis).

In one embodiment, as indicated in FIGS. 34A-35B, the arthroplasty jigs 2AM and 2BM may be configured to provide bone resections that lead to natural alignment, mechanical axis alignment or alignments in between the two. For example, the jigs 2AM and 2BM may have a natural alignment saw slot 123 and one or more non-natural alignment saw slots 123', 123" and 123''' that may, for example, be one degree, two degrees, three degrees or some other incremental measurement away from natural alignment and towards zero degree mechanical axis alignment. The surgeon may select a two degree deviation slot 123" based on a physical inspection and surgical experience.

In one embodiment of the POP systems and methods disclosed herein, instead of superposing the 3D hone models 1000, 1002 to the 3D implant models 1004, 1006 in a manner that results in the saw cut and drill hole data 44 that leads to the production of natural alignment arthroplasty jigs 2A, 2B, the superposing of the bone and implant models 1000, 1002, 1004, 1006 may be conducted such that the resulting saw cut and drill hole data 44 leads to the production of zero degree mechanical axis alignment arthroplasty jigs or some other type of arthroplasty jig deviating in a desired manner from zero degree mechanical axis.

Thus, depending on the type of arthroplasty jig desired, the systems and methods disclosed herein may be applied to both the production of natural alignment arthroplasty jigs, zero degree mechanical axis alignment jigs, or arthroplasty jigs configured to provide a result that is somewhere between natural alignment and zero degree mechanical axis alignment.

Although the present invention has been described with reference to preferred embodiments, persons skilled in the art will recognize that changes may be made in form and detail without departing from the spirit and scope of the invention.

The invention claimed is:

1. A method of performing an arthroplasty procedure on a femur of a patient, the method comprising:
   a) generating an operation plan of the arthroplasty procedure, the generating of the operation plan including:
      i) displaying on a three dimensional computer model of the femur of the patient a first point at a most distal location on a condylar surface of the computer model of the femur of the patient and a second point at a location on the condylar surface of the computer model of the femur of the patient that is proximal the first point;
      ii) using the first point and second point to position a three dimensional computer model of an implant relative to the three dimensional computer model of the femur of the patient, a position of the three dimensional computer model of the implant relative to the three dimensional computer model of the femur of the patient being reflective of the implant being implanted on the femur; and
      iii) computer defining a resection of the femur in the computer model of the femur of the patient based on the position of the three dimensional computer model of the implant relative to the three dimensional computer model of the femur of the patient;
   b) computer referencing the computer defined resection to a registration surface of the three dimensional computer model of the femur of the patient such that a position of the computer defined resection relative to the registration surface is reflective of a position of an actual resection to be made in the femur of the patient during the arthroplasty procedure and according to the operation plan.

2. The method of claim 1, wherein the computer referencing includes matching movements relative to an origin in a computer coordinate system of a bone-only version of the three dimensional computer model of the femur and a bone and cartilage version of the three dimensional computer model of the femur.

3. The method of claim 2, wherein the computer defining the resection of the femur occurs in relation to the bone-only version of the three dimensional computer model of the femur, and the registration surface of the three dimensional computer model is with respect to the bone and cartilage version of the three dimensional computer model.

4. The method of claim 1, further comprising displaying on the three dimensional computer model of the implant a third point at a most distal location on a condylar surface of the computer model of the implant and a fourth point at a location on the condylar surface of the computer model of the implant proximal the third point, wherein using the first and second points to position the three dimensional computer model of the implant relative to the three dimensional computer model of the femur of the patient includes respectively positionally matching the first point with the third point and the second point with the fourth point.

5. The method of claim 4, wherein the positionally matching occurs in two dimensions.

6. The method of claim 5, wherein the positionally matching occurring in two dimensions includes projecting the first, second, third and fourth points to a sagittal plane of the three dimensional computer model of the femur of the patient and the three dimensional computer model of the implant.

7. The method of claim 4, wherein the positionally matching employs iterative closest point matching.

8. The method of claim 4, wherein the second point is at a most posterior location on the condylar surface of the computer model of the femur of the patient, and the fourth point is at a most posterior location on the condylar surface of the computer model of the implant.

9. The method of claim 1, wherein the operation plan takes place preoperatively.

10. The method of claim 1, further comprising: c) contacting the femur at a location corresponding to the registration surface of the three dimensional computer model of the femur of the patient.

11. The method of claim 10, wherein step c) facilitates guidance of a cutting tool to resect the femur according to the operation plan.

12. The method of claim 10, wherein step c) occurs subsequent to steps a) and b).

13. The method of claim 11, wherein the contacting the femur is via a mating surface defined in an arthroplasty jig according to the registration surface of the three dimensional computer model of the femur, and the guidance of the cutting tool to resect the femur according to the operation plan is via a resection slot of the arthroplasty jig, the resection slot having been defined in the arthroplasty jig according to the computer defined resection.

14. The method of claim 11, further comprising guiding the cutting tool to resect the femur according to the operation plan subsequent the femur being contacted at the location corresponding to the registration surface of the three dimensional computer model of the femur of the patient, the contact registering the computer defined resection with the femur.

15. The method of claim 14, wherein the contacting the femur is via a mating surface defined in an arthroplasty jig according to the registration surface of the three dimensional computer model of the femur, and the guiding of the cutting tool to resect the femur according to the operation plan is via a resection slot of the arthroplasty jig, the resection slot having been defined in the arthroplasty jig according to the computer defined resection.

16. The method of claim 14, wherein the second point is a most posterior location on the condylar surface of the computer model of the femur of the patient.

17. A method of performing an arthroplasty procedure on a femur of a patient, the method comprising:
   a) generating an operative plan of the arthroplasty procedure, the generating of the operative plan including:
      i) displaying on a three dimensional computer model of the femur of the patient a first point at a most distal location on a condylar surface of the computer model of the femur of the patient and a second point at a location on the condylar surface of the computer model of the femur of the patient that is proximal the first point;
      ii) using the first point and second point to position a three dimensional computer model of an implant relative to the three dimensional computer model of the femur of the patient, a position of the three dimensional computer model of the implant relative to the three dimensional computer model of the femur of the patient being reflective of the implant being implanted on the femur; and iii) computer defining a resection of the femur in the computer model of the femur of the patient based on the position of the three dimensional computer model of the implant relative to the three dimensional computer model of the femur of the patient;

b) computer referencing the computer defined resection to a registration surface of the three dimensional computer model of the femur of the patient such that a position of the computer defined resection relative to the registration surface is reflective of a position of an actual resection to be made in the femur of the patient during the arthroplasty procedure and according to the operative plan; and c) guiding a cutting tool in resecting the femur according the operative plan subsequent the femur being contacted at a location corresponding to the registration surface of the three dimensional computer model of the femur of the patient, the contact registering the computer defined resection with the femur.

18. The method of claim 17, wherein the contacting the femur is via a mating surface defined in an arthroplasty jig according to the registration surface of the three dimensional computer model of the femur, and the guiding of the cutting tool to resect the femur according to the operative plan is via a resection slot of the arthroplasty jig, the resection slot having been defined in the arthroplasty jig according to the computer defined resection.

19. The method of claim 17, wherein the second point is a most posterior location on the condylar surface of the computer model of the femur of the patient.

20. The method of claim 17, further comprising displaying on the three dimensional computer model of the implant a third point at a most distal location on a condylar surface of the computer model of the implant and a fourth point at a location on the condylar surface of the computer model of the implant proximal the third point, wherein using the first and second points to position the three dimensional computer model of the implant relative to the three dimensional computer model of the femur of the patient includes respectively positionally matching the first point with the third point and the second point with the fourth point.

21. The method of claim 20, wherein the positionally matching occurs in two dimensions.

22. The method of claim 21, wherein the positionally matching occurring in two dimensions includes projecting the first, second, third and fourth points to a sagittal plane of the three dimensional computer model of the femur of the patient and the three dimensional computer model of the implant.

23. The method of claim 20, wherein the positionally matching employs iterative closest point matching.

24. The method of claim 20, wherein the second point is at a most posterior location on the condylar surface of the computer model of the femur of the patient, and the fourth point is at a most posterior location on the condylar surface of the computer model of the implant.

25. The method of claim 17, wherein the operative plan takes place preoperatively.

26. A method of performing an arthroplasty procedure on a femur of a patient, the arthroplasty procedure comprising an incision, a resection, and an implantation, the method comprising:

a) generating a surgical plan prior to the incision of the arthroplasty procedure, the generating the surgical plan including:
   i) displaying on a three dimensional computer model of the femur of the patient a first point at a distal location on a condylar surface of the computer model of the femur of the patient and a second point at a location on the condylar surface of the computer model of the femur of the patient that is proximal the first point;
   ii) using the first point and second point to position a three dimensional computer model of an implant relative to the three dimensional computer model of the femur of the patient, a position of the three dimensional computer model of the implant relative to the three dimensional computer model of the femur of the patient being reflective of the implant being positioned on the femur during the implantation of the arthroplasty procedure; and
   iii) computer defining a virtual resection of the femur in the computer model of the femur of the patient based on the position of the three dimensional computer model of the implant relative to the three dimensional computer model of the femur of the patient;

b) subsequent to step a) and prior to the incision of the arthroplasty procedure, computer referencing the virtual resection to a registration surface of the three dimensional computer model of the femur of the patient such that a position of the virtual resection relative to the registration surface is reflective of a position of the resection of the arthroplasty procedure on the femur of the patient and according to the surgical plan; and c) subsequent to step b) and subsequent to the incision of the arthroplasty procedure, guiding a cutting tool in performing the resection of the femur according the surgical plan subsequent the femur being contacted at a location corresponding to the registration surface of the three dimensional computer model of the femur of the patient, the contact registering the computer defined resection with the femur.

27. The method of claim 26, wherein the distal location comprises a most distal location on a condylar surface of the computer model of the femur of the patient.

* * * * *